US012201776B2

United States Patent
Holyoake et al.

(10) Patent No.: US 12,201,776 B2
(45) Date of Patent: Jan. 21, 2025

(54) APPARATUS FOR USE IN A RESPIRATORY SUPPORT SYSTEM

(71) Applicant: Fisher & Paykel Healthcare Limited, Auckland (NZ)

(72) Inventors: Bruce Gordon Holyoake, Auckland (NZ); Samantha Dale Oldfield, Auckland (NZ); Alicia Jerram Hunter Evans, Auckland (NZ); Callum James Thomas Spence, Auckland (NZ); Craig Karl White, Auckland (NZ); Dexter Chi Lun Cheung, Auckland (NZ); Matthew Jon Payton, Auckland (NZ); Michael Robert Barraclough, Auckland (NZ); Daniel John Smith, Auckland (NZ); Kevin Blake Powell, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 17/887,324

(22) Filed: Aug. 12, 2022

(65) Prior Publication Data
US 2023/0147017 A1    May 11, 2023

Related U.S. Application Data

(63) Continuation of application No. 15/562,139, filed as application No. PCT/IB2016/051815 on Mar. 31, 2016, now Pat. No. 11,446,462.
(Continued)

(51) Int. Cl.
*A61M 16/10* (2006.01)
*A61M 16/00* (2006.01)
(Continued)

(52) U.S. Cl.
CPC ...... *A61M 16/107* (2014.02); *A61M 16/0066* (2013.01); *A61M 16/0069* (2014.02);
(Continued)

(58) Field of Classification Search
CPC ............ A61M 16/107; A61M 16/0816; A61M 16/0875
See application file for complete search history.

(56) References Cited

U.S. PATENT DOCUMENTS

| 132,604 A | 10/1872 | Smith et al. |
| 327,877 A | 10/1885 | Hodges |

(Continued)

FOREIGN PATENT DOCUMENTS

| CA | 208288 | 3/2022 |
| CN | 2652420 Y | 11/2004 |

(Continued)

OTHER PUBLICATIONS

Thomas Scientific, Coupling Insert, In-Line Hose Barb, [Post date: unknown], [Site seen Nov. 21, 2023], https://www.thomassci.com/Laboratory-Supplies/Tubing-Connectors/_/Coupling-Insert-In-Line-Hose-Barb-Straight-Thru2.

(Continued)

*Primary Examiner* — Joseph D. Boecker
*Assistant Examiner* — Thomas W Greig
(74) *Attorney, Agent, or Firm* — Knobbe, Martens, Olson & Bear, LLP

(57) ABSTRACT

An apparatus or kit for a respiratory support system for delivering humidified gas to a user or patient. The apparatus comprising a humidifier chamber in pneumatic communication with a gases source, an inspiratory conduit in pneumatic communication with the humidifier chamber downstream of the humidifier chamber, a filter that is in pneumatic communication with the inspiratory conduit downstream of
(Continued)

the inspiratory conduit, and a patient interface for delivering humidified gas to a user or patient, wherein the patient interface is in pneumatic communication with the filter downstream of the filter, or is configured to be placed in pneumatic communication with the filter downstream of the filter.

43 Claims, 23 Drawing Sheets

Related U.S. Application Data

(60) Provisional application No. 62/242,549, filed on Oct. 16, 2015, provisional application No. 62/196,235, filed on Jul. 23, 2015, provisional application No. 62/140,648, filed on Mar. 31, 2015.

(51) Int. Cl.
*A61M 16/04* (2006.01)
*A61M 16/06* (2006.01)
*A61M 16/08* (2006.01)
*A61M 16/16* (2006.01)
*A61M 16/20* (2006.01)

(52) U.S. Cl.
CPC ...... *A61M 16/024* (2017.08); *A61M 16/0497* (2013.01); *A61M 16/0666* (2013.01); *A61M 16/0672* (2014.02); *A61M 16/0816* (2013.01); *A61M 16/0875* (2013.01); *A61M 16/109* (2014.02); *A61M 16/1095* (2014.02); *A61M 16/16* (2013.01); *A61M 16/208* (2013.01); *A61M 2016/0027* (2013.01); *A61M 2016/0039* (2013.01); *A61M 2205/3368* (2013.01); *A61M 2205/3653* (2013.01); *A61M 2205/50* (2013.01); *A61M 2209/088* (2013.01)

(56) References Cited

U.S. PATENT DOCUMENTS

| | | | |
|---|---|---|---|
| 643,358 | A | 2/1900 | Konold |
| 778,936 | A | 1/1905 | Witmond |
| 1,080,674 | A | 12/1913 | Berg |
| 1,130,726 | A | 3/1915 | Greve |
| 1,194,793 | A | 8/1916 | Styers |
| 1,673,338 | A | 6/1928 | Mitchell |
| 1,880,098 | A | 9/1932 | Mair |
| 1,916,449 | A | 7/1933 | Tompkins |
| 2,124,474 | A | 7/1938 | Scholtes |
| 2,479,580 | A | 8/1949 | Marco |
| 2,727,759 | A | 12/1955 | Elliott |
| 2,910,308 | A | 10/1959 | Carr |
| 3,287,031 | A | 11/1966 | Simmons et al. |
| 3,323,774 | A | 6/1967 | Wilson |
| 3,513,844 | A | 5/1970 | Smith |
| 3,601,361 | A | 8/1971 | Hundhausen et al. |
| 3,813,115 | A | 5/1974 | French |
| 3,815,754 | A * | 6/1974 | Rosenberg ............ B01D 35/00 55/497 |
| 3,932,153 | A * | 1/1976 | Byrns ................ B01D 29/012 210/446 |
| 4,036,616 | A | 7/1977 | Byrns |
| 4,111,514 | A | 9/1978 | Brishka et al. |
| 4,128,407 | A * | 12/1978 | Chapel ............ A61M 16/1055 210/501 |
| 4,161,949 | A | 7/1979 | Thanawalla |
| 4,211,439 | A | 7/1980 | Moldestad |
| D267,199 | S | 12/1982 | Koenig |
| 4,386,948 | A | 6/1983 | Choksi et al. |
| 4,443,028 | A | 4/1984 | Hayes |
| 4,446,869 | A | 5/1984 | Knodle |
| 4,584,997 | A | 4/1986 | Delong |
| 4,589,684 | A | 5/1986 | Nowacki et al. |
| 4,601,495 | A | 7/1986 | Webb |
| 4,601,497 | A | 7/1986 | Bartholomew |
| 4,661,110 | A | 4/1987 | Fortier et al. |
| 4,676,241 | A | 6/1987 | Webb et al. |
| 4,758,023 | A | 7/1988 | Vermillion |
| 4,773,448 | A | 9/1988 | Francis |
| D300,271 | S | 3/1989 | Rudolph et al. |
| D300,272 | S | 3/1989 | Rudolph et al. |
| D302,040 | S | 7/1989 | Lambert et al. |
| 4,936,841 | A | 6/1990 | Aoki et al. |
| 5,005,571 | A | 4/1991 | Dietz |
| 5,009,252 | A | 5/1991 | Faughn |
| 5,040,527 | A | 8/1991 | Larson et al. |
| 5,064,226 | A | 11/1991 | Klas |
| D328,033 | S | 7/1992 | DiGuiseppi |
| 5,158,569 | A | 10/1992 | Strickland et al. |
| 5,169,180 | A | 12/1992 | Villani et al. |
| 5,230,727 | A * | 7/1993 | Pound ................ B01D 46/0012 55/494 |
| 5,281,206 | A | 1/1994 | Lopez |
| 5,335,656 | A | 8/1994 | Bowe et al. |
| D362,718 | S | 9/1995 | Deily et al. |
| D363,541 | S | 10/1995 | Cottone, Sr. et al. |
| 5,456,676 | A | 10/1995 | Nelson et al. |
| 5,460,172 | A * | 10/1995 | Eckerbom ........... A61M 16/085 128/205.12 |
| 5,529,284 | A | 6/1996 | Berger et al. |
| 5,584,997 | A | 12/1996 | Yagihashi et al. |
| 5,620,427 | A | 4/1997 | Werschmidt et al. |
| 5,718,143 | A | 2/1998 | Clowes |
| 5,725,258 | A | 3/1998 | Kujawski |
| 5,725,511 | A | 3/1998 | Urrutia |
| 5,735,271 | A | 4/1998 | Lorenzen et al. |
| 5,738,142 | A | 4/1998 | Eike et al. |
| 5,741,084 | A | 4/1998 | Del Rio et al. |
| D395,502 | S | 6/1998 | Deily et al. |
| 5,901,705 | A | 5/1999 | Leagre |
| D424,687 | S | 5/2000 | Hoenig et al. |
| D427,308 | S | 6/2000 | Zinger |
| 6,099,519 | A | 8/2000 | Olsen |
| D431,634 | S | 10/2000 | Mantz |
| D439,326 | S | 3/2001 | Hecker et al. |
| D443,863 | S | 6/2001 | Maccarone |
| D449,107 | S | 10/2001 | Madsen |
| 6,402,207 | B1 | 6/2002 | Segal et al. |
| 6,439,234 | B1 | 8/2002 | Curti et al. |
| 6,484,724 | B1 | 11/2002 | Sloan |
| D466,607 | S | 12/2002 | Cise |
| D468,015 | S | 12/2002 | Horppu |
| D471,262 | S | 3/2003 | Kozu |
| D472,316 | S | 3/2003 | Douglas et al. |
| D472,630 | S | 4/2003 | Douglas et al. |
| 6,561,549 | B1 | 5/2003 | Moris et al. |
| D476,232 | S | 6/2003 | Maus et al. |
| 6,581,974 | B1 | 6/2003 | Ragner et al. |
| 6,803,496 | B2 | 10/2004 | Elder et al. |
| 6,893,055 | B2 | 5/2005 | Thomas et al. |
| 6,915,705 | B1 | 7/2005 | Truitt |
| 6,932,390 | B1 | 8/2005 | Gretz |
| 6,953,354 | B2 | 10/2005 | Edirisuriya |
| 7,007,694 | B2 | 3/2006 | Aylsworth et al. |
| D522,109 | S | 5/2006 | White et al. |
| D522,360 | S | 6/2006 | Caserta |
| 7,201,167 | B2 | 4/2007 | Fink et al. |
| D543,620 | S | 5/2007 | Chu et al. |
| D547,657 | S | 7/2007 | Tacchella |
| D551,340 | S | 9/2007 | Wood et al. |
| 7,263,994 | B2 | 9/2007 | Gradon et al. |
| 7,267,121 | B2 | 9/2007 | Ivri |
| D553,005 | S | 10/2007 | Py |
| 7,290,541 | B2 | 11/2007 | Ivri et al. |
| D556,899 | S | 12/2007 | Veliss et al. |
| D557,414 | S | 12/2007 | Wentling |
| 7,306,121 | B2 | 12/2007 | Ophardt |
| 7,311,752 | B2 | 12/2007 | Tepper |
| D565,731 | S | 4/2008 | Eisenkolb et al. |
| D570,457 | S | 6/2008 | Brown |
| 7,406,966 | B2 | 8/2008 | Wondka |

(56) References Cited

U.S. PATENT DOCUMENTS

| | | |
|---|---|---|
| 7,458,615 B2 | 12/2008 | White et al. |
| D586,907 S | 2/2009 | Judson |
| D586,911 S | 2/2009 | McAuley et al. |
| 7,484,769 B2 | 2/2009 | Domash et al. |
| D600,343 S | 9/2009 | Degabriele et al. |
| D606,494 S | 12/2009 | Holliday |
| D609,091 S | 2/2010 | Dubach |
| 7,666,170 B2 | 2/2010 | Guala |
| D612,481 S | 3/2010 | Reid et al. |
| 7,785,300 B2 | 8/2010 | Ishil et al. |
| D627,059 S | 11/2010 | Wood et al. |
| D628,288 S | 11/2010 | Row |
| D629,891 S | 12/2010 | Virr |
| D630,732 S | 1/2011 | Lev et al. |
| D631,542 S | 1/2011 | DeGross |
| 7,874,596 B2 | 1/2011 | Kertesz et al. |
| D637,713 S | 5/2011 | Nord et al. |
| 7,946,291 B2 | 5/2011 | Fink et al. |
| 8,006,877 B2 | 8/2011 | Lowry et al. |
| D645,547 S | 9/2011 | Lombardi et al. |
| 8,020,551 B2 | 9/2011 | Virr et al. |
| 8,092,409 B2 | 1/2012 | Mros et al. |
| D654,573 S | 2/2012 | Lombardi et al. |
| D656,231 S | 3/2012 | Henry et al. |
| 8,186,352 B2 | 5/2012 | Gunaratnam et al. |
| D661,785 S | 6/2012 | Johnson |
| 8,256,459 B2 | 9/2012 | Tesluk et al. |
| 8,257,286 B2 | 9/2012 | Meyer et al. |
| 8,287,517 B2 | 10/2012 | Hanlon et al. |
| 8,317,203 B2 | 11/2012 | Hermle et al. |
| D672,037 S | 12/2012 | Miller |
| 8,376,412 B2 | 2/2013 | Johnson |
| D677,789 S | 3/2013 | Row |
| 8,397,727 B2 | 3/2013 | Ng et al. |
| D682,415 S | 5/2013 | Mogensen et al. |
| 8,439,039 B2 | 5/2013 | Gunaratnam et al. |
| D685,463 S | 7/2013 | Veliss et al. |
| 8,485,193 B2 | 7/2013 | Worley |
| 8,534,278 B2 | 9/2013 | Colman et al. |
| D691,712 S | 10/2013 | Judson et al. |
| D691,717 S | 10/2013 | McLean et al. |
| D692,555 S | 10/2013 | Maksym et al. |
| D695,890 S | 12/2013 | Bowden et al. |
| D697,200 S | 1/2014 | Mahaffy |
| D698,440 S | 1/2014 | Lombardi, III |
| 8,622,057 B2 | 1/2014 | Ujhazy et al. |
| D707,355 S | 6/2014 | Bow |
| 8,741,220 B2 | 6/2014 | O'Donnell et al. |
| D709,996 S | 7/2014 | Yu |
| D710,695 S | 8/2014 | Pritikin |
| 8,814,849 B1 | 8/2014 | Winsor |
| 8,870,238 B2 | 10/2014 | Robert et al. |
| D717,942 S | 11/2014 | Neff et al. |
| D719,650 S | 12/2014 | Arinobe et al. |
| 8,960,727 B2 | 2/2015 | Kendrick |
| D724,720 S | 3/2015 | O'Connor et al. |
| 8,967,144 B2 | 3/2015 | Lurie |
| D726,287 S | 4/2015 | Steele |
| D727,492 S | 4/2015 | Scampoli |
| 9,010,330 B2 | 4/2015 | Barlow et al. |
| D732,664 S | 6/2015 | Woehr et al. |
| D735,038 S | 7/2015 | Tamarindo |
| D735,326 S | 7/2015 | Gulliver |
| D736,906 S | 8/2015 | Schultz |
| D736,914 S | 8/2015 | Schultz |
| D737,953 S | 9/2015 | Wells et al. |
| D737,963 S | 9/2015 | Srinivasan et al. |
| 9,132,252 B2 | 9/2015 | Barlow et al. |
| 9,188,267 B2 | 11/2015 | Fansler et al. |
| D746,416 S | 12/2015 | Bariar |
| D747,471 S | 1/2016 | Gulliver et al. |
| D747,794 S | 1/2016 | Greenberg et al. |
| D750,239 S | 2/2016 | Pappalardo |
| 9,259,535 B2 | 2/2016 | Anderson et al. |
| 9,265,909 B2 | 2/2016 | Ho et al. |
| D751,687 S | 3/2016 | Daly |
| 9,385,257 B2 | 3/2016 | Reuterholt et al. |
| D754,327 S | 4/2016 | Row |
| D757,259 S | 5/2016 | Duck |
| D757,933 S | 5/2016 | Lev et al. |
| D759,486 S | 6/2016 | Ingram |
| D762,843 S | 8/2016 | Formica |
| D764,049 S | 8/2016 | Cullen et al. |
| 9,440,040 B2 | 9/2016 | Klasek et al. |
| D768,285 S | 10/2016 | Reed |
| D771,247 S | 11/2016 | Shinohara et al. |
| 9,480,809 B2 | 11/2016 | Guney et al. |
| D777,317 S | 1/2017 | Soual et al. |
| D777,324 S | 1/2017 | Nguyen |
| D781,417 S | 3/2017 | Ingram |
| D784,525 S | 4/2017 | Nguyen |
| D784,529 S | 4/2017 | Steele et al. |
| D785,161 S | 4/2017 | Dravitzki et al. |
| D785,789 S | 5/2017 | Turturro et al. |
| D787,053 S | 5/2017 | Huang et al. |
| D787,054 S | 5/2017 | Rini et al. |
| D787,661 S | 5/2017 | Edwards et al. |
| D790,054 S | 6/2017 | Prentice et al. |
| 9,669,181 B2 | 6/2017 | Miller et al. |
| 9,675,774 B2 | 6/2017 | Cipollone |
| D791,310 S | 7/2017 | Maurice |
| D791,938 S | 7/2017 | Becker |
| D791,939 S | 7/2017 | Turturro et al. |
| D792,584 S | 7/2017 | Ingram et al. |
| D792,586 S | 7/2017 | Becker |
| D794,184 S | 8/2017 | Smith et al. |
| D794,781 S | 8/2017 | Gilbert et al. |
| D800,895 S | 10/2017 | Prentice |
| D804,023 S | 11/2017 | Huang et al. |
| 9,808,612 B2 | 11/2017 | Gulliver et al. |
| D804,661 S | 12/2017 | Shoji et al. |
| D805,629 S | 12/2017 | Fiorenza |
| D805,630 S | 12/2017 | Formica |
| D806,859 S | 1/2018 | Formica |
| D807,995 S | 1/2018 | Maeckelberghe et al. |
| D808,516 S | 1/2018 | Edwards |
| 9,868,001 B2 | 1/2018 | Walker et al. |
| 9,879,807 B2 | 1/2018 | Brugger et al. |
| D809,656 S | 2/2018 | Lau et al. |
| 9,884,176 B2 | 2/2018 | Fangrow |
| 9,890,651 B2 | 2/2018 | Heaven et al. |
| D816,216 S | 4/2018 | Gulliver et al. |
| D820,441 S | 6/2018 | Ketelhohn |
| D822,818 S | 7/2018 | Maeckelberghe |
| D825,749 S | 8/2018 | Huang et al. |
| D827,125 S | 8/2018 | Nilsson |
| D827,126 S | 8/2018 | Nilsson et al. |
| D832,431 S | 10/2018 | Turturro |
| D834,533 S | 11/2018 | Maroney |
| D834,712 S | 11/2018 | Gulliver et al. |
| D835,260 S | 12/2018 | Lisberg |
| D837,743 S | 1/2019 | Maroney |
| D841,147 S | 2/2019 | McCool et al. |
| D841,148 S | 2/2019 | Stoks et al. |
| D847,326 S | 4/2019 | Eury |
| 10,245,407 B2 | 4/2019 | Osborne |
| 10,265,492 B2 | 4/2019 | Amarasinghe et al. |
| D847,752 S | 5/2019 | Barrefelt |
| D849,232 S | 5/2019 | Virr |
| D849,242 S | 5/2019 | Wilson |
| D849,931 S | 5/2019 | Prentice |
| D852,356 S | 6/2019 | Steele et al. |
| 10,322,254 B2 | 6/2019 | Fong et al. |
| D852,949 S | 7/2019 | Klenner et al. |
| 10,335,583 B2 | 7/2019 | Gulliver et al. |
| D855,794 S | 8/2019 | Gray |
| D856,510 S | 8/2019 | Scheirlinck |
| D857,880 S | 8/2019 | Lau et al. |
| D860,445 S | 9/2019 | Ho |
| D861,162 S | 9/2019 | Gulliver et al. |
| D863,545 S | 10/2019 | Dantanarayana |
| 10,449,320 B2 | 10/2019 | Miller |
| D867,583 S | 11/2019 | Yang et al. |
| D867,586 S | 11/2019 | Kemps |

(56) References Cited

U.S. PATENT DOCUMENTS

| | | |
|---|---|---|
| D867,587 S | 11/2019 | Holtz et al. |
| D870,878 S | 12/2019 | Wilson |
| D875,242 S | 2/2020 | Gordon |
| D876,617 S | 2/2020 | Scheirlinck et al. |
| D878,546 S | 3/2020 | Formica |
| D878,549 S | 3/2020 | Wilson |
| D879,953 S | 3/2020 | Ljunglof et al. |
| D879,956 S | 3/2020 | Klenner |
| 10,576,233 B2 | 3/2020 | Harwood |
| D880,686 S | 4/2020 | Stoks et al. |
| D887,577 S | 6/2020 | Shor et al. |
| D893,024 S | 7/2020 | Whiteside |
| D893,016 S | 8/2020 | Wilson |
| D894,376 S | 8/2020 | Boyes |
| D895,103 S | 9/2020 | Dantanarayana |
| D896,758 S | 9/2020 | Watkins |
| D896,929 S | 9/2020 | Vranish |
| 10,786,663 B2 | 9/2020 | Lauer |
| D899,590 S | 10/2020 | Gulliver et al. |
| 10,792,486 B2 | 10/2020 | Nelson |
| D901,673 S | 11/2020 | Gordon |
| D903,121 S | 11/2020 | Chan |
| 10,835,733 B1 | 11/2020 | Gulliver et al. |
| D909,564 S | 2/2021 | Bogan |
| D910,840 S | 2/2021 | Klenner et al. |
| D917,690 S | 4/2021 | Lau et al. |
| D923,169 S | 6/2021 | McCool et al. |
| D923,768 S | 6/2021 | Maeckelberghe et al. |
| D924,154 S | 7/2021 | Dykas et al. |
| D924,377 S | 7/2021 | Kwak et al. |
| D925,734 S | 7/2021 | Park |
| 11,052,236 B2 | 7/2021 | Gulliver et al. |
| D928,925 S | 8/2021 | Lei |
| D928,948 S | 8/2021 | Gulliver et al. |
| D928,949 S | 8/2021 | Gulliver et al. |
| D930,184 S | 9/2021 | Johnson |
| D933,815 S | 10/2021 | Eves et al. |
| D937,411 S | 11/2021 | Powell |
| D938,016 S | 12/2021 | Eves et al. |
| D940,861 S | 1/2022 | Mosen et al. |
| 11,224,728 B2 | 1/2022 | Ignon |
| D944,936 S | 3/2022 | Chaves et al. |
| D944,939 S | 3/2022 | Chaves |
| D947,133 S | 3/2022 | Byrne et al. |
| D948,027 S | 4/2022 | Babbage et al. |
| D949,294 S | 4/2022 | Chandler |
| D949,295 S | 4/2022 | Chaves |
| D958,968 S | 7/2022 | Hobbs |
| 11,446,462 B2 | 9/2022 | Holyoake et al. |
| D968,587 S | 11/2022 | Holyoake et al. |
| D970,721 S | 11/2022 | Ros Fabrega et al. |
| 11,504,099 B1 | 11/2022 | Smith et al. |
| D973,862 S | 12/2022 | How et al. |
| D973,887 S | 12/2022 | Rohde, II et al. |
| D974,551 S | 1/2023 | Mosen et al. |
| D975,839 S | 1/2023 | Kuo |
| D977,087 S | 1/2023 | Siew |
| D983,353 S | 4/2023 | Babbage et al. |
| D984,639 S | 4/2023 | Fang |
| D988,500 S | 6/2023 | Ishikawa |
| D995,758 S | 8/2023 | McDermott et al. |
| D1,006,981 S | 12/2023 | Berney et al. |
| D1,010,112 S | 1/2024 | Dadachanji |
| D1,013,860 S | 2/2024 | Luo |
| D1,017,020 S | 3/2024 | Holyoake |
| D1,019,340 S | 3/2024 | Gu |
| D1,026,221 S | 5/2024 | Mosen et al. |
| D1,027,165 S | 5/2024 | Lau et al. |
| D1,028,213 S | 5/2024 | Lau et al. |
| D1,037,433 S | 7/2024 | Babbage et al. |
| D1,039,134 S | 8/2024 | McDermott et al. |
| 2001/0004970 A1 | 6/2001 | Hollister |
| 2001/0029949 A1* | 10/2001 | Blackhurst ........ A61M 16/1055 128/205.27 |
| 2001/0031819 A1 | 10/2001 | Iwata et al. |
| 2002/0017302 A1 | 2/2002 | Fukunaga et al. |
| 2002/0112730 A1 | 8/2002 | Dutkiewicz |
| 2002/0149200 A1 | 10/2002 | Fumioka |
| 2002/0173748 A1 | 11/2002 | McConnell |
| 2003/0116963 A1 | 6/2003 | Teuscher et al. |
| 2003/0136932 A1 | 7/2003 | Doyle |
| 2004/0090066 A1 | 5/2004 | Hoffmann |
| 2004/0103686 A1 | 6/2004 | Fehr et al. |
| 2004/0108218 A1 | 6/2004 | Stubergh |
| 2004/0156915 A1 | 8/2004 | Harman et al. |
| 2004/0261797 A1* | 12/2004 | White ............... A61M 16/0003 128/206.11 |
| 2005/0011524 A1 | 1/2005 | Thomlinson et al. |
| 2005/0028822 A1 | 2/2005 | Sleeper et al. |
| 2005/0077726 A1 | 4/2005 | White et al. |
| 2005/0085794 A1 | 4/2005 | Denoth et al. |
| 2005/0188990 A1* | 9/2005 | Fukunaga ........... A61M 16/105 128/205.12 |
| 2005/0283114 A1 | 12/2005 | Bresina |
| 2006/0107958 A1 | 5/2006 | Sleeper |
| 2006/0107960 A1 | 5/2006 | Smart |
| 2006/0113690 A1 | 6/2006 | Huddart |
| 2006/0157056 A1 | 7/2006 | Burk |
| 2007/0043334 A1 | 2/2007 | Guala |
| 2007/0088327 A1 | 4/2007 | Guala |
| 2007/0163588 A1 | 7/2007 | Hebrank et al. |
| 2007/0169825 A1 | 7/2007 | Packham et al. |
| 2007/0175473 A1 | 8/2007 | Lewis et al. |
| 2007/0276356 A1 | 11/2007 | Downing et al. |
| 2008/0041391 A1 | 2/2008 | Worley |
| 2008/0093846 A1 | 4/2008 | Sparks et al. |
| 2008/0105257 A1 | 5/2008 | Klasek |
| 2008/0142019 A1 | 6/2008 | Lewis et al. |
| 2008/0183153 A1 | 7/2008 | Enns |
| 2008/0190436 A1 | 8/2008 | Jaffe et al. |
| 2008/0214990 A1 | 9/2008 | Smutney et al. |
| 2008/0236577 A1 | 10/2008 | Power |
| 2008/0264413 A1 | 10/2008 | Doherty |
| 2008/0287920 A1 | 11/2008 | Fangrow et al. |
| 2009/0101147 A1 | 4/2009 | Landis et al. |
| 2009/0120434 A1 | 5/2009 | Smith et al. |
| 2009/0223523 A1 | 9/2009 | Chang |
| 2009/0223963 A1 | 9/2009 | Bisio |
| 2009/0240178 A1 | 9/2009 | Hanlon et al. |
| 2009/0266357 A1 | 10/2009 | Varis et al. |
| 2009/0299158 A1 | 12/2009 | Boatner et al. |
| 2010/0043789 A1 | 2/2010 | Fine et al. |
| 2010/0116272 A1 | 5/2010 | Row et al. |
| 2010/0148500 A1 | 6/2010 | Uehara et al. |
| 2010/0163051 A1 | 7/2010 | Brewer et al. |
| 2010/0168600 A1 | 7/2010 | Adriance et al. |
| 2010/0192957 A1* | 8/2010 | Hobson ............ A61M 16/0672 128/207.18 |
| 2010/0206310 A1 | 8/2010 | Matsubara et al. |
| 2010/0242961 A1 | 9/2010 | Mougel et al. |
| 2011/0067704 A1 | 3/2011 | Kooij et al. |
| 2011/0071504 A1 | 3/2011 | Saltell et al. |
| 2011/0074148 A1 | 3/2011 | Imai |
| 2011/0120472 A1 | 5/2011 | Lee et al. |
| 2011/0139151 A1 | 6/2011 | Burns |
| 2011/0139826 A1 | 6/2011 | Hair |
| 2011/0148097 A1* | 6/2011 | Ping ................... A61M 16/08 285/125.1 |
| 2011/0162644 A1 | 7/2011 | Ujhazy et al. |
| 2011/0197341 A1 | 8/2011 | Formica et al. |
| 2011/0240031 A1 | 10/2011 | Jaffre |
| 2011/0253136 A1 | 10/2011 | Sweeney et al. |
| 2011/0265796 A1 | 11/2011 | Amarasinghe et al. |
| 2012/0157914 A1 | 6/2012 | Stroup |
| 2012/0247477 A1 | 10/2012 | Stephenson et al. |
| 2012/0305001 A1 | 12/2012 | Tatkov |
| 2013/0037030 A1 | 2/2013 | Matula |
| 2013/0104888 A1 | 5/2013 | Landis et al. |
| 2013/0133651 A1 | 5/2013 | Barker et al. |
| 2013/0167841 A1 | 7/2013 | Sheffer et al. |
| 2013/0220327 A1 | 8/2013 | Barlow et al. |
| 2013/0245611 A1 | 9/2013 | Bonnet et al. |
| 2013/0255670 A1 | 10/2013 | Ott et al. |
| 2013/0264821 A1 | 10/2013 | Duck |

(56) References Cited

U.S. PATENT DOCUMENTS

| | | |
|---|---|---|
| 2013/0284167 A1 | 10/2013 | Porteous et al. |
| 2013/0292592 A1 | 11/2013 | Py |
| 2014/0000626 A1 | 1/2014 | O'Connor et al. |
| 2014/0014108 A1 | 1/2014 | Dillard |
| 2014/0053846 A1 | 2/2014 | Wood |
| 2014/0144438 A1 | 5/2014 | Klasek |
| 2014/0158127 A1 | 6/2014 | Boucher et al. |
| 2014/0191501 A1 | 7/2014 | Brugger et al. |
| 2014/0200475 A1 | 7/2014 | Rubin |
| 2014/0238401 A1 | 8/2014 | Paschall |
| 2014/0261416 A1 | 9/2014 | Arcilla et al. |
| 2014/0338669 A1 | 11/2014 | Zhao et al. |
| 2014/0373841 A1 | 12/2014 | Nashed |
| 2015/0059745 A1 | 3/2015 | Barker et al. |
| 2015/0068519 A1* | 3/2015 | Bambrilla ............ A61M 16/206 128/204.25 |
| 2015/0083121 A1 | 3/2015 | Fisher |
| 2015/0128944 A1 | 5/2015 | Buechi |
| 2015/0167877 A1 | 6/2015 | Kendrick |
| 2015/0209568 A1 | 7/2015 | Rosenquist |
| 2015/0290416 A1 | 10/2015 | Klasek |
| 2015/0306332 A1* | 10/2015 | Bafile ............... A61M 16/0875 128/202.27 |
| 2015/0320949 A1 | 11/2015 | Jaffe |
| 2015/0320962 A1 | 11/2015 | Bafile et al. |
| 2016/0001031 A1 | 1/2016 | Laing et al. |
| 2016/0038701 A1 | 2/2016 | White et al. |
| 2016/0082218 A1 | 3/2016 | Lau |
| 2016/0106913 A1 | 4/2016 | Ng et al. |
| 2016/0131292 A1 | 5/2016 | Decker |
| 2016/0193440 A1 | 7/2016 | Sheffer et al. |
| 2016/0199634 A1 | 7/2016 | Gagliardoni et al. |
| 2016/0228668 A1 | 8/2016 | Martin |
| 2016/0287824 A1 | 10/2016 | Chang |
| 2016/0305574 A1 | 10/2016 | Burdge |
| 2017/0036007 A1 | 2/2017 | Hallisey et al. |
| 2017/0065788 A1 | 3/2017 | Chou |
| 2017/0065789 A1 | 3/2017 | Reed |
| 2017/0197055 A1 | 7/2017 | Moody |
| 2017/0333662 A1 | 11/2017 | Ovinsky et al. |
| 2017/0361051 A1 | 12/2017 | Eifler |
| 2018/0064901 A1 | 3/2018 | Colman |
| 2018/0085544 A1 | 3/2018 | Holyoake |
| 2018/0117270 A1 | 5/2018 | Bassin |
| 2018/0140819 A1 | 5/2018 | Yang |
| 2018/0200148 A1 | 7/2018 | Sanders |
| 2019/0022344 A1 | 1/2019 | Lau et al. |
| 2019/0151842 A1 | 5/2019 | Williams et al. |
| 2019/0167935 A1 | 6/2019 | Siew et al. |
| 2019/0381268 A1 | 12/2019 | Colman |
| 2020/0129724 A1 | 4/2020 | Nelson |
| 2021/0205589 A1 | 7/2021 | Dong |
| 2021/0322706 A1 | 10/2021 | Lau et al. |
| 2021/0361924 A1 | 11/2021 | Gulliver et al. |
| 2021/0402126 A1 | 12/2021 | Lau et al. |
| 2021/0402127 A1 | 12/2021 | Lau et al. |
| 2023/0021629 A1 | 1/2023 | Ranjitsingh |
| 2023/0381484 A1 | 11/2023 | Gulliver et al. |

FOREIGN PATENT DOCUMENTS

| | | |
|---|---|---|
| CN | 101365509 | 2/2009 |
| CN | 201775849 | 3/2011 |
| CN | 102019014 | 4/2011 |
| DE | 3709122 | 9/1988 |
| DE | 19615290 | 1/1998 |
| DE | 102007063556 | 7/2009 |
| EM | 000254420-0014 | 11/2004 |
| EM | 008110019-0001 | 9/2020 |
| EM | 008110019-0002 | 9/2020 |
| EM | 008569545-0001 | 6/2021 |
| EP | 1 068 889 | 1/2001 |
| EP | 1 181 945 | 2/2002 |
| EP | 0 809 768 | 7/2002 |
| EP | 1 277 488 | 1/2003 |
| EP | 1277488 A1 * | 1/2003 ........ A61M 16/0858 |
| EP | 1 314 446 | 5/2003 |
| EP | 1 403 838 | 3/2004 |
| EP | 1 408 313 | 4/2004 |
| EP | 1 479 405 | 11/2004 |
| EP | 1 481 702 | 12/2004 |
| EP | 1 520 599 | 4/2005 |
| EP | 1 023 912 B1 | 11/2005 |
| EP | 1 449 502 | 12/2007 |
| EP | 1 933 074 | 6/2018 |
| EP | 2 906 287 | 6/2019 |
| EP | 2 877 224 | 9/2020 |
| EP | 2 925 396 | 9/2020 |
| GB | 1563359 | 3/1980 |
| GB | 2328260 | 2/1999 |
| GB | 9004583508-0001 | 1/2018 |
| GB | 6179729 | 12/2021 |
| JP | 09-028806 | 2/1997 |
| JP | 2002-126094 | 5/2002 |
| JP | 2007-236567 | 9/2007 |
| JP | 2009-160031 | 7/2009 |
| JP | D1639030 | 8/2019 |
| JP | D1723039 | 8/2022 |
| JP | D1737290 | 2/2023 |
| KR | 1020040103139 | 12/2004 |
| MY | 13-1228-0303-0001 | 8/2014 |
| TW | 223055-0001 | 1/2023 |
| TW | 226455-0001 | 3/2023 |
| WO | WO 90/014122 | 11/1990 |
| WO | WO 94/004211 | 3/1994 |
| WO | WO 97/015376 | 5/1997 |
| WO | WO 97/48433 | 12/1997 |
| WO | WO 99/012598 | 3/1999 |
| WO | WO 03/090827 | 11/2002 |
| WO | WO 03/082406 | 10/2003 |
| WO | WO 04/108218 | 12/2004 |
| WO | WO 05/018524 | 3/2005 |
| WO | WO 05/079670 | 9/2005 |
| WO | WO 05/102431 | 11/2005 |
| WO | WO 07/019625 | 2/2007 |
| WO | WO 07/024812 | 3/2007 |
| WO | WO 08/144298 | 11/2008 |
| WO | WO 08/144447 | 11/2008 |
| WO | WO 09/094532 | 7/2009 |
| WO | WO 09/146484 | 12/2009 |
| WO | WO 11/062510 | 5/2011 |
| WO | WO 11/077254 | 6/2011 |
| WO | WO 11/079226 | 6/2011 |
| WO | WO 12/052903 | 4/2012 |
| WO | WO 13/022356 | 2/2013 |
| WO | WO 13/088439 | 6/2013 |
| WO | WO 13/127474 | 9/2013 |
| WO | WO 14/015382 | 1/2014 |
| WO | WO 14/025267 | 2/2014 |
| WO | WO 14/077706 | 5/2014 |
| WO | WO 14/097145 | 6/2014 |
| WO | WO 14/129912 | 8/2014 |
| WO | WO 2014/205513 | 12/2014 |
| WO | WO 15/038014 | 3/2015 |
| WO | WO 2015/142192 | 9/2015 |
| WO | WO 16/157101 | 10/2016 |
| WO | WO 16/157105 | 10/2016 |

OTHER PUBLICATIONS

AQR Safety Connection, Staubli, [Post date: Nov. 29, 2023], [Site seen Aug. 9, 2023], Seen at URL: https://www.staubli.com/fr/en/fluid-connectors/products/quick-and-dry-disconnect-couplings/breathing-air.html (Year: 2023).

Fisher & Paykel ICON ThermoSmart Heated CPAP Tubing, 6 Foot, Fisher & Paykel, [Post date unknown], [Site seen Mar. 23, 2023], Seen at URL: https://helpmedicalsupplies.com/products/6-thermosmart-heated-hose-tubing-for-f-p-icon-cpap-machine?variant=9981444522099 (Year: 2023), 1 p.

Prestan Rescue Mask Adapters 50 Pack, Prestan, heartsmart.com, [Post date: unknown], [Site seen Aug. 9, 2023], Seen at URL:+

(56) References Cited

OTHER PUBLICATIONS https://www.heartsmart.com/prestan-rescue-mask-adapters-p (Year: 2023).
Replacement Non-Heated Hose Tubing for Fisher & Paykel SleepStyle Auto CPAP Machine, Fisher & Paykel, .cpapstoreusa.com, [Post Date: Jun. 26, 2022], [Site seen Mar. 23, 2023], Seen at URL: https://www.cpapstoreusa.com/product/ replacement-non-heated-hose-tubing-for-fisher-paykel-sleepstyle-auto-cpap-machine/ (Year: 2022), 1 p.
Replacement Tube Assembly for WIS_P, IBEET Short Tube Supplies—Quick Release & 360-Degree Rotatable, IBEET, Amazon.com, [Post date: Oct. 28, 2021], Seen at URL: https://www.amazon.com/Replacement-Tube-Assembly-Short-Supplies/dp/ B09GM12TMG (Year: 2021), 4 pp.
Fisher & Paykel Healthcare Limited, Junior Tube and Chamber Kit brochure, 900PT531, 2012.
Huapa Mini hose connector for CPAP hose CPAP accessories Resmed air nasal masks, Amazon.com, first posted Oct. 9, 2018, https://amzn.to/3x62sdy, 8 pp.
JML Medical, Adaptor One Way Valve 220Dx221D w/Oxygen Stem, Teleflex, [Post date unknown], downloaded May 19, 2022, https://www.jmlmed.com/collections/respiratory-products/products/one-way-valve-by-teleflex, 2 pp.
New Leaf Home Medical, Pressure Line Adaptor for Ventilation Accessories, Medline, [Post date Unknown], downloaded May 19, 2022 https://newleafhomemedical.com/pressure-line-adaptor-for-ventilation-accessories/, 1 p.
Pall Corporation, Jun. 10, 2019, Multiple-Patient-Use Anesthesia Circuits, product description, 5 pp.
Photos of current commercial connector illustrated in reference 1, 3 pages.
RC Medical Incorporated, Hudson Dual Spray MDI Adaptor, CS/50, [Post date: Post date unknown], downloaded, May 19, 2022, https://www.rcmedical.com/viewProduct.cfm?productID=871, 1 p.
Salter Labs, "Air-Q Intubating Laryngeal Airways (ILA) The everyday airway that's ready for the unexpected."; Dec. 2018; 8 pages.
Actin.ca, Jan. 1, 2023, What are CPAP Connectors and Adapters?, https://www.actin.ca/s/stories/what-are-cpap-connectors-and-adapters, 3 pp.
Venture Respiratory, 2024, Adapter Pressure Line 22mm 0. D. X 22mm I.D. connections 50/cs Hudson RGI/Teleflex, downloaded on Jul. 19, 2024, https://ventureresp.com/pressure-line-adapter-50-cs-1642/.
Fisher & Paykel CPAP Oxygen/Pressure Port Titration Adaptor, 10 Pack, Fisher & Paykel, Post date Dec. 5, 2023, https://helpmedicalsupplies.com/products/fisher-paykel-cpap-oxygen-pressure-port-titration-adaptor-10-pack.

* cited by examiner

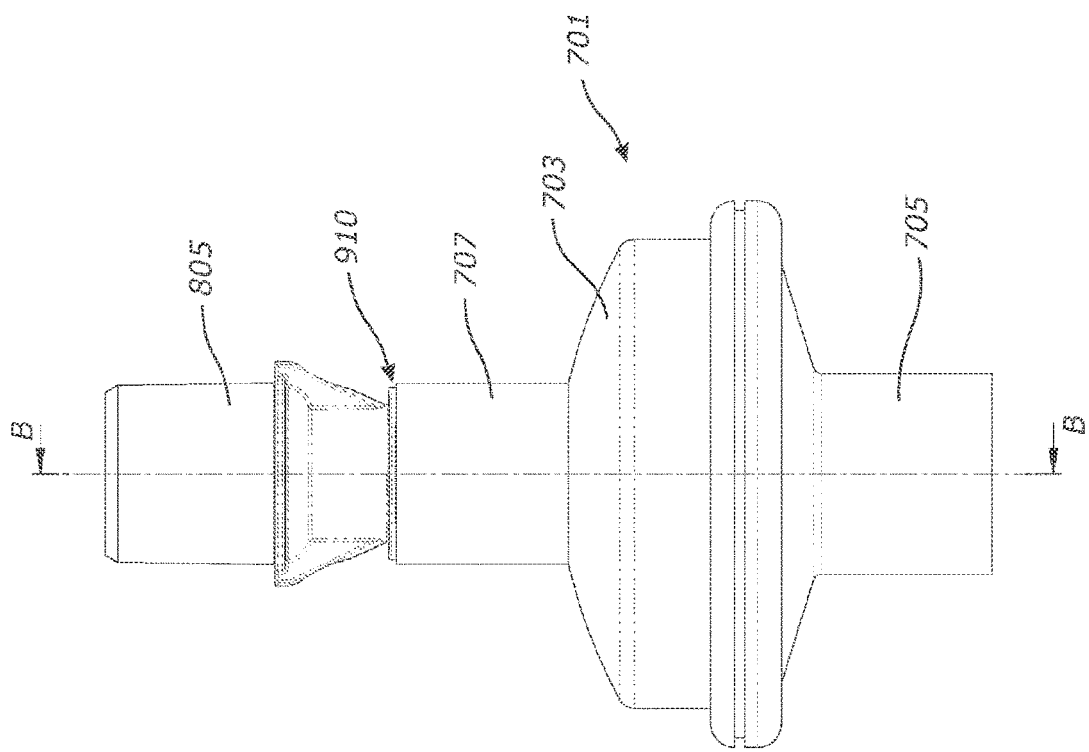
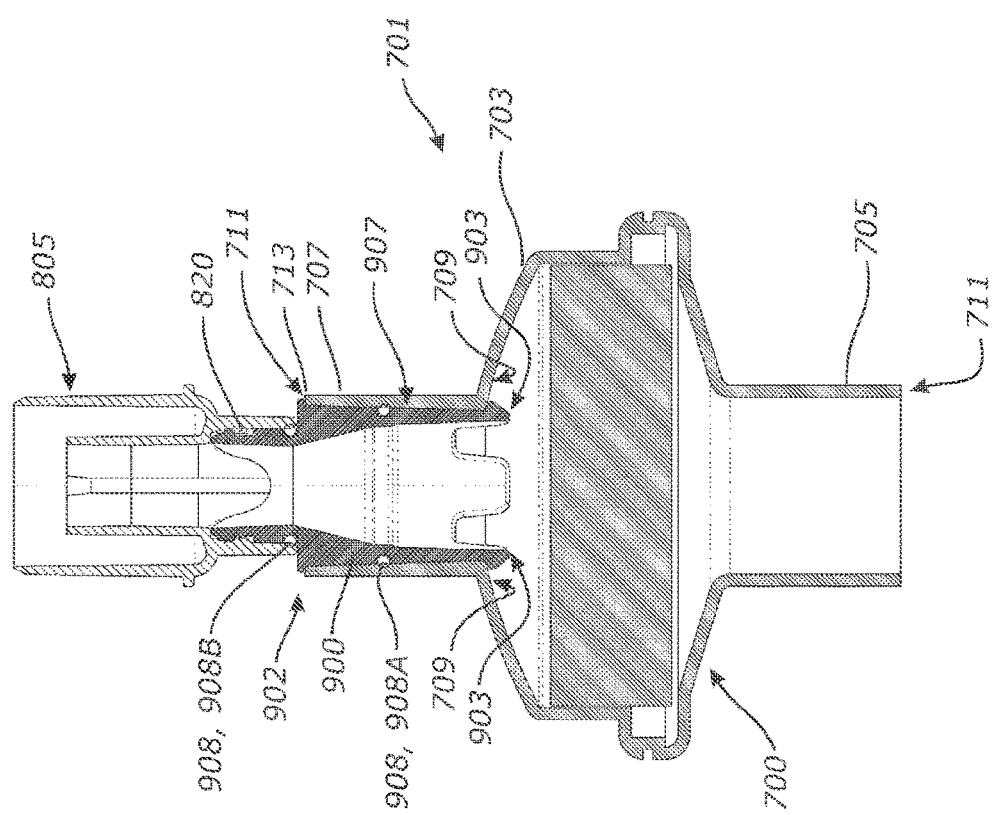
FIGURE 6F
FIGURE 6E

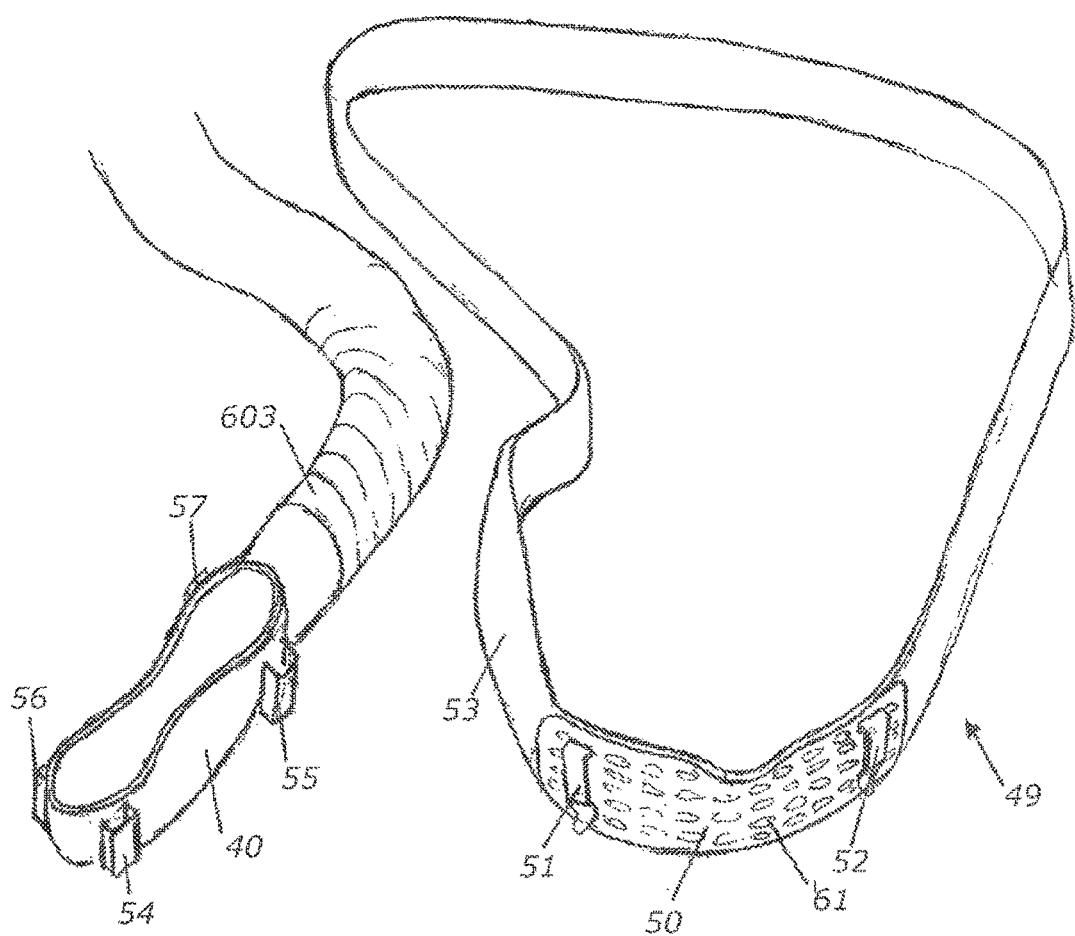
*FIGURE 13*     *FIGURE 14*
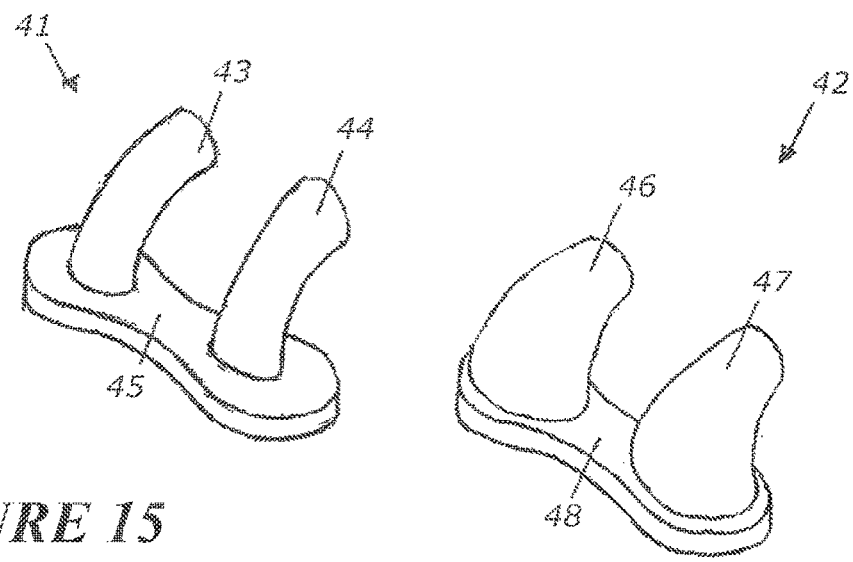
*FIGURE 15*     *FIGURE 16*

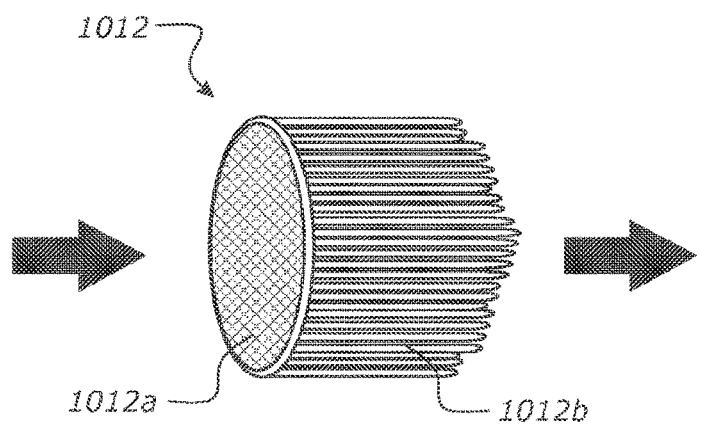
FIGURE 22E
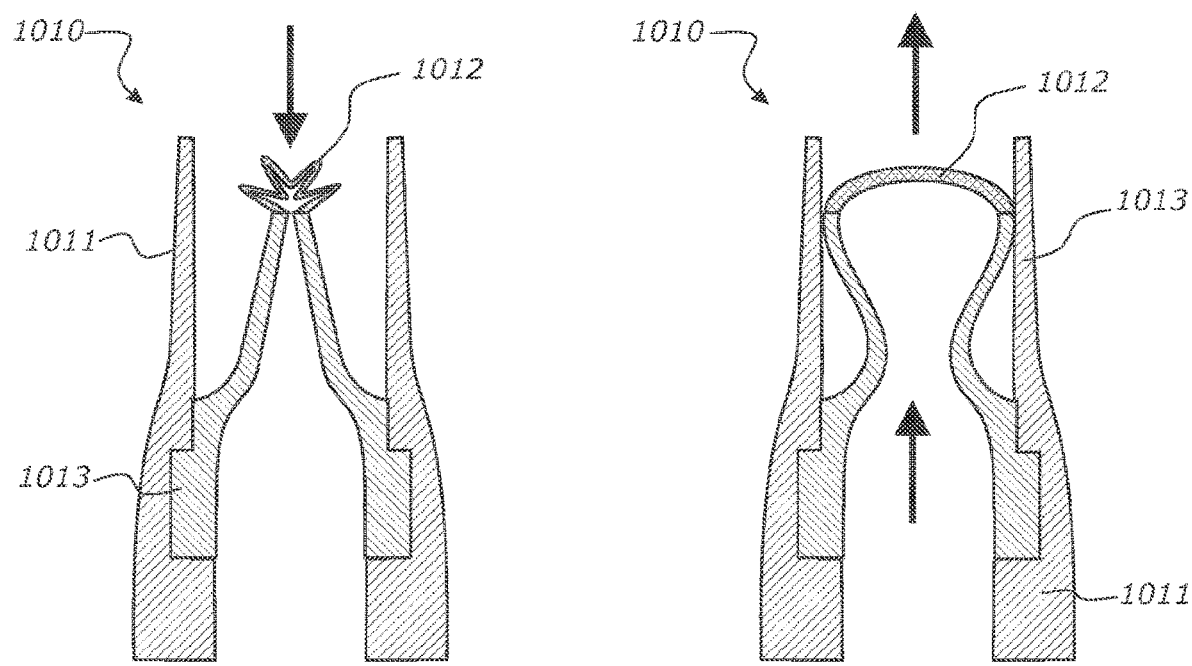
FIGURE 23A
FIGURE 23B

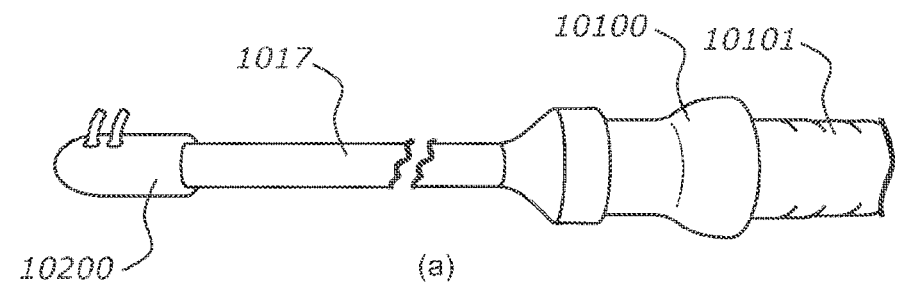
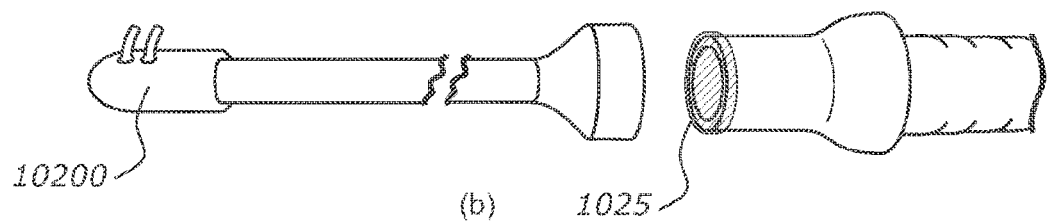
FIGURE 26A
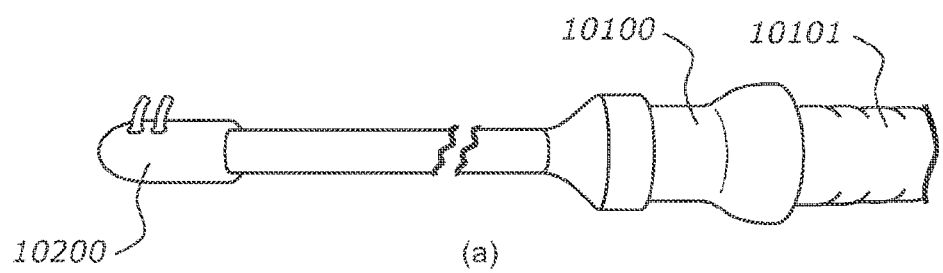
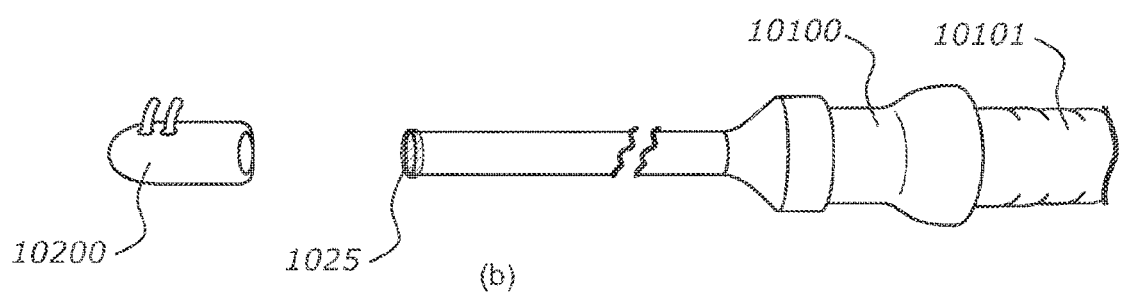
FIGURE 26B

APPARATUS FOR USE IN A RESPIRATORY SUPPORT SYSTEM

TECHNICAL FIELD

The present disclosure generally relates to methods and/or structures for preventing contamination of breathing circuits by patients, including but not limited to respiratory support kits or kits comprising respiratory support components to be used in providing respiratory support for patients receiving anaesthesia or undergoing intubation or endoscopy.

BACKGROUND

Patients may lose respiratory function during anaesthesia, or sedation, or more generally during certain medical procedures. Prior to a medical procedure a patient may be pre-oxygenated by a medical professional to provide a reservoir of oxygen saturation, and this pre-oxygenation is generally carried out with a bag and a face mask. Once under general anaesthesia, patients must be intubated to ventilate the patient. In some cases, intubation is completed in 30 to 60 seconds, but in other cases, particularly if the patient's airway is difficult to traverse (for example, due to cancer, severe injury, obesity or spasm of the neck muscles), intubation will take significantly longer. While pre-oxygenation provides a buffer against declines in oxygen saturation, for long intubation procedures, it is necessary to interrupt the intubation process and reapply the face mask to increase the patient's oxygen saturation to adequate levels. The interruption of the intubation process may happen several times for difficult intubation processes, which is time consuming and puts the patient at severe health risk. After approximately three attempts at intubation the medical procedure will be abandoned.

Respiratory therapy circuits are typically single use items. Once a therapy circuit, for example a respiratory gas conduit, has been used by a patient, the conduit together with a patient interface is thrown away. One of the reasons for this is to prevent contamination from one patient to another when the same flow source and/or humidifier are used.

Respiratory support systems that are used in multiple-patient environments typically require at least an inspiratory conduit and patient interface to be discarded and replaced between each patient to ensure the components provided for use by each patient are clean and not infected from prior users This is time consuming which may be detrimental in an emergency situation. It also creates significant amounts of waste and adds to the overall cost of the procedures or at least to the overall hospital operation costs since the hospital needs to keep a larger stock of inspiratory conduits. This cost can sometimes be passed on to the patient.

Humidity allows delivery of gas at high flow rates comfortably to patients so the gas flows can be used during the conscious patient preparation stage.

Reference to any prior art in this specification is not, and should not be taken as, an acknowledgement or any form of suggestion that that prior art forms part of the common general knowledge in the field of endeavour in any country in the world.

SUMMARY

It is an object of certain embodiments disclosed herein to provide a method or apparatus that might solve one or more of the above problems, or to at least provide the public with a useful choice.

It is an object of certain embodiments disclosed herein to provide an apparatus for use in a respiratory support system that will at least go some way towards improving on the above or which will at least provide the public or the medical profession with a useful choice. It is an alternative or additional object of certain embodiments disclosed herein to provide a kit for use in a respiratory support system that enables an inspiratory conduit to be re-used.

Humidified gases can be used to allow for the comfortable gases delivery during the sedated stages of a patient in some configurations. Humidity prevents or helps to minimise the airways from drying out and hence can prevent or minimise damage to the airways and may also improve or assist with maintaining patient comfort when receiving a flow of gases being delivery to their airway(s).

Thus, in accordance with at least one of the embodiments disclosed herein, an apparatus or kit for use in a respiratory support system for delivering humidified gas to a user or patient is disclosed. The apparatus or kit comprises:

a humidifier chamber that is in pneumatic communication with a gases source, or that is configured to be placed in pneumatic communication with the gases source;

an inspiratory conduit that is in pneumatic communication with the humidifier chamber downstream of the humidifier chamber, or that is configured to be placed in pneumatic communication with the humidifier chamber downstream of the humidifier chamber;

a filter that is in pneumatic communication with the inspiratory conduit downstream of the inspiratory conduit, or that is configured to be placed in pneumatic communication with the inspiratory conduit downstream of the inspiratory conduit; and a patient interface for delivering humidified gas to a user or patient, wherein the patient interface is in pneumatic communication with the filter downstream of the filter, or is configured to be placed in pneumatic communication with the filter downstream of the filter.

In the apparatus or kit, the filter may be coupled to the patient interface, or may be configured to be coupled to the patient interface. In the apparatus or kit, the patient interface may comprise a patient interface gases conduit, wherein the filter may comprise a gases inlet port and a gases outlet port, and wherein the gases outlet port of the filter and the patient interface gases conduit may comprise complementary coupling features to enable the filter to be coupled to the patient interface to provide pneumatic communication between the filter and the patient interface gases conduit, with the filter in-line with a gases flow path through the patient interface gases conduit. In the apparatus or kit, the complementary coupling features may be disconnectable from each other to enable the filter to be decoupled from the patient interface gases conduit.

The filter may be coupled to an interface tube, such as a patient interface gases conduit, that is coupled to the manifold. The patient interface gases conduit may be a short section of tube or conduit. For example, the patient interface gases conduit may be about 20 cm to about 50 cm long, or about 25 cm to about 40 cm long, or about 30 cm to about 35 cm long, or may be about 32 cm long.

In the apparatus or kit, the patient interface may comprise a patient interface gases conduit, wherein the filter may be integrated into the patient interface gases conduit to provide pneumatic communication between the filter and the patient interface gases conduit, with the filter in-line with a gases flow path through the patient interface gases conduit. Optionally, in such an arrangement, a gases inlet to such an integrated filter may comprise of complementary coupling features. Such complementary coupling features may for example be provided by an adapter insert attached to the gases inlet of such an integrated filter component.

With reference to the complementary coupling features as described herein, these features may optionally be provided by provision of an adapter insert to the item or component (for example, but not limited to, the gases inlet or gases outlet of: a filter, a conduit, gases inlet to a patient interface) requiring such complementary coupling features to enable a coupling and decoupling or connection and disconnection. Such an adapter insert is described elsewhere in this specification.

In the apparatus or kit, a gases inlet port of the filter and a gases outlet port of the inspiratory conduit may comprise complementary coupling features, to enable the inspiratory conduit to be coupled to the filter to provide pneumatic communication between the inspiratory conduit and the filter. In the apparatus or kit, the complementary coupling features of the gases inlet port of the filter and the gases outlet port of the inspiratory conduit may be disconnectable from each other to enable the inspiratory conduit to be decoupled from the filter.

In the apparatus or kit, a gases inlet port of the inspiratory conduit and a gases outlet port of the humidifier chamber may comprise complementary coupling features, to enable the inspiratory conduit to be coupled to the humidifier to provide pneumatic communication between the humidifier chamber and the inspiratory conduit. In the apparatus or kit, the complementary coupling features of the gases outlet of the humidifier chamber and the gases inlet of the inspiratory conduit may be disconnectable from each other to enable the inspiratory conduit to be decoupled from the humidifier chamber.

The apparatus or kit may further comprise a gases delivery conduit that is in pneumatic communication with the source of gas, or that is configured to be placed in pneumatic communication with the source of gas, wherein the humidifier chamber is in pneumatic communication with the gases delivery conduit downstream of the gases delivery conduit, or is configured to be placed in pneumatic communication with the gases delivery conduit downstream of the gases delivery conduit. In the apparatus or kit, a gases outlet port of the gases delivery conduit and a gases inlet port of the humidifier chamber may comprise complementary coupling features, the complementary coupling features being to enable the gases delivery conduit to be coupled to the humidifier to provide pneumatic communication between the humidifier chamber and the gases delivery conduit. In the apparatus or kit, the gases outlet port of the gases delivery conduit and the gases inlet port of the humidifier chamber comprise complementary coupling features, the complementary coupling features may be disconnectable from each other to enable the gases delivery conduit to be decoupled from the humidifier chamber.

In the apparatus or kit, the filter may be a high-efficiency particulate arrestance (HEPA) filter, a pleated sheet filter (such as of the type manufactured of glass micro fibres), nano fibre filter, sock filter, stacked disc filter, spiral filter, block of filter material, a disc of filter material with streams of filter material to free flow from or off the disc in fluid flow, ceramic type filter, fabricated material type filter (such as a woven wire cloth), porous plastic type filter (such as plastic powders moulded into porous rigid shape type filter), non-woven media type filter (such as dry-formed, wet-laid or membrane type filter).

The filter may contain filtration material.

The filtration material may comprises one or more of: pleated paper, nano fibres, cellulose, cotton, wood pulp, glass, fiberglass, glass micro fiber, or composites, polymers such as polytetrafluoroethylene (PTFE), polycarbonate (PC), acrylics including modacrylics, rayon, fluoropolymers, thermoplastic polyurethane (TPU), polyethylene (PE), polyamides, polyester, polypropylene (PP), nylon, metals such as galvanized steel, stainless steel, aluminium, copper.

The composites may consist of: polyamides, polyether sulfone, polysulfone, ceramic, carbon, polymers such as polytetrafluoroethylene (PTFE), polycarbonate (PC), acrylics, rayon, fluoropolymers, thermoplastic polyurethane (TPU), polyethylene (PE), polyamides, polyester, polypropylene (PP), nylon.

The filter or a filtration material of the filter may comprise: electrostatic, hydrophilic, hydrophobic characteristics or properties.

The patient interface may comprise a nasal cannula or a nasal mask, wherein the nasal cannula or nasal mask comprises at least one gases flow path that is in pneumatic communication with the filter, or that is configured to be placed in pneumatic communication with the filter when the filter is coupled to the patient interface. In some configurations, the nasal cannula comprises at least one nasal delivery element that extends from a flow manifold and that is adapted to rest in one or more nares of a user to deliver humidified gas to the user, whether in a sealing manner or a non-sealing manner.

The inspiratory conduit may comprise a heating element to heat humidified gases as they travel through the inspiratory tube.

The humidifier chamber may comprise a housing defining a liquid reservoir, a gases inlet port in pneumatic communication with the liquid reservoir, a gases outlet port in pneumatic communication with the liquid reservoir, and a base, wherein the base is arranged to be positioned on or above a heating element to heat liquid in the liquid reservoir, and wherein the gases inlet port, the liquid reservoir, and the gases outlet port provide a gases flow path from the gases inlet port, through or past the liquid reservoir, to the gases outlet port to humidify gases travelling along the gases flow path.

The inspiratory conduit may further comprise a component adapted to be engageable with said inspiratory conduit and to support said inspiratory component.

The inspiratory conduit may further comprises a component adapted to engage with said inspiratory conduit and provided with jaws extending from a body of the component, the jaws adapted to grip an item and thereby support said inspiratory component.

Optionally, the jaws may be a pair of opposing jaws for gripping of an item, such as a sheet or article of clothing or other item or article (e.g. a medical stand or component attached thereto).

The body of the component may substantially surround a perimeter of the conduit or tube upon which it is located.

The jaws of the component may be co-acting upon each other in a closed position.

The body comprises a shoulder portion associated with each jaw of the pair of jaws, the shoulder portion providing a surface for actuation, by a user.

The shoulder portion is an enlarged region of the body.

The shoulder portions are sized for actuation by fingers of a user, or are finger tabs.

The body is configured to be substantially annular about the exterior surface of the, or each, respective tube(s).

The component may be a tube clip capable of engaging with an exterior surface or surfaces of a conduit or tube, such as the inspiratory conduit, where the tube clip additionally comprises a pair of jaws adapted for gripping of an item, such that when the jaws of the tube clip grip an item, the conduit or tube may be supported.

The component may for example be that as described by PCT/NZ2012/000169 (published as WO2013/073970) the entirety of the contents of which is incorporated herein by reference.

The apparatus or kit may be provided as a kit.

Additionally, in accordance with certain features, aspects and advantages of at least one of the embodiments disclosed herein, there is provided the apparatus or kit as outlined in relation to the aspect above, when used to deliver humidified gas to a user or patient. In some applications, the patient is being anaesthetized and/or has been anaesthetized and is not breathing spontaneously. In some applications, the patient is being pre-oxygenated prior to being anaesthetized.

Additionally, in accordance with certain features, aspects and advantages of at least one of the embodiments disclosed herein, a package is disclosed. The package comprises a sealed container or bag that contains the apparatus or kit as outlined in relation to the aspect above.

The filter, the humidifier chamber, the inspiratory conduit, the gases delivery conduit and patient interface may be each provided separately in the package (i.e. not coupled or integrated). Alternatively, at least some of these may be provided in a coupled arrangement together in the package.

For example, a first kit may or package may comprise of "consumable" components, such as a gases delivery conduit (i.e. a conduit of the type that extends from a source of gas to the inlet of a humidifier chamber), a humidifier chamber, an inspiratory conduit (i.e. a conduit of the type extends from the outlet or downstream side of a humidifier chamber toward a patient interface), a tube clip (i.e. a component of the type that may be attached or attachable to a conduit, such as an inspiratory conduit to assist with supporting or locating the inspiratory conduit relative to an item), a filter, an adapter insert (i.e. to facilitate connection between components), and a patient interface (i.e. a patient interface of the type such as those described elsewhere in this specification, but which may comprise of a nasal cannula or a nasal mask). It will be appreciated the gases delivery conduit may be of the type referred to as a "dryline", as it is not downstream of a humidification device, such as a humidifier chamber, which provides humidity to the flow of gases being directed toward a patient interface for a patient.

For example, another kit or package may comprise of "patient" components, such "patient" components being provided for use with a single patient, and/or for a single use or procedure. "Patient components" being for example a patient interface and a filter for connection to such an interface. In another kit or package, the patient interface and the filter may be provided in an entirely different or separate package for sale on their own (e.g. a patient interface and filter sold together) or for providing this combination of components to the medical industry.

For example, yet another kit or package may comprise of those components required where a patient is not receiving a humidified gas, and as such, a humidifier chamber or a suitable downstream conduit of the type associated with delivering humidified gases is not required. Such a kit or package may comprise of a patient interface, a filter, and a conduit for delivering gas from a source of gas to the patient interface (such a conduit may be a gases delivery conduit or a non-heated inspiratory conduit).

The patient interface and filter may be provided separately in the package (i.e. not coupled or integrated). In some configurations, the patient interface and filter are coupled in the package, or the filter is integrated into the patient interface gases tube of the patient interface.

Additionally, in accordance with certain features, aspects and advantages of at least one of the embodiments disclosed herein, a method of assembling a breathing circuit is disclosed. The method comprises: providing the apparatus or kit or the package outlined in relation to the aspects above; positioning the inspiratory conduit downstream of the humidifier chamber, and positioning the filter and patient interface downstream of the inspiratory conduit.

The method may further comprise receiving gas at the humidifier from the source of gas, humidifying the gas, receiving humidified gas at the filter from the humidifier, and delivering the humidified gas from the filter to the patient interface.

The method may further comprise positioning the gases delivery conduit upstream of the humidifier chamber and downstream of the source of gas, prior to receiving gas at the humidifier from the source of gas.

The method may further comprise coupling the filter to the patient interface, prior to delivering the humidified gas from the filter to the patient interface.

In some applications, the method further comprises decoupling the filter from the humidifier. In some applications, the method further comprises operatively coupling the filter to another source of gas.

The method may further comprise, after decoupling the filter from the humidifier, providing a further apparatus or kit comprising a patient interface for delivering humidified gas to a patient and a filter that is in pneumatic communication with the patient interface or that is configured to be placed in pneumatic communication with the patient interface; and positioning the filter and patient interface of the further apparatus downstream of the humidifier.

The method may further comprise receiving humidified gas at the filter from the humidifier and delivering the humidified gas from the filter to the patient interface.

Additionally, in accordance with certain features, aspects and advantages of at least one of the embodiments disclosed herein, a method of delivering gas to a user or patient is disclosed. The method comprises: providing a breathing circuit comprising a source of gas and the apparatus or kit as outlined in relation the aspect above or the package as outlined in relation to the aspect above, and configuring the breathing circuit such that the humidifier receives gas from a source of gas, the inspiratory conduit is positioned downstream of the humidifier and delivers humidified gas from the humidifier to the filter, and the patient interface is positioned downstream of the filter and receives humidified gas from the filter and delivers humidified gas to the user or patient.

The method may further comprise positioning the gases conduit downstream of the source of gas to deliver gas from the source of gas to the humidifier to humidify the gas.

In some applications, the patient is not breathing spontaneously and has been anaesthetized. In some applications, the patient is being pre-oxygenated prior to being anaesthetized.

Additionally, in accordance with certain features, aspects and advantages of at least one of the embodiments disclosed herein, an apparatus or kit for use in a respiratory support system for delivering humidified gas to a user or patient is disclosed. The apparatus or kit comprises:

a filter that is positioned downstream of a humidifier to receive humidified gas from the humidifier, or that is configured to be positioned downstream of a humidifier to receive humidified gas from the humidifier; and a patient interface for delivering humidified gas to a user or patient, wherein the patient interface is in pneumatic communication with the filter downstream of the filter, or is configured to be placed in pneumatic communication with the filter downstream of the filter, wherein a gases inlet or a gases outlet or both the gases inlet and gases outlet of the filter, comprise coupling features enabling the filter to be coupled and decoupled from an arrangement in which the filter is placed in pneumatic communication with said patient interface.

The filter may be coupled to the patient interface, or may be configured to be coupled to the patient interface.

The patient interface may comprise a patient interface gases tube, wherein the filter comprises a gases inlet port and a gases outlet port, and wherein the gases outlet port of the filter and the patient interface gases tube comprise complementary coupling features to enable the filter to be coupled to the patient interface to provide pneumatic communication between the filter and the patient interface gases tube, with the filter in-line with a gases flow path through the patient interface gases tube.

The complementary coupling features may be disconnectable from each other to enable the filter to be decoupled from the patient interface gases tube of the patient interface.

The patient interface may comprise a patient interface gases tube, wherein the filter is integrated into the patient interface gases tube to provide pneumatic communication between the filter and the patient interface gases tube, with the filter in-line with a gases flow path through the patient interface gases. Optionally, in such an arrangement, a gases inlet to such an integrated filter may comprise of complementary coupling features. Such complementary coupling features may for example be provided by an adapter insert attached to the gases inlet of such an integrated filter component.

The filter may be a high-efficiency particulate arrestance (HEPA) filter.

The filter may comprise a filter housing containing filtration material. The filtration material may comprise pleated paper, nano fibres, sock filter, stacked disc filter, spiral filter, block of filter material, a disc of filter material with streams of filter material to free flow from or off the disc in fluid flow.

The patient interface may comprise a nasal cannula or nasal mask, wherein the nasal cannula or nasal mask comprises at least one gases flow path that is in pneumatic communication with the filter, or that is configured to be placed in pneumatic communication with the filter when the filter is coupled to the patient interface. The nasal cannula may comprise at least one nasal delivery element that extends from a flow manifold and that is adapted to rest in one or more nares of a user to deliver humidified gas to the user, whether in a sealing manner or a non-sealing manner.

The apparatus or kit may be provided as a kit.

Additionally, in accordance with certain features, aspects and advantages of at least one of the embodiments disclosed herein, there is provided the apparatus or kit as outlined in relation to the aspect above, when used to deliver humidified gas to a user or patient. In some applications, the patient is being anaesthetized and/or has been anaesthetized and is not breathing spontaneously. In some applications, the patient is being pre-oxygenated prior to being anaesthetized.

Additionally, in accordance with certain features, aspects and advantages of at least one of the embodiments disclosed herein, a package is disclosed. The package comprises a sealed container or bag that contains the apparatus or kit as outlined in relation to the aspect above.

The patient interface and filter m provided separately in the package.

The patient interface and filter may be coupled in the package, or wherein the filter is integrated into with the patient interface gases tube.

Additionally, in accordance with certain features, aspects and advantages of at least one of the embodiments disclosed herein, a method of assembling a breathing circuit is disclosed. The method comprises providing the apparatus or kit as outlined in relation to the aspect above or the package as outlined in relation to the aspect above; and positioning the filter and patient interface downstream of a humidifier.

The method may further comprise receiving humidified gas at the filter from the humidifier and delivering the humidified gas from the filter to the patient interface.

The method may further comprise coupling the filter to the patient interface, prior to delivering the humidified gas from the filter to the patient interface.

The method may comprise decoupling the filter from the humidifier. In some applications, the method further comprises operatively coupling the filter to another source of gas.

The method may comprise after decoupling the filter from the humidifier, providing a further apparatus or kit or package as outlined in relation to the aspects above; and positioning the filter and patient interface of the further apparatus downstream of the humidifier.

The method may further comprise receiving humidified gas at the filter from the humidifier and delivering the humidified gas from the filter to the patient interface.

Additionally, in accordance with certain features, aspects and advantages of at least one of the embodiments disclosed herein, a method of delivering gas to a user or patient is disclosed. The method comprises: providing a breathing circuit comprising a source of gas, a humidifier that receives gas downstream from the source of gas, and the apparatus or kit or the package as outlined in relation to the aspects above, and configuring the breathing circuit such that the filter is positioned downstream of the humidifier and receives humidified gas from the humidifier, and the patient interface is positioned downstream of the filter and receives humidified gas from the filter and delivers humidified gas to the user or patient.

In some applications, the patient is not breathing spontaneously and has been anaesthetized. In some applications, the patient is being pre-oxygenated prior to being anaesthetized.

Additionally, in accordance with certain features, aspects and advantages of at least one of the embodiments disclosed herein, a respiratory support system is disclosed. The respiratory support system comprises either:

an inspiratory conduit having an inlet port and an outlet port, the inlet port being configured to receive gas from a source of gas; a filter having an inlet port and an outlet port, wherein the inlet port of the filter is coupled to the outlet port of the inspiratory conduit such that the filter is in pneumatic communication with the inspiratory conduit; and a patient interface, the patient interface comprising a patient conduit and a nasal cannula or a nasal mask for delivering gas to a patient, wherein the patient interface, is in pneumatic communication with the outlet port of the filter to receive gas from the outlet port of the filter, or a single inspiratory conduit having an inlet port and an outlet port, the single inspiratory conduit providing for a flow of gas for delivery to a patient interface, the inlet port being configured to receive the flow of gas from a source of gas; a common filter having an inlet port and an outlet port, wherein the inlet port of the common filter is coupled to the outlet port of the single inspiratory conduit such that the common filter is in pneumatic communication with the single inspiratory conduit, and wherein the common filter received the flow of gas from the single inspiratory conduit; and a patient interface, the patient interface comprising a patient conduit and a nasal cannula or a nasal mask for delivering gas to filtered by the common filter to a patient, wherein the patient interface is in pneumatic communication with the outlet port of the common filter to receive gas from the outlet port of the common filter.

The filter may be in-line between the outlet port of the inspiratory conduit and the patient conduit, or the common filter is in-line between the outlet port of the single inspiratory conduit and the patient conduit.

In this specification, where an inspiratory conduit may be provided or reference is made thereto, such an inspiratory conduit may be a single inspiratory conduit. Such an inspiratory conduit providing for a flow of gas for delivery to a patient interface.

In this specification, where a filter may be provided or reference is made thereto, such a filter may be a common filter for filtering the flow of gas supplied from an inspiratory conduit. Such a common filter receives the flow of gas from an inspiratory conduit, such as a single inspiratory conduit. Accordingly, the gas delivered to the patient interface is provided from the common filter.

The patient conduit may comprise a patient interface gases conduit, wherein the filter (e.g. a common filter) is in-line with the patient interface gases conduit.

The inlet port of the inspiratory conduit (e.g. being a single inspiratory conduit) may be configured to receive humidified gas from a humidifier.

Additionally, in accordance with certain features, aspects and advantages of at least one of the embodiments disclosed herein, a kit for use in a respiratory support system for delivering humidified gas to a user or patient is disclosed, The kit comprises: a humidifier chamber that is configured to be placed in pneumatic communication with a gases source;
  an inspiratory conduit that is in pneumatic communication with the humidifier chamber downstream of the humidifier chamber, or that is configured to be placed in pneumatic communication with the humidifier chamber downstream of the humidifier chamber;
  a filter that is in pneumatic communication with the inspiratory conduit downstream of the inspiratory conduit, or that is configured to be placed in pneumatic communication with the inspiratory conduit downstream of the inspiratory conduit; and
  a patient interface for delivering humidified gas to a user or patient, wherein the patient interface is in pneumatic communication with the filter downstream of the filter, or is configured to be placed in pneumatic communication with the filter downstream of the filter.

The filter may be integrated into the patient interface. Optionally, in such embodiments, an adapter insert may be provided to a gases inlet of the filter, such an adapter insert may for example be of the type described elsewhere in this specification.

The kit may further comprise a gases delivery conduit that is configured to be placed in pneumatic communication with the source of gas, wherein the humidifier chamber is in pneumatic communication with the gases delivery conduit downstream of the gases delivery conduit, or is configured to be placed in pneumatic communication with the gases delivery conduit downstream of the gases delivery conduit.

At least some of the components of the kit may be provided separately in the kit.

Additionally, in accordance with certain features, aspects and advantages of at least one of the embodiments disclosed herein, a kit for use in a respiratory support system for delivering humidified gas to a user or patient is disclosed. The kit comprises:
  a filter that is configured to be positioned downstream of a humidifier to receive humidified gas from the humidifier; and
  a patient interface for delivering humidified gas to a patient, wherein the patient interface is in pneumatic communication with the filter downstream of the filter, or is configured to be placed in pneumatic communication with the filter downstream of the filter.

The filter may be integrated into the patient interface.

Additionally, in accordance with certain features, aspects and advantages of at least one of the embodiments disclosed herein, an apparatus or kit for use in a respiratory support system for delivering humidified gas to a user or patient is disclosed, the apparatus or kit comprising:
  a gases delivery conduit that is in pneumatic communication with a source of gas, or that is configured to be placed in pneumatic communication with the source of gas;
  a humidifier chamber that is in pneumatic communication with the gases delivery conduit downstream of the gases delivery conduit, or that is configured to be placed in pneumatic communication with the gases delivery conduit downstream of the gases delivery conduit; and
  an inspiratory conduit that is in pneumatic communication with the humidifier chamber downstream of the humidifier chamber, or that is configured to be placed in pneumatic communication with the humidifier chamber downstream of the humidifier chamber.

Additionally, in accordance with certain features, aspects and advantages of at least one of the embodiments disclosed herein, a kit for use in a respiratory support system for delivering humidified gas to a user or patient is disclosed, the kit comprising:
  a gases delivery conduit that is configured to be placed in pneumatic communication with a source of gas;
  a humidifier chamber that is in pneumatic communication with the gases delivery conduit downstream of the gases delivery conduit, or that is configured to be placed in pneumatic communication with the gases delivery conduit downstream of the gases delivery conduit; and
  an inspiratory conduit that is in pneumatic communication with the humidifier chamber downstream of the humidifier chamber, or that is configured to be placed in pneumatic communication with the humidifier chamber downstream of the humidifier chamber.

The apparatus or kit, the package, the respiratory support system, or the kit, may be configured for use in anaesthetic procedures or procedures wherein a patient's respiratory drive is compromised or reduced.

Each apparatus or kit may be provided on its own or together. Different types of kits may be provided together or separately. For example, a single package may be provided with two or more of the kits of the same or different types therein.

Additionally, either provided independently or in accordance with certain features, aspects and advantages of at least one of the embodiments disclosed herein, there is provided a filter arrangement.

The filter arrangement may comprise a filter housing, the filter housing comprising a gases inlet port and a gases outlet port, wherein at least one (or both) of said inlet and/or outlet port(s) is adapted for connection with another component (such as a connector provided at a terminal end of a conduit) via one or more, preferably at least a pair, of male connection fingers extending externally therefrom. Optionally, such male connection fingers may provide for a part of a complementary coupling.

The male connection fingers may be configured to extend from said gases outlet port. Optionally, or alternatively, said male connection fingers may be configured to extend from said gases inlet port.

One or each of said gases inlet port or gases outlet port may comprise an adapter insert, said adapter insert configured to facilitate said connection with said another component.

The adapter insert may comprise said male connection fingers extending from a first end of the adapter insert.

The adapter insert may comprise one or more retention members, each said retention member substantially engageable with an interior surface portion of the filter housing.

Each retention member may be configured for an engagement with an interior surface of the filter housing to retain said adapter insert within a said port into which said adapter is inserted.

Each said retention member may be configured to resist axial displacement of said adapter in a direction toward an exterior end of a said port.

Each said retention member may comprise at least a hook or other surface projection (e.g. such as a radially outwardly extending ledge) to engage or latch with an internal surface of said filter housing.

The or each retention member may retain said adapter insert within a said port of the filter housing.

There may be four retention members, or there may be two retention members, or there may be a plurality of retention members.

Where there is provided more than one retention member, said retention members may be are arranged to form an array about an interior surface of the filter housing.

The adapter insert may comprise of a first end from which said male connection fingers extend, a second end from which the one or more retention members extend, and a shank portion connecting of the first end with the second end.

The shank portion may comprise a lumen or gas flow path for the passage of gases therethrough between each of the first end and second end.

The shank portion may be substantially housed within a said port into which said adapter insert is to be inserted.

The adapter insert may comprise one or more sealing members.

The adapter insert may comprise two or more sealing members.

The adapter insert may comprise two sealing members.

The adapter insert may comprises at least a first sealing member provided about the shank portion and at least a second sealing member provided substantially at or adjacent with a first end of the adapter insert.

At least one first sealing member may be provided about the shank portion.

The or a first sealing member may be provided about a circumference of the shank portion.

The or each said first sealing member may be configured to provide a first sealing surface extending radially outwardly from the shank portion.

The or each said first sealing member may be configured to provide a first sealing surface for sealing with an internal surface of a said port of the filter housing.

The or each said first sealing member may be located intermediate of a first end and a second end of the adapter insert.

At least one second sealing member may be provided substantially at or adjacent with a first end of the adapter insert.

The at least one second sealing member may be located substantially at or adjacent with a base of the male connection fingers as said male connection fingers extend from a first end of the adapter insert.

The first end of the adapter insert may comprise a radially extensive ledge or lip.

The at least one second sealing member may be located substantially upon an upper-side surface of the ledge or lip.

The ledge or lip may extend radially outwardly so as to have an outside diameter that is equal to or less than the outside diameter of a said port within which said adapter insert is to be located. Advantageously, the ledge or lip may be of an outside diameter that is greater than an inside diameter of a said port within which said adapter insert is to be located.

An underside surface of said ledge or lip may contact a terminal end face of a said port within which said adapter insert is to be located.

A distance between an underside surface of the ledge or lip and a retaining member may match or may be substantially equal to a length of a said port from said adapter insert into which said adapter insert is to be located.

The ledge or lip may be interposed or may be sandwiched between an end of the shank portion and a first end of the adapter insert.

The ledge or lip may be sandwiched between a base of said male connection fingers and an end of the shank portion.

The at least one second sealing member may be sandwiched between a base of said male connection fingers and an end of the shank portion.

The at least one second sealing member may be sandwiched between a base of said male connection fingers and an upper-side surface of the ledge or lip.

The at least one second sealing member may provide for a second sealing surface for sealing with a surface of another component (such as another connector) brought to bear upon said second sealing surface. Optionally, said another component (such as another connector) may be brought into connection or engagement with said male connection fingers and, in use, when such a connection or engagement is made, said another component may additionally engage with said second sealing member and said second sealing surface may be configured to operatively assist with a pneumatic connection between said adapter insert and said another component.

Either or both of the first and second sealing members may be an O-ring.

One or more splines or ribs may be located about the shank portion.

The one or more splines or ribs may extend longitudinally along the shank portion.

The one or more splines or ribs may extend a radial distance outward from the shank portion so as to at least partially engage or make surface contact with an inside surface of a said port into which said adapter insert is to be located.

One or each of the one or more splines or ribs may be configured to provide strengthening or structural support of a wall of a said port into which said adapter insert is to be located.

Exclusive of the first sealing member(s), said adapter insert may have a maximum radial outside diameter of equal to or less than 22 mm.

The lumen or gas flow path may transition from a substantially wider bore (or larger internal diameter) at a second end of the adapter insert to a substantially narrower bore (or a smaller internal diameter) at a first end of the adapter insert.

The lumen or gas flow path transition may be a substantially graduated, or a substantially linear, progression between the different bores or internal diameters between end of the first and second ends.

The adapter insert may be a retro-fittable piece, locatable with or insertable to a component to facilitate provision of the male connection fingers as a connecting system or connector for the component to which the adapter is inserted or located therewith.

Additionally, either provided independently or in accordance with at least one of the other embodiments disclosed herein, an adapter insert is disclosed.

The adapter insert comprises one or more (but may be at least a pair of), male connection fingers configured for connection or engagement with another connector, and one or more retention members, each said retention member to be substantially engageable with an interior surface portion of a body of a component into which said adapter insert is to be located.

The adapter insert may be configured to be located within a gases inlet port or a gases outlet port of a component, such as a connector provided at an end of a conduit or an inlet or outlet from another component such as, but not limited to, a humidifier or a flow source generator.

An off-the-shelf type filter may be adapted by insertion of the adapter insert as described in this specification. Retention members of the adapter insert facilitate an intended retention of the adapter insert in an inserted location with respect to a port (whether as an inlet or an outlet port) of such a filter.

Where a component has a gases inlet port or a gases outlet port, such a port may comprise the adapter insert, said adapter insert configured to facilitate engagement or connection with another component (e.g. a filter).

Optionally, the filter or a filter arrangement comprises a filter housing, the filter housing comprising a gases inlet port and a gases outlet port, wherein at least one (or both) of said inlet and/or outlet port(s) is adapted for connection with another component (such as a connector provided at a terminal end of a conduit) via said male connection fingers of said adapter insert, when said adapter insert is located within a said port.

The male connection fingers of the adapter insert may be configured to extend (externally therefrom) from a gases outlet port or gases inlet port of a said component.

The male connection fingers may extend from a first end of the adapter insert.

Each said retention member may be configured to be substantially engageable with an interior surface portion of said component into which said adapter insert is to be located.

Each retention member may be configured for an engagement with an interior surface of the component to retain said adapter insert within a said port into which said adapter insert is to be inserted.

Each said retention member may resist axial displacement of said adapter insert in a direction toward an exterior end of a said port of said component (e.g. said retention members help to resist an unintended disconnection of the adapter insert from a component to which it is or has been inserted or located thereto).

Each said retention member may be configured to internally locate said adapter insert into an internally anchored position within a said component.

Each said retention member may comprise at least a hook or other surface projection (e.g. such as a radially outwardly extending ledge) to engage or latch with an internal surface of a said component.

The or each retention member may retain said adapter insert within a said port of a said component.

There may be four retention members, or there may be two retention members, or there may be one, or there may be a plurality of retention members.

Where more than one retention members are provided, at least some of said retention members may be arranged to form an array about an interior surface of a said component.

The adapter insert may comprise of a first end from which said male connection fingers extend, a second end from which the one or more retention members extend, and a shank portion connecting of the first end with the second end.

The shank portion may comprise a lumen or gas flow path for the passage of gases therethrough between each of the first end and second end.

The shank portion may be substantially housed within a said port of a component into which said adapter insert is to be inserted.

The adapter insert may comprise one or more sealing members.

The adapter insert may comprise two or more sealing members.

The adapter insert may comprise two sealing members.

The adapter insert may comprise at least a first sealing member provided about the shank portion and at least a second sealing member provided substantially at or adjacent with a first end of the adapter insert.

At least one first sealing member may be provided about the shank portion.

The or a first sealing member may be provided about a circumference of the shank portion.

The or each said first sealing member may be configured to provide a first sealing surface extending radially outwardly from the shank portion.

The or each said first sealing member may be configured to provide a first sealing surface for sealing with an internal surface of a said port of a component.

The or each said first sealing member may be located intermediate of a first end and a second end of the adapter insert.

At least one second sealing member may be provided substantially at or adjacent with a first end of the adapter insert.

The at least one second sealing member may be located substantially at or adjacent with a base of the male connection fingers as said male connection fingers extend from a first end of the adapter insert.

The first end of the adapter insert may comprise a radially extensive ledge or lip.

The at least one second sealing member may be located substantially upon an upper-side surface of the ledge or lip.

The ledge or lip may extend radially outwardly so as to have an outside diameter that is equal to or less than the outside diameter of a said port of a component within which said adapter insert is to be located. Advantageously, the ledge or lip may be of an outside diameter that is greater than an inside diameter of a said port of a component within which said adapter insert is to be located.

An underside surface of said ledge or lip may contact a terminal end face of a said port of a component within which said adapter insert is to be located.

A distance between an underside surface of the ledge or lip and a retaining member may matches or may be substantially equal to a length of a said port of a component from said adapter insert is to be located.

The ledge or lip may be interposed or is sandwiched between an end of the shank portion and a first end of the adapter insert.

The ledge or lip may be sandwiched between a base of said male connection fingers and an end of the shank portion.

The at least one second sealing member may be sandwiched between a base of said male connection fingers and an end of the shank portion.

The at least one second sealing member may be sandwiched between a base of said male connection fingers and an upper-side surface of the ledge or lip.

The at least one second sealing member may provide for a second sealing surface for sealing with a surface of another component (such as another connector) brought to bear upon said second sealing surface. Optionally, said another component (such as another connector) may be brought into connection or engagement with said male connection fingers and, in use, when such a connection or engagement is made, said another component may additionally engage with said second sealing member and said second sealing surface may be configured to operatively assist with a pneumatic connection between said adapter insert and said another component.

Either or both of the first and second sealing members may be an O-ring.

One or more splines or ribs may be located about the shank portion.

The one or more splines or ribs may extend longitudinally along the shank portion.

The one or more splines or ribs may extend a radial distance outward from the shank portion so as to at least partially engage or make surface contact with an inside surface of a said port of a component into which said adapter insert is to be located.

One or each of the one or more splines or ribs may be configured to provide strengthening or structural support of a wall of a said port of a component into which said adapter insert is to be located.

Exclusive of the first sealing member(s), said adapter insert may have a maximum radial outside diameter of equal to or less than 22 mm.

The lumen or gas flow path may transition from a substantially wider bore (or larger internal diameter) at a second end of the adapter insert to a substantially narrower bore (or a smaller internal diameter) at a first end of the adapter insert.

The lumen or gas flow path transition may be a substantially graduated, or a substantially linear, progression between the different bores or internal diameters between end of the first and second ends.

The component as referred to above may be a filter, for example a filter as previously defined herein.

The another component may be a connector provided as a part of another section of a medical breathing circuit or a respiratory system.

According to any one or more of the embodiments described herein, the following additional features may be provided:

For example, where reference is made to a patient interface, such an interface may be a nasal cannula or a nasal mask.

For example, the apparatus described herein may be provided as a part of a system that comprises a gas supply which may be coupled to the apparatus to supply gas to a patient interface or other components associated with a breathing circuit or respiratory therapy system.

The gas supply may be configured to supply gas to a humidifier at a flow rate of between about 5 liters per minute (LPM) and about 120 LPM, or up to about 150 LPM, or at a flow rate of between about 50 LPM and about 80 LPM, or at a flow rate of about 70 LPM. In some configurations, the humidifier may be configured to supply gas to a patient interface with a humidity of about 44 mg/l.

The humidifier may be configured to supply gas to the patient interface with a temperature of about 37° C.

According to the various configurations or embodiments as disclosed in this specification, the patient interface may be a nasal cannula type or nasal mask type interface comprising a gas delivery component in the form of a manifold, the manifold being removably attachable to the body of the nasal cannula or nasal mask.

The removably attachable manifold may allow for a side swapping of the gas delivery conduit supply gas to the patient interface. The manifold may be of a push-fit type arrangement or may be connected to the body, yet disconnectable so as to allow for a swivelling or rotation of the manifold relative to the body for a re-orientation of the manifold and an associated gas supply conduit.

A patient interface which may be utilised according to the various embodiments described in this disclosure may be of the type that utilise a headgear comprising of at least one strap, such as a strap including a bifurcatable section or zone (i.e. a line of weakness or other pre-determined region able to be split by a user).

The tubing, which also may also be referred to herein as a conduit, or tubing or conduit circuits described herein is or are in the preferred form made of medical tubing or medical grade tubing suitable for use in medical procedures and/or as a part of a breathing circuit or respiratory therapy circuit.

The adapter insert as described herein may be utilised in combination with the filter as described elsewhere in this specification (e.g. the gas inlet or outlet of a filter), or for an adaptation to the terminal end of a conduit, for example with a connector provided at such a terminal end of a conduit. The adapter insert may facilitate connection by other components to a filter or a conduit which otherwise were not provided with a suitably configured connector. Accordingly, the insert allows for an adaptation not only of the component to which it is to be attached, but provides for an adapted connector capable of being connected to by still other components.

As relatively high gas delivery flow rates may be used with the embodiments or configurations described herein, the gases being supplied or delivered to the user or patient may be delivered to different parts of the user's or a patient's airway. The gases being supplied may reach the patient's lungs or any part of the respiratory system.

For example, according to those various embodiments and configurations described herein, a flow rate of gases supplied or provided to an interface or via a system, such as through a flow path, may comprise, but is not limited to, flows of at least about 5, 10, 20, 30, 40, 50, 60, 70, 80, 90, 100, 110, 120, 130, 140, or 150 liters per min (LPM), or more, and useful ranges may be selected between any of these values (for example, about 40 to about 80, about 50 to about 80, about 60 to about 80, about 70 to about 80 LPM). Optionally, the gases supplied may be delivered in a fully saturated or humidified condition, or a saturated or humidified gas may be blended with other gases for supply or delivery to a patient interface or the patient.

Such relatively high flow rates of gases may assist in providing the supplied gases into a user's airway, or to different parts of a user's airway, for example such flow rates may allow for a delivery of such gases to the upper or lower airway regions. Upper airway region typically includes the nasal cavity, pharynx and larynx, while the lower airway region typically includes the trachea, primary bronchi and lungs.

It would be desirable to provide a system in which the humidity and temperature of the gas reach an ideal gas condition, for example, about 37° C. and about 44 mg/l as quickly as possible, and tubing for such systems.

In accordance with at least one of the embodiments disclosed herein, there is provided a connector for connecting a breathing circuit to a patient interface comprises a filter.

The connector may comprise a one way valve.

In accordance with at least one other embodiment disclosed herein, there is provided a connector for connecting a breathing circuit to a patient interface comprises a filter provided in pneumatic connection with a one-way valve.

In the connector, the filter is one of a HEPA filter, sock filter, stacked disc filter, spiral filter, pleated sheet filter, block of filter material, nano fibre filter, a disc of filter material with streams of filter material to free flow from or off the disc in fluid flow.

In the connector, the one way valve may open in response to an application of a flow applied or directed toward the patient interface through said breathing circuit and may close or shut in response to an application of no flow applied or directed toward the patient interface through said breathing circuit.

In the connector, the filter may be attached to an outlet of the one way valve.

In the connector, the one way valve may be a duckbill valve.

In the connector, the filter may comprise an expanding filter material, the expanding filter material attached to the duckbill end of the duckbill valve, so that as the valve opens the filter material expands to allow flow through the valve and filter material.

The connector may be a reducing union or socket or adapter.

In the connector, the filter is formed from a filter material comprising one or more of mineral fibres, glass fibres, ceramic fibres, polypropylene, expanded polytetrafluoroethylene, modacrylic and Estane®, cellulose fibres, or electrostatic fibres.

The filter may be hydrophobic.

The filter may be hydrostatic.

The filter may allow air and water vapour to pass through.

The connector may be provided as a single use item.

In accordance with at least one of the embodiments disclosed herein, there is provided a breathing circuit comprising a filter. Optionally, a conduit of the breathing circuit may comprise the filter. The filter may be located at or adjacent an end of the conduit. The filter may comprise one or more features as described above in relation to a connector comprising a filter.

In accordance with at least one of the embodiments disclosed herein, a filter for a respiratory breathing circuit and/or a patient interface is one of a HEPA filter, sock filter, stacked disc filter, spiral filter, pleated sheet filter, nano fibre filter, block of filter material, a disc of filter material with streams of material to free flow from or off the disc in fluid flow, the filter adapted to be fitted into a patient interface or breathing circuit conduit.

According to the embodiments above, the filter may be formed from a filter material comprising one or more of mineral fibres, glass fibres, ceramic fibres, polypropylene, expanded polytetrafluoroethylene, modacrylic and Estane®, cellulose fibres, or electrostatic fibres.

The filter may be hydrophobic.

The filter may be hydrostatic.

The filter may allow air and water vapour to pass through.

The connector may be provided as a single use item.

In accordance with at least one of the embodiments disclosed herein, there is provided a patient interface tube that comprises an open cell foam material with a sealing skin, such that the patient interface tube is breathable in that it allows water vapour to pass through the material and sealing skin, but does not allow the passage of liquid water or bulk flow of gases therethrough. The interface tube providing a tube or conduit for the gases flow to be provided from a breathing circuit to a patient interface.

In accordance with at least one of the embodiments disclosed herein, there is provided a nasal cannula comprising one or two nasal prongs to fit into a patient's nostrils, each nasal prong providing a filter for a flow of gases from the patient interface to a patient.

In accordance with at least one of the embodiments disclosed herein, there is provided a filter and valve arrangement for a respiratory breathing circuit that comprises a one way valve and a filter attached to an outlet of the one way valve.

The one-way valve may be a duckbill valve.

The filter may comprise an expanding filter material, the expanding filter material attached to the duckbill end of the duckbill valve, so that as the valve opens the filter material expands to allow flow through the valve and filter material.

In accordance with at least one of the embodiments disclosed herein, there is provided a method for preventing contamination of a breathing circuit for use by more than one patient, the method comprising installing a filter in the breathing circuit or patient interface to prevent contamination of the breathing circuit for use by multiple patients.

In accordance with at least one of the embodiments disclosed herein, there is provided a method for preventing contamination of a breathing circuit for use by more than one patient, the method comprising disinfecting a breathing conduit or tube of the breathing circuit using a disinfectant, wherein the disinfectant comprises one or more of (in liquid or gas form) ortho-phthalaldehyde, glutaraldehyde, hydrogen peroxide, and nitrogen dioxide.

The disinfectant may be distributed into a breathing conduit or tube from a disinfection reservoir that releases disinfectant when the circuit is not in use on a patient.

The method may further use a disinfection capsule that caps an end of the breathing circuit.

The capsule may comprise a push button for release of disinfectant.

The capsule may be built into the breathing circuit or a separate component that a user inserts into an end of the breathing circuit.

The disinfection reservoir may be provided in the walls of a conduit of the breathing circuit or a connector of the breathing circuit, and may be released through one way valves into the breathing circuit via a release mechanism.

The release mechanism may be actuated by a signal that is generated when a patient interface is removed from the circuit. For example, the signal may be an electric signal, mechanical signal, or a magnetic signal.

A flushing disinfection unit may be attached to each end of the breathing circuit and may alternate between flushing the circuit with water or disinfectant.

In accordance with at least one of the embodiments disclosed herein, there is provided a disinfectant capsule for disinfecting a breathing circuit that comprises a reservoir and a release mechanism for releasing disinfectant into the breathing circuit.

The capsule may form a cap for capping the end of a breathing tube or conduit of the breathing circuit.

The release mechanism may comprise a push button for release of disinfectant.

The capsule may be built into the breathing circuit or a separate component that a user inserts into an end of the breathing circuit.

A signal may be generated when a patient interface is removed from the circuit to actuate the release of the disinfectant. Such a signal may be an electric signal, mechanical signal, or a magnetic signal.

In accordance with at least one of the embodiments disclosed herein, there is provided a breathing circuit that comprises a reservoir in the walls of a tube or conduit of the breathing circuit for holding a volume of disinfectant, and one or more valves between the reservoir and a lumen of the breathing circuit, in use the disinfectant released or releasable from the reservoir into the breathing circuit via actuation of the valves.

The breathing circuit may comprise a release mechanism for actuating the valves to release the disinfectant.

A signal can be generated when a patient interface is removed from the circuit to actuate the release of the disinfectant. Such a signal may be an electric signal, mechanical signal, or a magnetic signal.

In accordance with at least one of the embodiments disclosed herein, there is provided a method for preventing contamination of a breathing circuit for use by more than one patient, the method comprising attaching a flushing disinfection unit to each end of the breathing circuit and using the unit to alternately flush the circuit with water and disinfectant.

In accordance with at least one of the embodiments disclosed herein, there is provided a method for preventing contamination of a breathing circuit for use by more than one patient, the method comprising providing radiation (for example, ultraviolet light or near infrared ultra-short pulsed laser) to the breathing circuit to inactivate microorganisms.

The method may comprise delivering a sheet of radiation at a connection point between a breathing circuit and a patient interface.

The radiation may be delivered to the breathing circuit continuously, including during use of the circuit by a patient.

The radiation may be delivered to the breathing circuit only when a patient interface is disconnected (from said breathing circuit).

In accordance with at least one of the embodiments disclosed herein, there is provided a connector or conduit of a breathing circuit that comprises a radiation source to prevent contamination of the breathing circuit for use by more than one patient.

The radiation source may provide a sheet of radiation at a connection point for connecting a patient interface to the breathing circuit.

The radiation source may provide individual beams of radiation or sheets of radiation throughout the circuit.

In accordance with at least one of the embodiments disclosed herein, there is provided a humidifier or other hardware of a respiratory breathing system upstream of a breathing circuit that connects with an end of the breathing circuit that comprises a radiation source, the radiation source providing radiation to the breathing circuit to prevent contamination of the breathing circuit for use by more than one patient.

In accordance with at least one of the embodiments disclosed herein, there is provided a method for preventing contamination of a breathing circuit including increasing heat in the breathing circuit for a period of time between patients (with or without the gas flow running) to kill microorganisms.

The method may comprise increasing the heat output of a heating element in the breathing circuit for said period of time.

A disinfection unit may be attached to each end of the breathing circuit and used to cycle hot water (e.g. at 90° C.) and detergent through the breathing circuit for said period of time. The disinfection unit may be a separate unit or may be built-in with any other hardware (for example, a humidifier) upstream of the breathing circuit.

A heated collar may be provided at a connection point between the breathing circuit and a patient interface to stop infectious matter migration from the patient into the breathing circuit.

In accordance with at least one of the embodiments disclosed herein, there is provided a breathing circuit that comprises a tube or conduit or other component in contact with respiratory gases that is formed from a plastics material with one or more antimicrobial additives.

The additives may be one or more of silver and silver based additives (colloidal silver, silver salts, silver zeolite, nano silver), siloxane based additives, Triclosan, and copper.

The breathing circuit may comprise a collar around an end or connection point of the breathing circuit where a patient interface is attached or attachable, the collar formed from said material with one or more antimicrobial additives.

The or an entire breathing circuit may be made with antimicrobial additives, for example a breathing tube or conduit may be made from a plastics material including antimicrobial additives.

In accordance with at least one of the embodiments disclosed herein, there is provided a breathing circuit that comprises a cap for covering an end of the breathing circuit to prevent contamination of the breathing circuit.

The cap may be built into the breathing circuit and may be activated by a signal to cover the end of the breathing circuit. For example, the signal may be an electrical, mechanical or magnetic signal generated when the patient interface is removed or unplugged from the breathing circuit.

The breathing circuit may include a pressure relief system or stop flow system to prevent over pressure in the breathing circuit when the cap is covering the end of the breathing circuit.

The cap may comprise a pressure release mechanism.

The cap may comprise a relief valve.

In accordance with at least one of the embodiments disclosed herein, there is provided a breathing circuit that comprises an orifice to create a fast flow through the orifice to prevent infectious matter travelling back into the breathing circuit against the direction of flow through the orifice.

The orifice may be configured to provide a Peclet number greater than 1, or 10, or 100, or 1000.

In accordance with at least one of the embodiments disclosed herein, there is provided a breathing circuit, or a patient interface, or a connector for connecting a breathing circuit to a patient interface, that comprises a one way valve, to prevent contamination from patients entering the breathing circuit.

The valve may be one of a duckbill valve, an umbrella valve, a check ball valve, or a constant velocity valve.

The valve may be inspiratory triggered, so that gas flow passes through the valve only during inspiration when a pressure differential across the valve allows the valve to open.

The breathing circuit may include a pressure relief system to ensure the breathing circuit is not over pressurized.

In accordance with at least one of the embodiments disclosed herein, there is provided a method for preventing contamination of a breathing circuit for use by more than one patient, the method comprising providing a one valve to a breathing circuit or patient interface to prevent contamination from patients entering the breathing circuit.

The valve may be one of a duckbill valve, an umbrella valve, a check ball valve, or a constant velocity valve.

The valve may be provided as a separate element to be inserted into or attached to a conduit and/or patient interface.

In accordance with at least one of the embodiments disclosed herein, there is provided a method for preventing contamination of a breathing circuit for use by more than one patient, the method comprising providing a flow of respiratory gases through the breathing circuit to a patient at a first flow rate during an operating mode, and providing a flow of respiratory gases through the breathing circuit at a second flow rate during a non-operating mode, wherein the first flow rate is higher than the second flow rate. The flow along the breathing circuit at the second flow rate being sufficient for preventing or reducing contamination entering the breathing circuit.

The first flow rate may be about 70 L/min and the second flow rate may be about 10 L/min.

A flow source may provide a flow of respiratory gases to the breathing circuit, or other hardware of a respiratory breathing system upstream of the breathing circuit, the flow source comprising a switch that allows the flow to be switched from the first flow rate in an operational mode to the second flow rate in a non-operational mode.

An item of equipment upstream of the breathing circuit, such as a flow source, may include an electrical connection that initiates the second flow when a flow source is connected to the breathing circuit and/or when a patient interface is disconnected from the breathing circuit.

An item of equipment upstream of the breathing circuit, such as a flow source, may include an electrical connection that initiates the second flow when the breathing circuit is connected to a patient interface.

An item of equipment upstream of the breathing circuit, such as a flow source, may include a mechanical switch (e.g. push valve) that allows different sized orifice openings to be introduced to the flow path to switch between the first and second flow rates.

In accordance with at least one of the embodiments disclosed herein, there is provided a breathing circuit, or a patient interface, or a connector for connecting a breathing circuit to a patient interface, that comprises a mesh of hydrophobic material at a connection point between the patient interface and the respiratory breathing circuit, the mesh adapted to prevent contamination from patients entering the breathing circuit.

The breathing circuit may comprise a conduit and the mesh is provided at an end of the conduit.

The patient interface may include an inlet for connecting to the breathing circuit and the mesh is provided in the inlet.

The mesh may be hydrophobic.

The mesh may have a pore size that allows flow through the mesh at an operational flow rate and an operating pressure to the patient interface, but which does not allow (or prevents) exhaled breath from the patient to pass through the mesh, a pressure (or flow rate) of the exhaled breath being too low for exhaled breath to pass through the mesh.

The mesh may have a pore size to allow an operational flow rate of about 70 L/min to pass from the breathing circuit to the patient.

As relatively high gas delivery flow rates may be used with the embodiments or configurations described herein, the gases being supplied or delivered to the patient may be delivered to different parts of the patient's airway.

The filter as described here, or components to be associated with the filter, may be adapted by connection of an adapter insert, the adapter insert may be that as described elsewhere in this specification.

For example, according to those various embodiments and configurations described herein, a flow rate of gases supplied or provided to an interface or via a system, such as through a breathing circuit, may comprise, but is not limited to, flows as defined by the high gas delivery flow rates described previously herein.

Such relatively high flow rates of gases may assist in providing the supplied gases into a patient's airway, or to different parts of a patient's airway. For example, such flow rates may allow for a delivery of such gases to the upper or lower airway regions. Upper airway region typically includes the nasal cavity, pharynx and larynx, while the lower airway region typically includes the trachea, primary bronchi and lungs.

Certain features, aspects and advantages of some configurations of the present disclosure have been described with reference to respiratory breathing circuits for use alongside or together with anaesthetic breathing circuits. However, certain features, aspects and advantages of the configurations as described may advantageously be used with other respiratory systems.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples only.

BRIEF DESCRIPTION OF THE DRAWINGS

Specific embodiments and modifications thereof will become apparent to those skilled in the art from the detailed description herein having reference to the figures that follow, of which:

FIG. 13 is a perspective view of a third exemplary form nasal cannula assembly for use in the kit and apparatus, particularly showing a gases flow manifold part that allows for the attachment of removable prongs.

FIG. 14 is a perspective view of the third form of the nasal cannula assembly, showing a strap and breathable pad fittable to the manifold part of FIG. 13.

FIG. 15 is a perspective view of a first form of removable prongs capable of being attached to the manifold part of FIG. 13.

FIG. 16 is a perspective view of a second form of removable prongs capable of being attached to the manifold part of FIG. 13.

FIG. 22E is a schematic representation of yet another alternative filter element.

FIGS. 23A and 23B are schematic representations of a connector or component comprising a one way valve and a filter element integrated with the one way valve. FIG. 23A shows the one way valve in a closed configuration and FIG. 23B shows the one way valve in an open configuration.

FIGS. 26A and 26B illustrate a cap provided to a breathing circuit to prevent contamination entering the breathing circuit.

DETAILED DESCRIPTION

Figure 1:
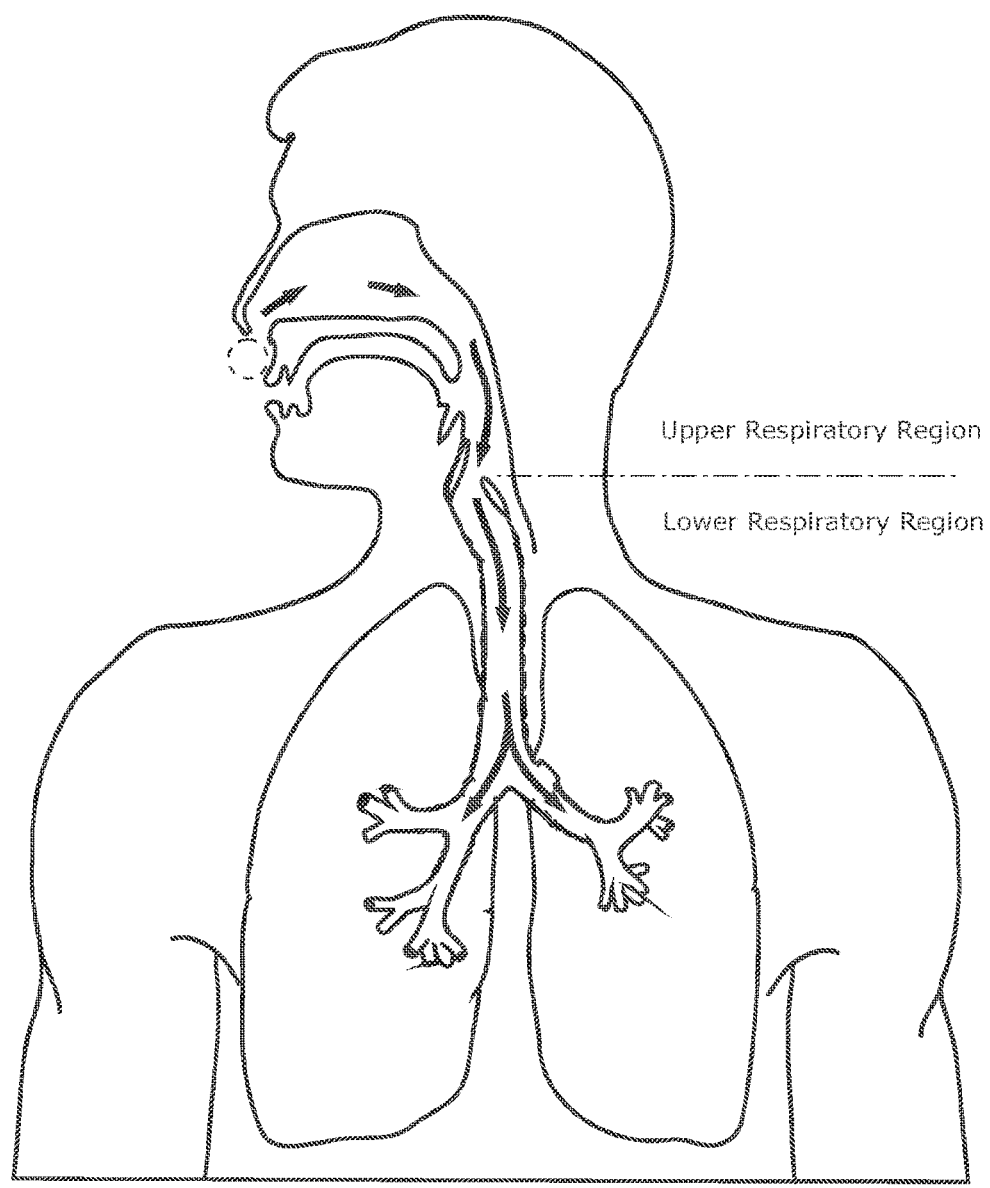
FIG. 1 shows a typical airway of a person, and includes arrows to indicate how a relatively high flow rate of gases supplied to a user may be utilised to effectively push or drive the supplied gases further or deeper into a user's airway than when the person is under normal or typical self-driven respiratory conditions, or when the patient is apnoeic.

FIG. 1 shows a typical airway of a person, and includes arrows to indicate how a relatively high flow rate of gases supplied to a user may be utilised to effectively push or drive the supplied gases further or deeper into a user's airway than when the person is under normal or typical self-driven respiratory conditions. The use of high flow rate gas delivery helps to push the gas flow and hence O2 deeper into the patient's airways. In some situations, the high flow rate of gas delivery may be utilised when the patient is not spontaneously breathing, i.e. when the patient is apnoeic.

The apparatuses described herein may be used in respiratory care or therapy systems, whether high or low flow therapy, or whether as a sealed or non-sealed interface, for example humidified PAP delivery or in-hospital respiratory care systems.

Figure 2:
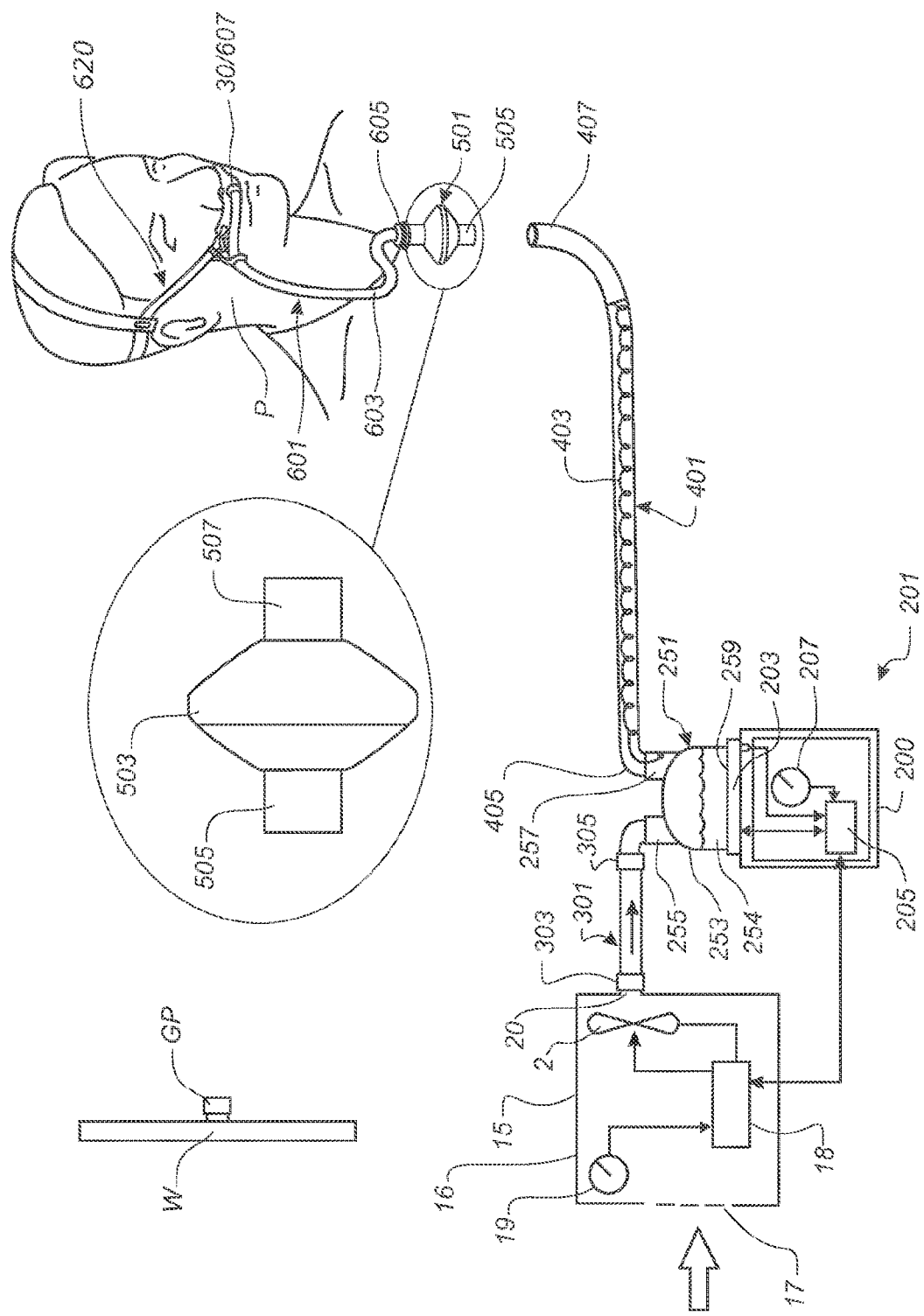
FIG. 2 schematically shows a respiratory therapy system incorporating a kit of FIG. 3 or 4, with a patient P wearing a patient interface.

FIG. 2 illustrates a humidifying respiratory circuit. A patient P is receiving humidified and pressurised gases through a nasal cannula assembly of a patient interface 601 that is operatively connected to a humidified gases transportation pathway or inspiratory conduit 401 via a filter 501. The inspiratory conduit 401 in turn is connected to a humidifier 200 (including humidifier chamber 251) that is supplied with gases from a blower 15 or other appropriate gases supply means via a gases delivery conduit 301. The gases delivery conduit is a 'dry' conduit; that is, it is positioned upstream of the humidifier. Headgear 620 is provided to support and retain the patient interface against the patient's face.

The inspiratory conduit 401 is connected to the outlet 257 of the humidifier chamber 251 which contains a volume of liquid such as water. Humidifier chamber 251 may be formed from a plastics material and may have a highly heat conductive base 259 (for example an aluminium base) which is in direct contact with a heater plate 203 of humidifier 200.

The humidifier 200 is provided with control means or electronic controller 205 which may comprise a microprocessor based controller executing computer software commands stored in associated memory. Gases flowing through the inspiratory conduit 401 are passed to the patient by way of the filter 501 and patient interface 601.

The controller 205 receives input from sources such as user input means or dial 207 through which a user of the device may, for example, set a predetermined required value (pre-set value) of humidity or temperature of the gases supplied to patient P. In response to the user set humidity or temperature value input via dial 207 and other possible inputs such as internal sensors that sense gases flow or temperature, or by parameters calculated in the controller, controller 205 determines when (or to what level) to energise heater plate 203 to heat the water within humidifier chamber 251. As the volume of water within humidifier chamber 251 is heated, water vapour begins to fill the volume of the chamber above the water's surface and is passed out of the humidifier chamber 251 outlet port 257 with the flow of gases (for example air) provided from a gases supply means or blower 15 which enters the chamber through gases inlet port 255. It should be noted that it is possible to obtain the relationship between the humidity of the gases in humidifier chamber 251 and the temperature of the heater plate 203. Accordingly, it is possible to utilise the heater plate temperature in an algorithm or a look-up table to determine the humidity of the gases.

The blower 15 may be provided with a variable speed pump or fan 2 which draws air or other gases through the blower inlet 17. The speed of variable speed pump or fan 2 may be controlled by a further control means or electronic controller 18 (or alternatively the function of this controller 18 could be carried out by the other controller 205) in response to inputs from controller 205 and a user set predetermined required value (pre-set value) of pressure or fan speed or flow rate via dial 19 or other input device. Alternatively, the gases may be provided from a wall supply; i.e. a wall gas port GP in a wall W.

A housing 16 of the blower is provided with an outlet port 20. An inlet port 303 of the gases delivery conduit 301 and the outlet port 20 of the blower are provided with complementary coupling features to connect the outlet port 20 with the inlet port 303, and to provide a gases flow path therethrough. The complementary coupling features may in part be provided by an adapter insert, such as that adapter insert 900, which provides for male connection fingers. In this way, the various ports of the item or component to which an adapter insert may be attached or connected can be considered to be an 'another component' as is described elsewhere in this specification in relation to what an adapter insert may be attached or connectable to.

The male connection fingers can provide for a first part of a complementary coupling.

In some configurations, rather than using a blower 15, gases flow may be obtained from some other source(s) of gas. For example, in some configurations, source(s) of gas may comprise one or more containers of compressed air and/or another gas and one or more valve arrangements adapted to control the rate at which gases leave the one or more containers. As another example, in some configurations, gases may be obtained from an oxygen concentrator. The system may also include a supplementary gases source to provide an air and supplementary gas mixture. For example, the supplementary gas might be O2. In some configurations, the apparatus may be adapted to deliver a high flow therapy.

"High flow therapy" as used in this disclosure may refer to delivery of gases to a patient at a flow rate of greater than or equal to about 5 or 10 liters per minute (5 or 10 LPM).

In some configurations, 'high flow therapy' may refer to the delivery of gases to a patient at a flow rate of between about 5 or 10 LPM and about 150 LPM, or between about 15 LPM and about 95 LPM, or between about 20 LPM and about 90 LPM, or between about 25 LPM and about 85 LPM, or between about 30 LPM and about 80 LPM, or between about 35 LPM and about 75 LPM, or between about 40 LPM and about 70 LPM, or between about 45 LPM and about 65 LPM, or between about 50 LPM and about 60 LPM. For example, according to those various embodiments and configurations described herein, a flow rate of gases supplied or provided to an interface or via a system, such as through a flowpath, may comprise, but is not limited to, flows of at least about 5, 10, 20, 30, 40, 50, 60, 70, 80, 90, 100, 110, 120, 130, 140, 150 L/min, or more, and useful ranges may be selected between any of these values (for example, about 40 to about 80, about 50 to about 80, about 60 to about 80, about 70 to about 100 L/min, about 70 to 80 L/min).

Gases delivered may comprise a percentage of oxygen. In some configurations, the percentage of oxygen in the gases delivered may be between about 20% and about 100%, or between about 30% and about 100%, or between about 40% and about 100%, or between about 50% and about 100%, or between about 60% and about 100%, or between about 70% and about 100%, or between about 80% and about 100%, or between about 90% and about 100%, or about 100%, or 100%.

High flow therapy has been found effective in meeting or exceeding the patient's normal real inspiratory demand, to increase oxygenation of the patient and/or reduce the work of breathing. Additionally, high flow therapy may generate a flushing effect in the nasopharynx such that the anatomical dead space of the upper airways is flushed by the high incoming gas flows. This creates a reservoir of fresh gas available of each and every breath, while minimising re-breathing of carbon dioxide, nitrogen, etc.

The humidifier 200 has a humidifier base comprising a housing 201 with the heater 203, the controller 205 that is coupled to the heater, and the user input device 207 to enable a user to turn on and off the humidifier and to select a desired temperature to be provided by the heater. The user input device 207 may for example be a button, switch, or touch screen display. The heater 203 may comprise one or more heating elements.

The humidifier base is configured to receive the humidifier chamber 251. The humidifier chamber 251 comprises a housing 253 defining an internal liquid reservoir 254, an upstream gases inlet port 255 in fluid/pneumatic communication with the liquid reservoir, a downstream gases outlet port 257 in fluid/pneumatic communication with the liquid reservoir, and a base 259. The base 259 is arranged to be positioned on or above the heater 203 to heat liquid in the liquid reservoir. The base may comprise a flange 261 that projects outwardly from an adjacent portion of the housing 253, to assist with locating the humidifier chamber in position on the humidifier base.

The gases inlet port 255, the liquid reservoir 254, and the gases outlet port 257 are in fluid/pneumatic communication to provide a gases flow path from the gases inlet port 255, through or past the liquid reservoir, to the gases outlet port 257 to heat and humidify gases travelling along the gases flow path.

The humidifier chamber 251 may be any suitable chamber that holds suitable liquid for use in humidifying gases, such as water for example. The humidifier chamber 251 may be a manual fill chamber, and may be filled through a liquid inlet port 263. Alternatively, the humidifier chamber 251 may be an automatically filling chamber, and liquid may be fed to the humidifier chamber from a liquid container, bag, or other liquid source. The humidifier chamber may comprise a float valve in the liquid reservoir, the float valve configured to control flow of liquid form the liquid container into the liquid reservoir.

A gases delivery conduit 301 is located upstream of the humidifier chamber 251. The gases delivery conduit 301 is in fluid/pneumatic communication with the humidifier chamber 251 or is configured to be placed in fluid/pneumatic communication with the humidifier chamber upstream of the humidifier chamber; i.e. with the humidifier chamber 251 downstream of the gases conduit 301. The gases delivery conduit 301 is configured to receive one or more gases from a source of gas and deliver the gas(es) to the gases inlet port 255 of the humidifier chamber.

The gases delivery conduit 301 has an upstream gases inlet port 303 at one end of the conduit, and a downstream gases outlet port 305 at the opposite end of the conduit. The gases inlet port 303 and the gases outlet port 305 are in fluid/pneumatic communication to provide a gases flow path from the gases inlet port 303 through the gases delivery conduit to the gases outlet port 305. The gases outlet port 305 of the gases delivery conduit and the gases inlet port 255 of the humidifier chamber 251 may comprise complementary coupling features, to enable the gases delivery conduit 301 to be coupled to the humidifier to provide fluid/pneumatic communication between the gases delivery conduit 301 and the humidifier chamber 251. The complementary coupling features of the gases outlet port 305 of the gases delivery conduit 301 and the gases inlet port 255 of the humidifier chamber 251 may be disconnectable from each other to enable the gases delivery conduit 251 to be decoupled from the humidifier chamber 251. Alternatively, the complementary coupling features may be permanently or semi-permanently coupled.

In relation to the complementary coupling features, at least some of those may be provided by an adapter insert, such as adapter insert 900 comprising of male connection fingers 901.

The gases inlet port 303 of the gases delivery conduit may be provided with coupling feature(s) to enable the gases delivery conduit to be coupled to the source of gas.

An inspiratory conduit 401 extends from the humidifier chamber 251 to link the humidifier to a patient interface 601 via an in-line filter 501. The inspiratory conduit 401 may comprise a conduit heater 403 adapted to heat gases passing through the conduit 401. The heater 403 will help minimise or prevent the formation of condensation in the inspiratory conduit, which could otherwise occur due to a temperature differential between the interior of the conduit wall and exterior of the conduit wall. In other configurations the conduit heater 403 may not be present. The inspiratory conduit 401 comprises an upstream gases inlet port 409 at one end of the conduit and a downstream gases outlet port 405 at the opposite end of the conduit, with the conduit defining a gases flow path from the gases inlet port 409 to the gases outlet port 405.

The humidifier chamber 251 is in fluid/pneumatic communication with the inspiratory conduit 401 upstream of the inspiratory conduit 401 or is configured to be placed in fluid/pneumatic communication with the inspiratory conduit 401 upstream of the inspiratory conduit; i.e. with the inspiratory conduit positioned downstream of the humidifier chamber 251. The gases outlet port 257 of the humidifier chamber 251 and the gases inlet port 409 of the inspiratory conduit 401 may comprise complementary coupling features, to enable the inspiratory conduit to be coupled to the humidifier to provide fluid/pneumatic communication between the humidifier chamber 251 and the inspiratory conduit 401. The complementary coupling features of the gases outlet port 257 of the humidifier chamber 251 and the gases inlet port 409 of the inspiratory conduit 401 may be disconnectable from each other to enable the inspiratory conduit 401 to be decoupled from the humidifier chamber 251. Alternatively, the complementary coupling features may be permanently or semi-permanently coupled.

The inspiratory conduit 401 will typically have a longer length than the gases delivery conduit 301.

The filter 501 comprises a generally cylindrical filter housing 503 with an enlarged central body portion. A leading edge of the enlarged central body portion comprises a tapering wall that terminates at an upstream gases inlet port 505, and a trailing edge of the enlarged central body portion terminates at a downstream gases outlet port 507. The gases inlet port 505 and gases outlet port 507 are in fluid/pneumatic communication via the central body portion. The filter may be a high-efficiency particulate arrestance (HEPA)

filter. The enlarged central portion of the filter housing contains suitable filtration material. For example, the filtration material may comprise pleated paper, nano-fibers, or any other suitable filtration material, including sock filters, stacked disc filters, spiral filters, block(s) of filter material, a disc or discs of filter material with streams of filter material to free flow from or off the disc in fluid flow. The filter captures and prevents downstream passage therethrough of particulates, bacteria and/or other infectious material from the inspiratory conduit to the patient, and also captures and prevents upstream passage therethrough of bacteria and/or other infectious material from the patient to the inspiratory conduit.

Figure 5:
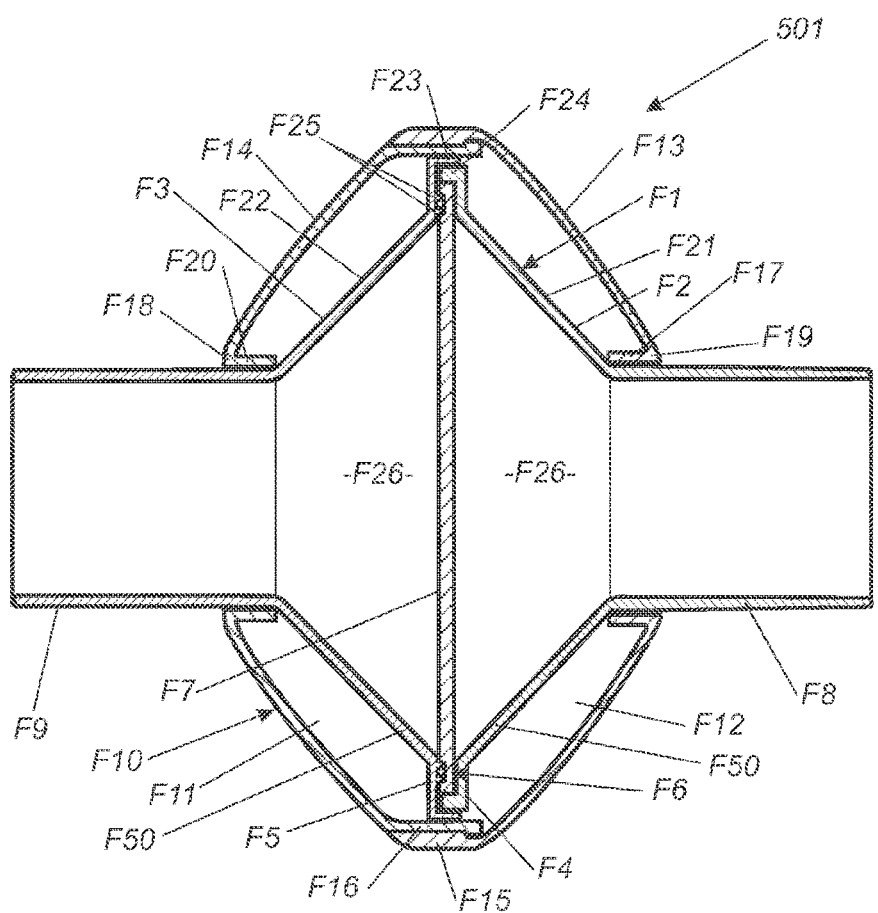
FIG. 5 shows a side elevation in cross section of an exemplary filter for use in the kit or apparatus.
Figure 6A:
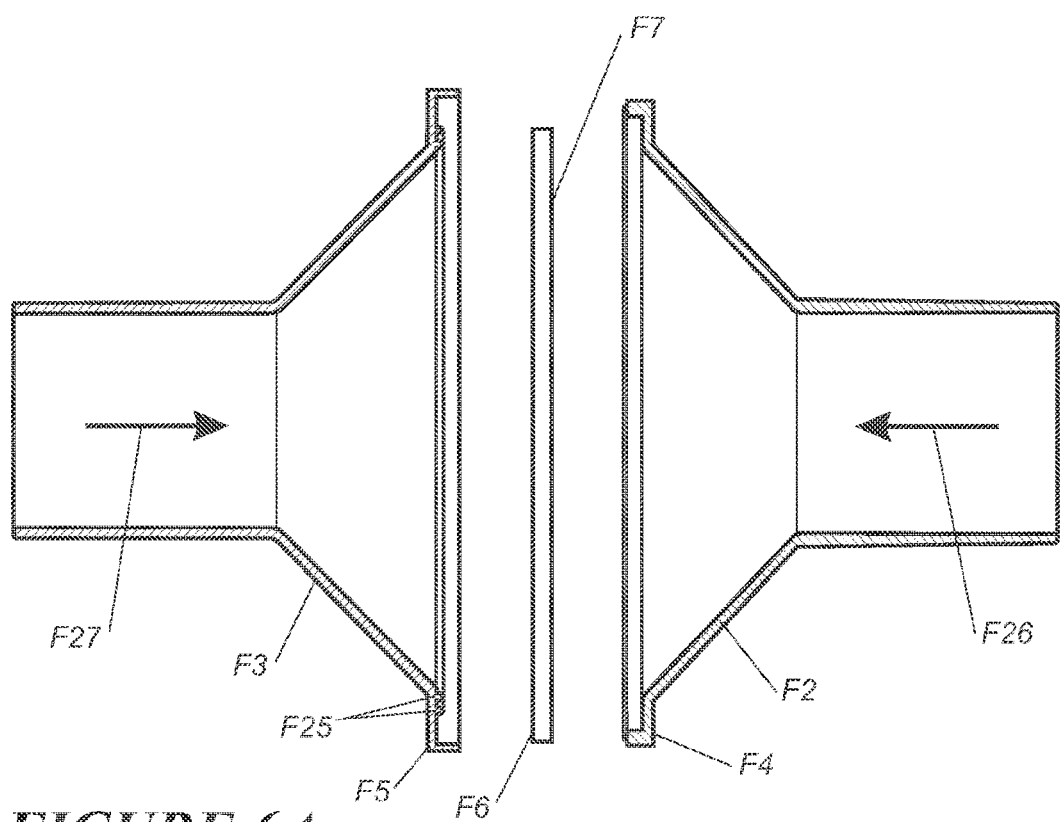
FIGS. 6A-6D demonstrate the process of assembly of the filter of FIG. 5.
Figure 6B:
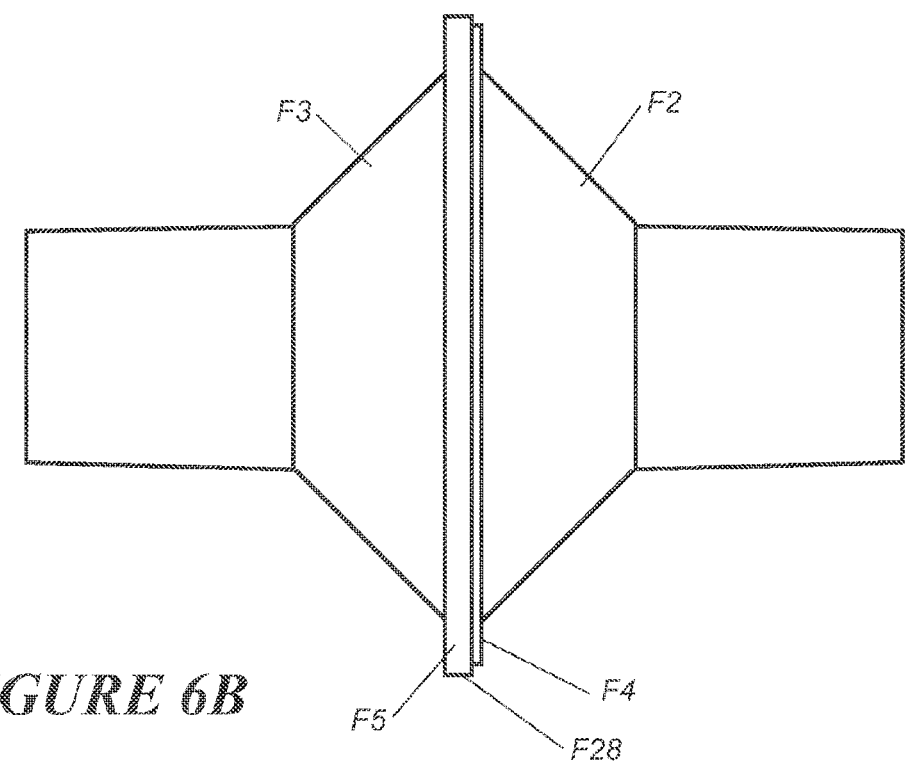
Figure 6C:
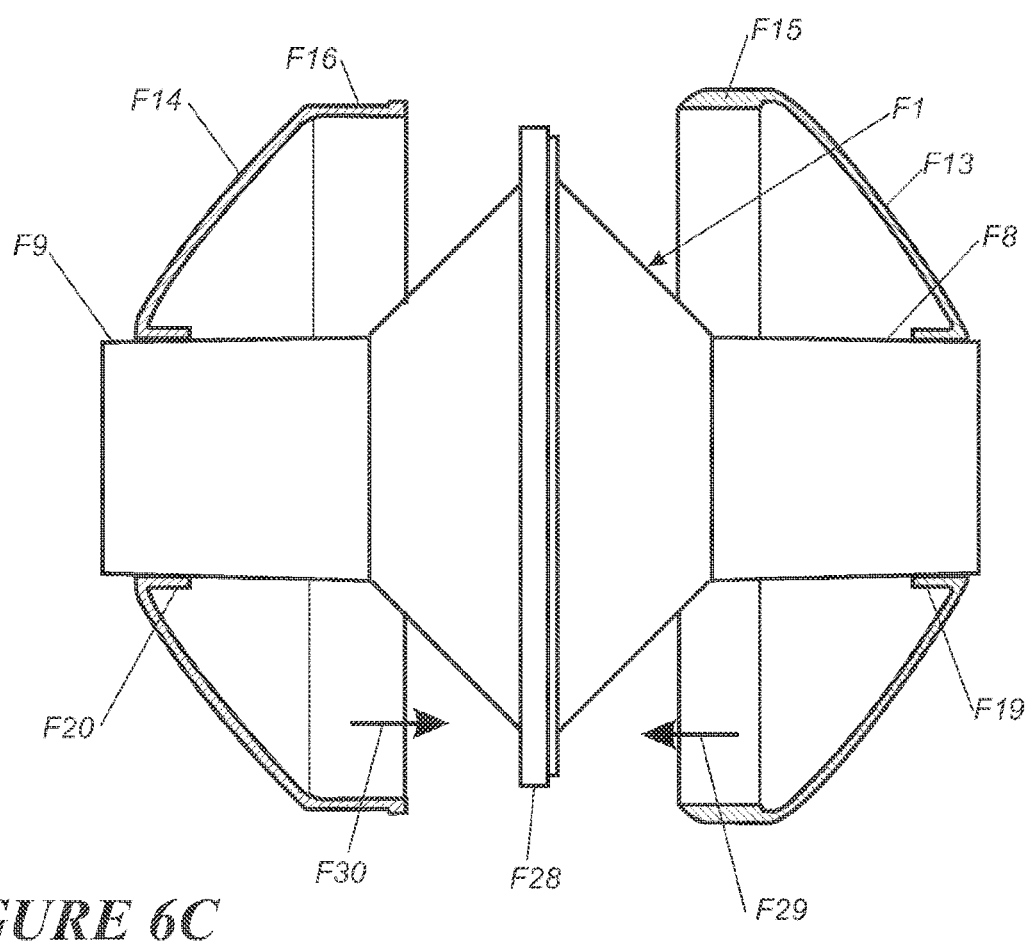
Figure 6D:
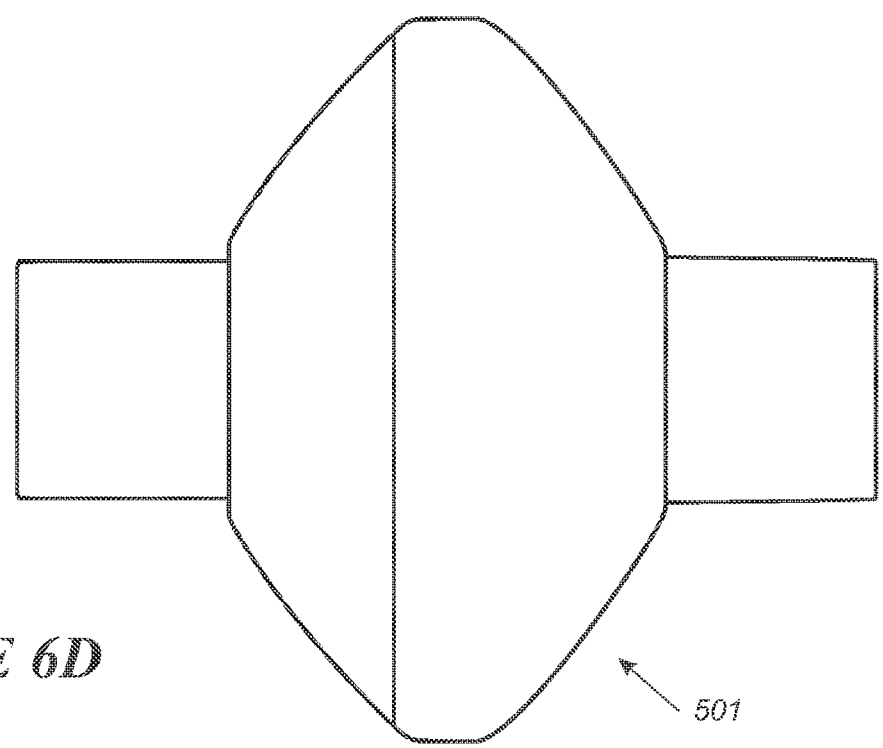

An exemplary filter is described herein with reference to FIGS. 5 to 6D. Alternatively, the filter could be any other suitable type.

The inspiratory conduit 401 is in fluid/pneumatic communication with the filter 501 upstream of the filter or is configured to be placed in fluid/pneumatic communication with the filter upstream of the filter; i.e. with the filter located downstream of the inspiratory conduit. The gases inlet port 505 of the filter 501 and the gases outlet port 405 of the inspiratory conduit 401 comprise complementary coupling features, to enable the inspiratory conduit to be coupled to the filter to provide fluid/pneumatic communication between the inspiratory conduit and the filter. The complementary coupling features of the gases inlet port 505 of the filter and the gases outlet port 405 of the inspiratory conduit are disconnectable from each other to enable the inspiratory conduit 401 to be decoupled from the filter 501.

Figure 3:
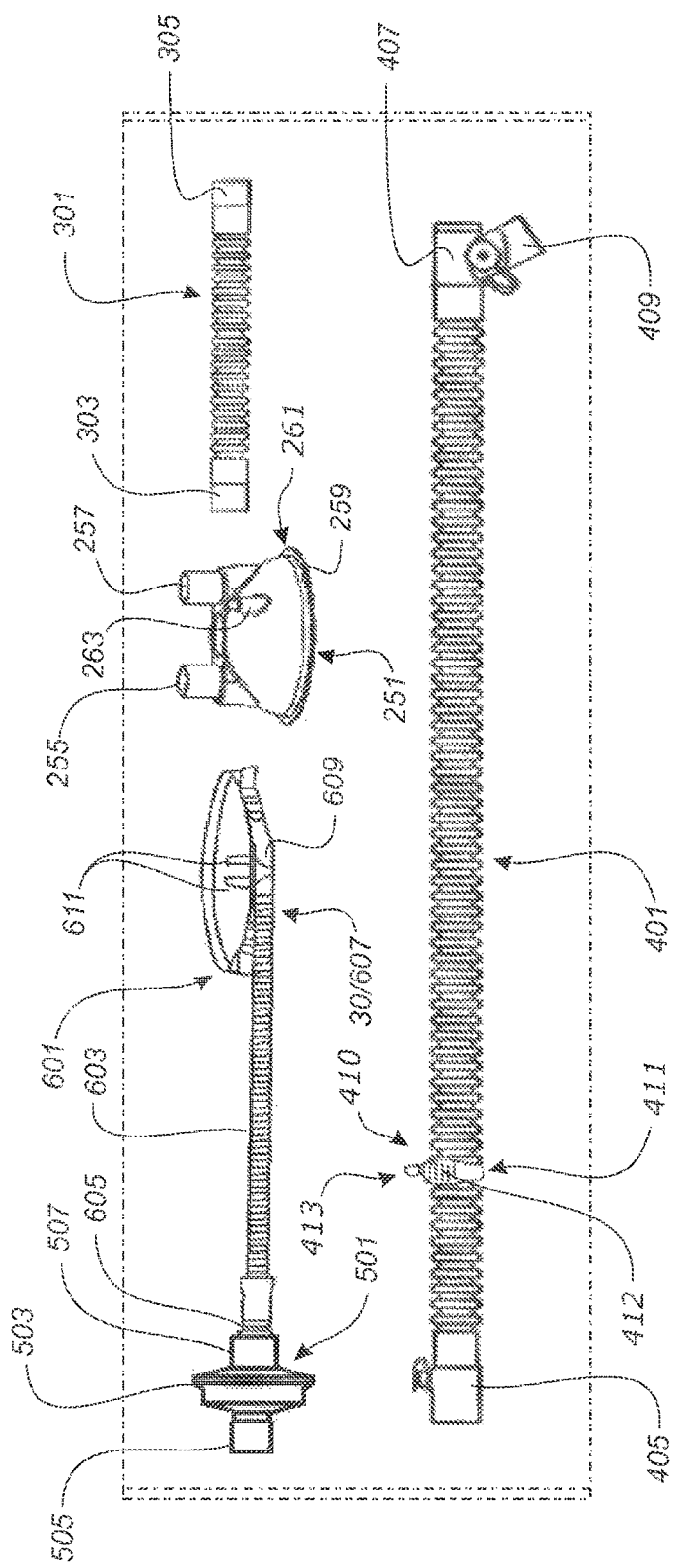
FIG. 3 shows components of a first configuration kit or apparatus for use in the respiratory therapy system.

In one configuration, the complementary coupling features between the gases outlet port 405 of the inspiratory conduit 401 and the gases inlet port 505 of the filter comprise a 22 mm medical connection or 22 mm medical taper connection. FIG. 3 shows an electrical connector 407 on the gases inlet port 409 of the inspiratory conduit. The electrical connector may provide for a power connection to a heater wire of the inspiratory conduit, or therethrough to any associated components with inspiratory conduit or other parts of the kit or assembly. The electrical connector may also all provide connection to signal, communication or sensor wires.

The filter 501 is in fluid/pneumatic communication with the patient interface 601 upstream of the patient interface or is configured to be placed in fluid/pneumatic communication with the patient interface 601 upstream of the patient interface 601; i.e. with the patient interface located downstream of the filter. In one configuration, the filter 501 is coupled to the patient interface 601 or is configured to be coupled to the patient interface 601.

The patient interface 601 comprises a patient interface gases conduit 603 with an upstream gases inlet port 605 at one end of the conduit. The opposite downstream end of the patient interface gases conduit 603 is in fluid/pneumatic communication with a patient cannula 30/607 to deliver gases from the patient interface gases conduit 603 to a patient P.

In one configuration, the gases outlet port 507 of the filter 501 and the gases inlet port 605 of the patient interface gases conduit comprise complementary coupling features to enable the filter 501 to be coupled to the patient interface 601 to provide fluid/pneumatic communication between the filter and the patient interface gases conduit, with the filter in-line with a gases flow path through the patient interface gases conduit. The complementary coupling features may be disconnectable from each other to enable the filter to be decoupled from the patient interface gases tube of the patient interface. Alternatively, the complementary coupling features may be permanently or semi-permanently coupled.

In one configuration, the complementary coupling features between the gases outlet port 507 of the filter 501 and the gases inlet port 605 of the patient interface 601 comprise a 22 mm medical taper connection.

In an alternative configuration, the patient interface 601 comprises a patient interface gases conduit 603, and the filter 501 is integrally formed with the patient interface gases conduit to provide fluid/pneumatic communication between the filter 501 and the patient interface gases conduit 603, with the filter in-line with a gases flow path through the patient interface gases conduit. That is, the filter and patient interface may be an integrated unit.

In a further alternative, the complementary coupling features may at least in part be provided by an adapter insert, for example the male connection fingers 901 of an adapter insert 900. Such male connection fingers 901 can provide for a first of a complementary connection features, while the other of the complementary connection features can be provided by the other component, for example an end of component 805 (all for example as shown in FIG. 6E). In this manner, a filter (such as filter 501) can be suitably adapted to be provided with complementary connection features allowing for the coupling and decoupling of such a filter from a respiratory circuit as desired.

In one configuration, a plurality of filters, such as each being provided in an in-line configuration, for example as a 'common filter' as previously described herein, can be used with the nasal cannula or nasal mask or other patient interfaces. The plurality of filters that are in-line to form a common filter may receive a flow of gas from an inspiratory conduit at the inlet port of the common filter. The outlet port of the common filter may be in pneumatic connection with a patient interface for delivering gas filtered by the common filter to a patient.

The patient interface 601 is shown to be a nasal cannula, although it should be understood that in some configurations, other patient interfaces may be suitable. For example, in some configurations, the patient interface may comprise a sealing or non-sealing interface, and may comprise a nasal mask, an oral mask, an oro-nasal mask, a full face mask, a nasal pillows mask, a nasal cannula, an endotracheal tube, a tracheostomy tube, a combination of the above or some other gas conveying system. In an embodiment, the patient interface 601 comprises a non-sealing interface such as a nasal cannula, which allows gases to be exchanged with the environment. For example, the non-sealing cannula allows carbon dioxide to be removed and/or cleared from the patient's airways while the patient receives flow therapy from the system. Further, in an embodiment, the patient interface is in the form of a nasal interface, such that the system does not interfere with other oral airway equipment and/or devices, for example, a tracheal tube in an intubation procedure. Accordingly, the patient may continue to receive flow therapy throughout the intubation procedure.

The patient interface gases conduit 603 forms a first gas lumen defined by a tubular wall. The first gas lumen is adapted to receive gases from the respiratory therapy system, via the inspiratory conduit 401 and filter 501 shown in FIG. 2, and channel the gases to the patient P.

The illustrated first gas lumen is defined at least in part by a wall within which gases can be channelled.

The first gas lumen may optionally comprise a reinforcement element adapted to strengthen and/or add rigidity to the first gas lumen to prevent deformation or collapse of the first gas lumen arising due to the application of forces against the first gas lumen. The reinforcement element may include a number of structures, including but not limited to plastic or metallic reinforcing beads that lie in or on the wall of the first gas lumen. Alternatively, the lumen may, in some configurations, comprise weakened sections, or sections which are unable to self-maintain their flow path or a fluid flow passage, to allow for a mask to seal over the patient interface, such as a nasal cannula or nasal mask, and to reduce or prevent the flow of gases to the patient interface.

The first gas lumen 603 is in fluid/pneumatic communication with a flow manifold 609. The flow manifold 609 receives gases from the first gas lumen 603 and passes them to one or more nasal delivery elements 611 (e.g. the nasal prongs of a nasal cannula). The one or more nasal delivery elements 611 extend outwardly from the flow manifold 609. The one or more nasal delivery elements 611 are adapted to be non-sealingly positioned in one or more nares of the patient P.

As shown, in one example, the patient interface 601 can comprise two nasal delivery elements 611 adapted to be positioned one in each of the patient's nares. Each nasal delivery element 611 may be shaped or angled such that it extends inwardly towards a septum of the patient's nose.

Additionally, each nasal delivery element may be shaped or angled such that a tip of each nasal delivery element points, in use, towards a back of the head of the patient P. In the embodiment shown in FIGS. 2 and 3, the flow manifold 609 receives flow from one lateral side of the flow manifold 609 (e.g. with respect to an imaginary vertical plane bisecting the face of the patient P) and channels flow to each of the nasal delivery elements 611. In other configurations, the patient interface 601 may comprise greater (for example, three or four) or fewer (for example, one) nasal delivery element 611.

In other configurations, each nasal delivery elements 611 can have different properties. For example, one of a pair of nasal delivery elements 611 can be relatively long and the other nasal delivery element 611 can be relatively short. In some configurations, the flow manifold 609 may be configured to receive flow from two lateral sides of the flow manifold 609 (e.g. from a 'left' and 'right' of the flow manifold 609 when instead of just the 'left' of the flow manifold 609 as seen in FIG. 2). In some such configurations, multiple gas lumens may be used to provide for pneumatic communication between the flow manifold 609 and the respiratory therapy system. In some configurations, the flow manifold 609 may be configured to receive flow from a non-lateral side of the flow manifold 609 (e.g. from a 'bottom' or 'top' of the flow manifold 609).

In other configurations, as noted, the manifold may be a separately attachable component to be attached to the body of the interface, such as a nasal cannula or nasal mask. Such a manifold may be an entirely separate component able to be removed from attachment to the interface, or it may be de-attached or disconnected from an operational position to allow for a re-orientation of the manifold (and associated supply conduit) relative to the interface. For example, the manifold may be of a push-fit type arrangement to be push-fitted into a connection with the interface body, or may be of a swivel-type connection with the body of the interface allowing for a re-orientation of the manifold. A re-orientation allows for the supply conduit to be positioned to a left or a right side of the interface (and therefore changed from one side to another of the patient). This may allow for an improved convenience or arrangement of components in a system delivering gas to the patient. For example, if those assisting in a medical procedure need access to the patient from one particular side, then the manifold can be re-oriented and the supply tube re-positioned so as to extend from a different side of the patient. Such an arrangement allows for a relatively unobtrusive application of a patient interface and its associated components away from medical specialists.

The patient interface when in the form of a nasal cannula may utilise a headgear in the form of a strap that can be bifurcated (i.e. a line of weakness or other split arrangement can be configured) to allow for the headgear or a strap thereof to be reconfigured from a single strap arrangement into a bifurcated strap arrangement.

The patient interface when in the form of a nasal cannula may utilise a pair of side arms extending from the main body (to which the manifold is to be put into connection with). The side arms may comprise of features allowing for the retention or securement or positioning of a gas supply tube to the side arm (to prevent the gas supply tube from uncontrollably moving about).

The patient interface 601 may further comprise mounts and/or supports, e.g., cheek supports, for attaching and/or supporting the gas lumen 603 and/or cannula 30/607 on the patient's face. For example, a releasable connection system may be utilised to position or locate the interface upon the patient's face, yet allow for a relatively rapid removal or re-positioning of the interface if necessary.

The filter may be coupled to an interface tube, such as a patient interface gases conduit or gas lumen, that is coupled to the manifold. The patient interface gases conduit or gas lumen may be a short section of tube or conduit. For example, the patient interface gases conduit or gas lumen may be about 20 cm to about 50 cm long, or about 25 cm to about 40 cm long, or about 30 cm to about 35 cm long, or may be about 32 cm long.

FIG. 3 additionally shows a component 410 located on or about a conduit, such as an inspiratory conduit 401. The component 410 is adapted to engage with the conduit, such as the inspiratory conduit 401, and is provided with jaws 413 extending from a body 411 of the component 410, the jaws 411 being adapted to grip an item and thereby support the conduit, such as inspiratory component 401, in use.

The jaws 411 may be a pair of opposing jaws for gripping of an item, such as a sheet or article of clothing or other item or article (e.g. a medical stand or component attached thereto) (not shown). The jaws 411 of the component 410 may be co-acting upon each other in a closed position.

The body of the component may substantially surround a perimeter of the conduit or tube upon which it is located.

The ability to locate a medical tube, such as an inspiratory conduit or tube, relative to a user has certain advantages. Being able to help support the weight of the medical tubing connected to equipment associated with the user has a number of advantages including but not limited to, for example, reducing the weight transferred to a user or equipment associated with the user, which may in turn impact on the efficiency of a treatment being provided to a user, or the overall comfort experienced by a user when using such equipment.

Further, as a user moves or re-positions their body relative to the medical tubing or associated equipment, strain may be transferred to the tubing or to the user via the associated equipment. A relatively quick and effective re-positioning or re-locating of the tubing to provide support again would be useful.

Such a component 410 can be utilised to position or locate, for example, inspiratory medical tubing, or other tubing associated with such medical circuits.

Accordingly, the component 410 is provided for use with a tube or conduit, such as an inspiratory conduit 401. The component 410 generally comprises a body 411 engageable with the external surface of a conduit or tube (e.g. such as the external surface of a corrugated tube—as for example shown in FIG. 3). The component 410 includes a pair of jaws 413 that extend from the body 411. The jaws 413 can be used for attaching to or for gripping of an item (not shown).

As shown in FIG. 3, the body 411 comprises a shoulder portion 412 associated with each jaw of the pair of jaws 413, the shoulder portion 412 providing a surface for actuation, by a user. The shoulder portion 412 is an enlarged region of the body 413. The shoulder portions 412 can be sized for actuation by fingers of a user, or are finger tabs.

It will be appreciated, the body 411 is configured to be substantially annular about the exterior surface of the, or each, respective tube or conduit, such as inspiratory conduit 401, upon which it is to be provided in association.

The component 410 may be a tube clip capable of engaging with an exterior surface or surfaces of a conduit or tube, such as the inspiratory conduit 401, where the tube clip additionally comprises a pair of jaws 413 adapted for gripping of an item, such that when the jaws 413 of the tube clip grip an item, the conduit or tube may be supported. The component 410 may for example be that as described by PCT/NZ2012/000169 (published as WO2013/073970) the entirety of the contents of which is incorporated herein by reference.

Kit and Use

FIG. 3 shows the form in which the components of the described apparatus will be provided for use with a patient. The described components will be provided as a kit in a package that comprises a sealed container or bag, which is represented by the broken line in FIG. 3. The package may, for example, be a clam shell package. The container or bag will contain the humidifier chamber 251, the gases delivery conduit 301, the inspiratory conduit 401, the filter 501, and the patient interface 601. Optionally, a tube clip (such as component 410) can also be provided in such a package. The tube clip can be provided for attachment or already attached to the inspiratory conduit 401 (and for example may be positioned or located near the patient end of such a conduit) for securing the conduit to an item (such as bedding etc.) to help reduce the load of the circuit on the patient's face, or support the circuit, and to thereby reduce the risk of dislodging the interface from the patient.

Optionally, an adapter (such as adapter insert 900) can also be provided in such a package. The adapter (such as adapter insert 900) can be used to facilitate connection between components of the system. Optionally, inlets and/or outlets of conduits in the system may comprise engagement features (for example those of another connector 805) which act to couple with the features of the adapter.

One or some of the components may be provided separately in the package; that is, they will not be coupled together. In one configuration, the filter 501, the humidifier chamber 251, the inspiratory conduit 401, and the gases delivery conduit 301 are provided separately in the package. The patient interface 601 and filter 501 may be provided separately in the package (i.e. not coupled or integrated). Alternatively, the patient interface and filter may be coupled in the package, or the filter may be integrally formed with the patient interface gases conduit of the patient interface.

Each of the various components may be provided in their appropriately coupled or connected arrangement with each other, or may be provided in a decoupled or disconnected arrangement or variations of these. For example, it may be appropriate in the package to provide for the patient interface and filter to be provided in an already coupled arrangement, such as via the gases delivery conduit 301, yet these components may not be already provided as being coupled to the humidifier chamber 251 or an inspiratory conduit 401. In further arrangements, an inspiratory conduit 401 component may be provided in a coupled arrangement with a gas inlet of the humidifier chamber 251. Further, those components that are intended to be changed between patients, such as a patient interface 601, gases delivery conduit 301 and filter 501 may be provided in a separate part of the package; whilst those parts which are to remain in the circuit despite multiple patients receiving therapy or a treatment (e.g. those parts upstream of the filter), such as the humidifier chamber 251 and inspiratory conduit 401, may be provided in another separate part of the package. Discrete parts or separations in the package may assist with maintaining cleanliness of the different components until they are required for use.

Method of Assembling Breathing Circuit Using the Apparatus, and Use of the Apparatus The apparatus described above enables the gases delivery conduit 301, inspiratory conduit 401, and humidifier chamber 251 to be re-used with multiple patients. The filter 501 will prevent contamination of the inspiratory conduit 401 by each patient. Each patient will have their own filter 501 and patient interface 601.

The package shown in FIG. 3 will be provided for a first patient in a specified time period. The time period is one in which it is acceptable in a medical setting to re-use the inspiratory conduit 401, humidifier chamber 251, and gases delivery conduit 301.

A method of assembling a breathing circuit using the package of FIG. 3 would comprise, positioning the gases delivery conduit 301 upstream of the humidifier chamber 251 and downstream of a source of gas, and coupling the gases delivery conduit 301 to the source of gas (for example, by connecting the gases delivery conduit to a wall gases source such as gas port GP via a flow controller such as a flow control valve or a control knob) and to the humidifier chamber 251; positioning the humidifier chamber 251 on the humidifier base 201; positioning the inspiratory conduit 401 downstream of the humidifier chamber 251, and coupling the inspiratory conduit 401 to the humidifier chamber 251; positioning the filter 501 and patient interface 601 downstream of the inspiratory conduit 401, and coupling the filter 501 to the inspiratory conduit 401 and, if not already coupled, coupling the filter 501 to the patient interface 601; positioning the patient interface 601 on the patient; receiving gas at the humidifier 251 from the source of gas, humidifying the gas, receiving humidified gas at the filter 501 from the humidifier 251, and delivering the humidified gas from the filter to the patient interface 601. It will be appreciated that the steps of the method can be carried out in any suitable order or concurrently.

The assembled apparatus may be used to deliver gases to a patient during pre-oxygenation, when the patient is being anaesthetized and/or when the patient has been anaesthetized (i.e. during the apnoeic window). For example, the apparatus may be used to deliver heated, humidified, high flow gas at between 5 l/min and 150 l/min, and advantageously at least at about 70 l/min, but may also be at least about 50 l/min, when a patient has been anaesthetized. When a patient has been anaesthetized, their respiratory drive is compromised and they are not breathing spontaneously. The high flow maintains the patient's oxygen levels at a safe level. This provides a useful alternative to a mask and bag that would typically be used to artificially ventilate a patient.

The method may additionally or alternatively be used when the patient is being pre-oxygenated prior to being anaesthetized. At that time, the patient is breathing spontaneously. Pre-oxygenation is carried out to increase oxygen concentration in the patient's lungs.

In both instances the temperature of the gases delivered to the patient may advantageously be about 37° C. and the humidity may be about 44 mg/l $H_2O$.

Connecting Same Kit to Subsequent Apparatus

Once the medical procedure on the first patient has been completed, the filter 501, and thereby the patient interface 601, will be decoupled from the inspiratory tube 401. The filter 501 and patient interface 601 can then be discarded. Alternatively, if it is expected or apparent that the patient will require further respiratory support, the patient interface 601 could remain in place on the patient, and the filter 501 that is coupled to that patient interface 601 could then be coupled, either directly or indirectly, to another source of gas. Alternatively, the filter could be removed if not being used or if no further connection with reusable components is required. For example, the other source of gas may be provided elsewhere in the medical facility, such as in a recovery room following a surgical procedure.

Subsequently Connecting Another Kit to Same Humidifier/Inspiratory Conduit

After the first filter 501 has been decoupled from the inspiratory conduit 401, a further apparatus comprising a new filter 501 and new patient interface 601 can be coupled to the inspiratory conduit, to enable the gases delivery conduit 301, humidifier chamber 251, and inspiratory conduit 401 to be used on a subsequent patient. In particular, a user will position the new filter 501 downstream of the inspiratory conduit 401, and will couple the filter 501 to the inspiratory conduit 401. If not already coupled, the user will couple the filter to the patient interface. The method will then involve positioning the new patient interface 601 on the patient; receiving gas at the humidifier 251 from the source of gas, humidifying the gas, receiving humidified gas at the filter 501 from the humidifier 251, and delivering the humidified gas from the filter to the patient interface 601. It will be appreciated that the steps of the method can be carried out in any suitable order or concurrently.

A similar process of decoupling the used filter 501 and patient interface 601 from the inspiratory conduit 401, and then coupling a new filter 501 and thereby a new patient interface 601 to the inspiratory conduit 401 can be repeated for subsequent patients.

At the end of a specified time period (for example, one day), the humidifier chamber 251, gases delivery conduit 301, and inspiratory conduit 401 can all be decoupled and discarded, and a new package as shown in FIG. 3 can be provided and used for the next time period.

Because the gases delivery conduit 301, humidifier chamber 251, and inspiratory conduit 401 can all be used multiple times on multiple patients (due to the presence and location of the filter 501), most new patients will only require a new filter 501 and new patient interface 601. Those two components will be provided as a kit in a package that comprises a sealed container or bag. The package may, for example, be a clam shell package. The container or bag may be airtight, and its contents may be sterile. The container or bag will contain the filter 501 and the patient interface 601. Such a package is shown in FIG. 4.

Figure 4:
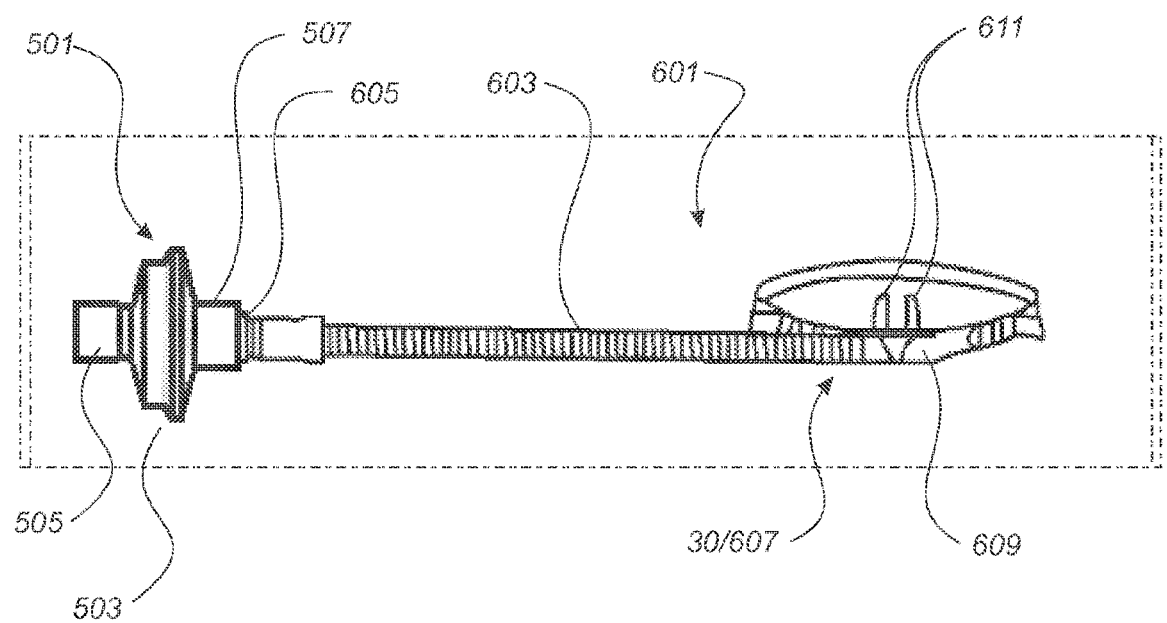
FIG. 4 shows components of a second configuration kit or apparatus for use in the respiratory therapy system.

The patient interface 601 and filter 501 may be provided separately in the package of FIG. 4. Alternatively, the patient interface 601 and filter 501 may be coupled in the package. Alternatively, the filter may be integrally formed with the patient interface gases tube of the patient interface.

The use of the patent interface 601 and filter of the package of FIG. 4 will be as described above.

The patient interface 601 and filter 501 will be used with a single patient or user, but may be used to deliver gases from one or more apparatuses; for example, for one patient prior to and/or during an anaesthetic procedure and/or during post-operative recovery.

Another kit may comprise a gases delivery conduit 301, an inspiratory conduit 401, and a humidifier chamber 251, but no filter 501 or patient interface 604. Again, this kit may be provided in a package such as the type described above, and the components may be coupled together or provided separately.

The different types of kits may be provided together or separately. For example, a single package may be provided with two or more of the kits of the same or different types therein.

Exemplary Filter

FIGS. 5 to 6D show an exemplary filter 501 that can be used in the described apparatus. Referring to FIG. 5 the filter has a filter housing F1 formed from a first housing part F2 and a second housing part F3. The first and second housing parts F2, F3 are joined at their respective peripheries F4, F5. The peripheries F4, F5 of said first and second parts F2, F3 clamp therebetween the peripheries F6 of a web F7 of filter material. The first and second housing parts F2, F3 each include one of an inlet port F8 and outlet port F9. The inlet and outlet ports are essentially indistinguishable and interchangeable. An insulating outer wall F10 is provided in the form of a cover which covers the main filter media enclosing body of the filter housing F1.

The filter housing F1 and the surrounding outer wall F10 form therebetween a pair of closed air spaces F11, F12. These closed air spaces F11, F12 insulate the filter housing F1 from the ambient conditions outside the surrounding outer wall F10. The surrounding outer wall F10 is formed by a pair of cover sections F13, F14 which at their periphery F15, F16 have a "snap fit" connection with one another. Each cover section F13, F14 has a respective collar F17, F18 which fits over the inlet port F8 or the outlet port F9 respectively. Each collar F17, F18 has an extension F19, F20 thereof extending towards the web F7 of the filter media to abut against a face F21, F22 of the respective housing parts F2, F3 extending outwardly from the ports F8, F9 in a direction towards the web F7 of the filter media.

In viewing FIG. 5 it will be appreciated that in the form shown the filter is rotationally symmetric, so the cross section on any longitudinal plane will look like that in FIG. 5. It would of course be possible to construct the filter to have a more rectangular shape, e.g. of the web F7 of filter media and the associated peripheries F4, F5 of the housing parts F2, F3, with the wall F21, F22 merging between the rectangular shapes of the peripheries F4, F5 and the circular peripheries of the inlet and outlet ports F8, F9.

In some applications it may be preferred that the filter have more than one port on one or more of the sides of the filter media, for example, two ports on what is a gas supply side of the filter media and a single port on what is a patient side of the filter media. In such case the two ports may for example be side by side or alternatively be coaxial ports for connection to a coaxial tube or splitting connector. In a coaxial arrangement the configuration of the filter housing and the insulating cover may be simply that as shown in FIG. 5. In a side by side configuration the respective filter housing part will have a pair of ports and the respective cover section a pair of apertures or openings therethrough to fit closely over the pair of ports.

The major components of the filter, excluding the filter media, may be formed from a suitable plastics material, and in particular one approved for medical uses. For example these, the first and second housing parts F2, F3 and the cover sections F13, F14, may be injection moulded from a medical grade polypropylene material. The filter media may be varied according to the intended application to include, for example antimicrobial properties or simply to be a particle filter. In this latter role the filter material may, for example, be a non-woven felt of electrostatically charged polypropylene fibres, such as that marketed under the trade mark ELECTROSTAT by All Felt Incorporated. A further alternative example of an appropriate filter media may, be a pleated sheet for example made of glass microfiber, or paper, or any other filter media types disclosed herein.

Further examples of filter media types comprise of: ceramics, fabricated metals (e.g. woven wire cloth), porous plastics (such as, but not limited to, plastic powders moulded into porous rigid shapes), non-woven media (e.g. dry-formed, wet-laid or membrane).

While further examples of filter media materials may comprise of: Cellulose, cotton, wood pulp, glass, fibreglass, glass micro fibre, or composites; polymers, such as polytetrafluoroethylene PTFE, polycarbonate (PC), acrylics including modacrylics, rayon, fluoropolymers, thermoplastic polyurethane (TPU), polyethylene (PE), polyamides, polyester, polypropylene (PP), nylon, metals, such as galvanised steel, stainless steel, aluminium, copper.

Composites may consist of polyamides, polyethersulfone, polysulfone, ceramic, carbon or any of the other polymers listed above, such as polytetrafluoroethylene PTFE, polycarbonate (PC), acrylics, rayon, fluoropolymers, thermoplastic polyurethane (TPU), polyethylene (PE), polyamides, polyester, polypropylene (PP), nylon. The composite may be a composite because it is of a multi-layer construction. Separate layers may have different functions, for example support or strength layers, different filtration efficiencies or pore sizes, for the absorption of gases, to contain particles and/or contaminants in the inner or different layers of a composite filter.

It will also be appreciated the filter media may be or comprise of electrostatic, hydrophilic or hydrophobic characteristics or properties.

Connection between the first and second housing parts F2, F3 may be performed by a permanent bonding process to ensure a suitable seal between the two parts. To that purpose the first and second parts F2, F3 have overlapping flanges F24, F23 respectively and these flanges provide surfaces which may be joined by a suitable adhesive or by ultrasonic welding in a known fashion. To grip the periphery F6 of the web F7 of filter media between the peripheries F4, F5 of the first and second housing parts F2, F3 a suitable ridge or ridges F25 may be provided on one (in this case the second housing part F3) of the housing parts F2, F3.

In use the filter may be connected between the inspiratory conduit 401 and the patient interface 601 between two lengths of breathing circuit, as discussed above. The patient interface tube 603 may, for example, be a breathable tube to prevent or remove condensation and to enable the delivery of gases to the patient at approximately 37° C. With the enclosed space F26 within the filter 501 being substantially insulated from the ambient conditions outside the outer wall F10, condensation forming within the filter on the filter walls will be substantially reduced. In one optional configuration, one or more apertures (not shown) may be provided at a location F50 in the walls F21 and/or F22 of the housing parts F2, F3 adjacent the periphery flanges F4, F5 thereof such that if sufficient such holes are provided any liquid gathering in the spaces F26 will flow through the apertures and into the air pockets F11, F12.

The insulated filter 501 is of a simple construction. This construction is demonstrated with respect to FIGS. 6A to 6D. The filter involves five simple components being the first and second housing parts F2, F3, the web F7 of the filter media and the cover sections F13, F14 forming the outer wall. The first step of assembly is depicted in the cross sectional side elevation of FIG. 6A. The housing parts F2, F3 are brought together in the manner indicated by arrows F26, F27 to clamp the peripheries F6 of the web F7 of the filter media between the outwardly extending peripheral flanges F4, F5 of the housing parts F2, F3. Annular projecting ribs F25 on the forwardly facing surface of the peripheral flange F5 of housing part F3 grips the periphery F6 of the web F7 of filter material and squeezing same against the periphery flange F4 of housing part F2. The assembled filter housing is thus shown in the side elevation of FIG. 6B. In the condition thus shown the periphery flange F28 of the housing, formed by the periphery flanges F4, F5, is subject to ultrasonic welding to firmly and sealingly bond together the housing parts F2, F3.

Referring then to FIG. 6C, a first cover section F13 is introduced having a collar F19 thereof passing over or around the inlet port F8 of the filter housing F1. A second cover section F14 is introduced to have collar F20 thereof pass over and around outlet port F9. The first and second cover sections F13, F14 are brought together in the direction as indicated by arrows F29, F30 such that the forwardly facing peripheral flanges F15, F16 overlap and the complementary engagement surfaces formed thereon inter-engage to connect the cover sections F13, F14.

The completely assembled filter including insulating cover is depicted in the side elevation of FIG. 6D.

According to the description herein, and when provided either in combination with those embodiments described herein, or when provided independently of those, there is disclosed a further filter arrangement 701 for use in a respiratory support system for delivering gas to a user or patient. Such a filter arrangement 701 as shown in FIGS. 6E, 6F and 6N is of a similar configuration to the filter 501 which is described herein. As such, reference to the details of the filter 501 may be relied upon in relation to being additional details of the filter arrangement 701.

Such a filter arrangement 701 comprises a filter housing 703. The filter housing 703 has a gases inlet port 707 and a gases outlet port 705. At least one (or both) of the inlet and/or outlet ports 707, 705 is/are adapted for connection with another component 805 (such as a connector provided at a terminal end of a conduit) via one or more (more particularly there may be a pair) of male connection fingers 901. The male connection fingers 901 extend externally from one or both ports.

For example, the male connection fingers 901 can be configured to extend from the gases outlet port 705, or the gases inlet port 707, or from both ports 705, 707 of the filter arrangement 701.

As is more particularly shown by FIGS. 6E-6N, one or each of the gases inlet or outlet ports 707, 705 can include an adapter insert 900.

An adapter insert 900 is configured to facilitate a connection with another component, such as a connector located at the terminal end of a conduit, for example to a gases inlet port 605 of another component as illustrated in FIG. 4.

The adapter insert 900 comprises one or more (in particular a pair of) male connection fingers 901. The male connection fingers 901 extend from a first end 902 of the adapter insert.

The male connection fingers 901 can optionally comprise of indentations or recesses (or even whole windows) 915. These recesses 915 can be shaped for suitable engagement of a projection or protrusion 820 located or provided on another component 805 which is to receive the male connection fingers 915.

The adapter insert 901 comprises one or more retention members 903 provided at a second end 904 of the adapter insert 900. Each retention member 903 is configured to be substantially engageable with an interior surface portion 709 of the filter housing 703.

Each retention member 903 is configured for an engagement with the interior surface 709 of the filter housing 703 to retain the adapter insert 900 within a port (e.g. either of both of those ports indicated as items 707 or 705) into which the adapter 900 is to be inserted.

In use, each retention member 903 when engaged with the internal surface 709 of the filter housing 703 acts to resist axial displacement (such as detachment) of adapter insert 900 from being moved in a direction toward an exterior end 711 of a port into which the adapter insert 900 is located.

Each retention member 903 can be configured to include at least a hook or other surface projection to more positively engage or latch with the internal surface 709 of a filter housing 703.

In various embodiments, there may be one or more retention members 903, or a plurality of retention members 903, or there be two retention members 903 provided, or in yet other embodiments there can be four retention members 903.

A single retention member 903 may be provided. However, there may be more than one retention member 903 utilised, and in such instances, such retention members 903 can be arranged symmetrically around the second end 904 as a series or sequence of formations or may together form an array about the second end 904, which in turn provide for an array of retainers engageable with an interior surface 709 of the filter housing 701.

Extending between the first end 902 from which the male connection fingers 901 extend, and the second end 904 from which the one or more retention members 903 extend, is a shank portion 905. The shank portion 905 connects the first end 902 with the second end 904.

The shank portion 905 includes a lumen or gas flow path 912 for the passage of gases therethrough between each of the first and second ends 902, 904. In particular embodiments, the gas may flow in a direction from the second end 904 to the first end 902.

The lumen or gas flow path 912 can be configured and/or be internally shaped so as to transition from a substantially wider bore (or larger internal diameter) at the second end 904 of the adapter insert 900 to a substantially narrower bore (or a smaller internal diameter) at the first end 902. In particular embodiments, the lumen or gas flow path 912 may transition in a substantially graduated manner or be of a substantially linear progression between the different bores or internal diameters between each end of the first and second ends 902, 904. Such a transitioned lumen 912 (or flow passage) can help to minimise or reduce resistance to flow of gases therethrough. A substantially smooth inner wall or surface of the lumen 912 can further assist with minimising such resistance to gas flow.

When the adapter insert 900 is located within a port of a filter housing, the shank portion 905 is advantageously substantially housed within or by that particular port. Located along or about the shank portion 905 may be one or more splines or ribs 906. In particular embodiments, the one or more splines or ribs 906 can extend longitudinally along the shank portion 905. In alternative embodiments, one or more of the splines or ribs 906 may be provided as circumferential (whether as a continuous or discontinuous feature) or radially extensive ribs. Whether the splines or ribs 906 are of a longitudinal or circumferential orientation, in some configurations the one or more splines or ribs 906 can extend a radial distance outward from the shank portion 905 so as to at least partially engage or make surface contact with an inside surface 907 of a port into which the adapter insert 900 is to be located.

The or each of the one or more splines or ribs 906 can be configured to provide at least some strengthening or structural support to the wall of a port into which the adapter insert 900 is to be located. This may be particularly useful in instances where the port from a filter housing may benefit from structural or strengthening, particularly when such a filter (and the filter housing) is being utilised for the purposes as disclosed herein.

The splines or ribs 906 can provide for a taper-type fitting of the shank into a port of the filter housing. In this way, such a taper-type fitting can help with an improved fit of the adapter insert into the port. The splines or ribs 906 can be tapered in a direction so that the there is a greater or larger tolerance between any such splines or ribs 906 and an internal surface (e.g. wall) of the port toward the second end of the adapter insert 904, and a much smaller tolerance (or tighter fit) between the splines or ribs 906 and the port wall or internal surface at the first end of the insert 902.

The splines or ribs 906 extending from the shank portion 905 may further assist in holding the adapter insert 900 in place relative to the filter housing port into which the insert is to be located and may also provide stability for the adapter insert.

In still further embodiments, the adapter insert 900 may additionally comprise one or more sealing members 908, or two or more sealing members, or in particular instances there may be two sealing members.

Advantageously, at least one first sealing member 908A may be provided about the shank portion 905. Such a first sealing member 908A can be provided about a circumference or a radial region of the shank portion 905. Such a first sealing member 908A facilitates a first sealing surface which extends radially outwardly from the shank portion 905. Where additional first sealing members are provided about or along the shank portion 905, these further first sealing members provide for additional sealing surfaces which may contact and/or form a seal with an inside surface 907 of a port into which the shank portion is to be housed.

As shown in the figures, the or each said first sealing member 908A is located intermediate of the first end 902 and the second end 904 of the adapter insert 900. In one particular embodiment, a first sealing member 908A is located substantially half-way along the shank portion 905, and provided as a circumferential seal of an o-ring type.

In another embodiment, the adapter insert 900 may provide for at least the first sealing member 908A provided about the shank portion 905 and at least a second sealing member 908B provided substantially at or adjacent with a first end 902 of the adapter insert 900.

The first sealing member 908A may help to account for any gaps between the shank portion 905 or the splines and ribs 906 and an inside wall portion of the port into which the adapter insert is to be located. In addition, the first sealing member 908A can help form a pneumatic seal between the adapter insert 900 and a port of the filter housing 703 by sealing against inside surface 907. Such a first sealing member 908A can provide for a more malleable seal than an interference fit on its own between the adapter insert and the port into which it is placed.

In one embodiment, the sealing members 908 may be positioned upon the adapter insert 900 by a suitably shaped recess or groove 908C. For instance, first sealing member 908A may be housed in a recess or groove 908C in shank portion 905 such that the two walls of the groove 908C secure the sealing member 908A in place. However, it will be appreciated alternative systems may be utilised as part of further embodiments for maintaining the orientation or positioning of the different sealing members 908 upon the adapter insert.

In another embodiment, the shank portion 905 of the adapter insert 900 may be sized to form a pneumatic seal with the inside wall portion of the port into which the adapter insert is to be located. The shank portion 905 can be sized as to form an interference fit with the insider surface 907.

At least one second sealing member 908B can be provided or located substantially at or adjacent with the first end 902 of the adapter insert 900. For example, in one embodiment, such a second sealing member 908B can be located or positioned to be substantially at or adjacent with a base 909 of the male connection fingers 901. The base 909 being at an end of said male connection fingers 901 which extends from the first end 902 of the adapter insert 900.

The second sealing member 908B can operate or acts to create a pneumatic seal with a surface of a female connector (for example, at least one or more of an inside surface, an end face or a chamfered-type face of the female connector when brought to bear upon the second sealing member.) The O-ring may be preferred over just an interference fit seal because of the higher pressure when put into engagement or surface contact with the second sealing member and/or the male connection fingers 901. Such a second sealing member can help provide for a better pneumatic seal with a female connector than an interference seal on its own, although an interference fit on its own is not precluded.

In further embodiments, the first end 902 of the adapter insert 900 may additionally comprise a radially extensive ledge or lip 910. In these embodiments, a second sealing member 908B can be located or positioned to be substantially upon an upper-side surface of the ledge or lip 910.

Such a ledge or lip 910 can extend radially outwardly so as to be of an outside diameter that is equal to or less than the outside diameter of a port within which the adapter insert 900 is to be located. The ledge or lip 910 can be of an outside diameter that is greater than an inside diameter of the port within which the adapter insert is to be located.

The particular maximum outside or external sizings or dimensions of the adapter insert 900 (exclusive of the first sealing member 908A) may help and mean that even if the adaptor insert 900 were to be put into connection with filter housing port, a 22 mm female taper connection or another component can fit over the adapter insert 900 and onto the outside surface of the port to which the adapter insert is housed or located in-use (for example, in this situation, the outside diameter of the filter housing port would effectively be working as a 22 mm male taper fitting). In emergencies, this can mean that other systems can be connected to the filter housing quickly and without having to remove the adaptor insert itself.

An underside surface 911 of said ledge or lip 910 is enabled for contact with a terminal end face (such as that surface labelled as item 713) of the port within which the adapter insert 900 is to be located.

Accordingly, the underside surface 911 may perform as a stop end surface to prevent an over-insertion of the adapter insert 900 into the filter housing 703 through a port. Similarly, the retention members 903 can perform as stop ends or other features for preventing the inadvertent removal or detachment of the adapter insert 900 from a port into which it is inserted. In this manner, the adapter insert 900, once provided in connection or retention with the component or port into which it is insert, may be permanently retained or attached.

In various arrangements, a distance between the underside surface 911 of the ledge or lip 910 and a retaining member 903 can match or may be substantially equal to the length of the port into which the adapter insert is to be located.

The ledge or lip 910 can be interposed, or may be sandwiched, between an end of the shank portion 905 and a first end 902 of the adapter insert 900. Alternatively, the ledge or lip 910 may be sandwiched between the base 909 of the male connection fingers 901 and an end (e.g. the first end 902) of the shank portion 905. In particular configurations, the at least one second sealing member 908B is sandwiched between the base 909 of the male connection fingers 901 and an end of the shank portion 905. Alternatively, the at least one second sealing member 908B may sandwiched between the base 909 of the male connection fingers 901 and an upper-side surface of the ledge or lip 910.

Advantageously, when used, the at least one second sealing member 908B provides for a second sealing surface for sealing with a surface of another component (such as a connector or a port of another connector) when brought to bear upon the second sealing surface. The or each second sealing member 908B can be of an o-ring type.

In relation to the second sealing member 908B, when another component is brought into connection or engagement with the male connection fingers 901 and, in use, when such a connection or engagement is made between these, the another component may be configured to additionally engage with the second sealing member and its provision of a second sealing surface. In this manner, the second sealing member can operatively assist with a pneumatic connection being made between the adapter insert and the another component. This can help with improved pneumatic connections, reduction in loss of gas from the breathing circuit and the associated benefits of improved/maintained delivery of a desired therapy to an end user or patient.

The adapter insert 900 as described herein, and when considered exclusive of a first sealing member(s), may have a maximum radial outside diameter (or external profile) which is equal to or less than 22 mm.

The above embodiments and configurations therein gives reference to 'another component'. Such 'another component' may be any other suitable component to which a connection may be made, particularly as part of a medical breathing circuit. However, it is contemplated that particularly preferred is for the 'another component' to be an end connector provided as a part of another section of a medical breathing circuit.

For example, FIG. 6N illustrates an exploded perspective view of a filter housing 703, an adapter insert 900, and an another component 805. FIGS. 6E and 6F illustrate a filter housing with an adapter insert in-situ (only the side of the ledge or lip 910 being observable in FIG. 6F) and a connection made with an another component 805. FIG. 6E is a cross-section view through FIG. 6F.

Each of FIGS. 6G-M illustrate the adapter insert 900 independently.

Figure 6G:
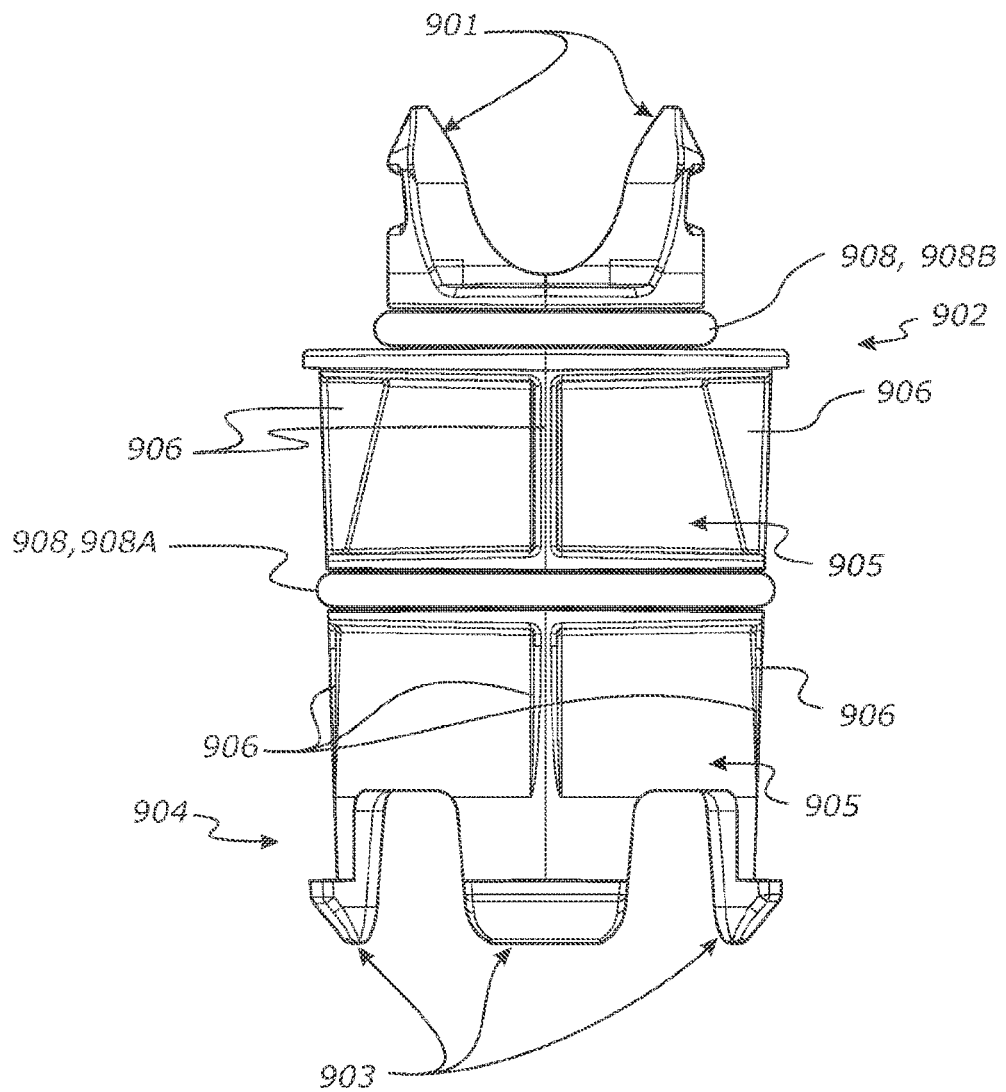
FIG. 6G is a side view of an adapter insert, inclusive of sealing members.
Figures 6H, 6I:
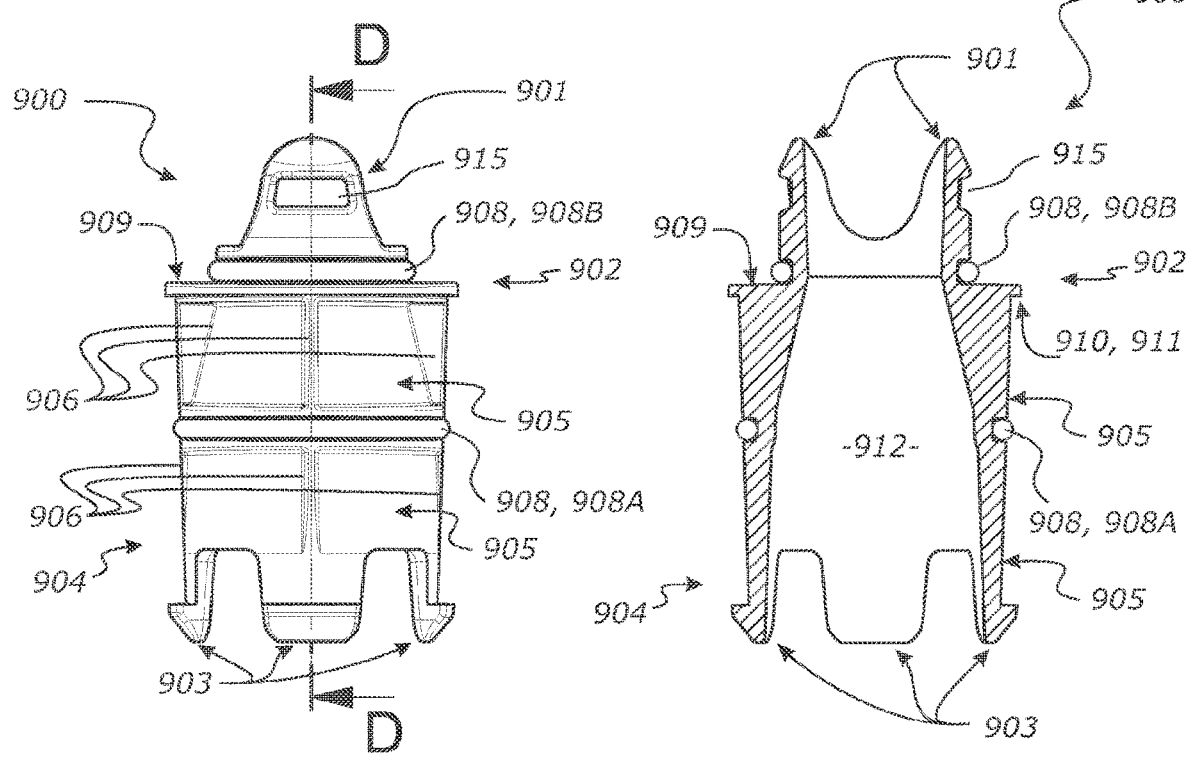
FIG. 6H is the adapter insert of FIG. 6G, rotated through 90°.
FIG. 6I is a cross-sectional view of the adapter insert of FIG. 6G.

For example, FIG. 6G is a first side view of the adapter insert 900, which includes a single first sealing member 908A and a single second sealing member 908B. FIG. 6I is a cross-sectional view of FIG. 6G which helps illustrate the relative positioning of different sealing members 908. FIG. 6I is also a cross-sectional view of FIG. 6H along D-D. FIG. 6H is a view of the adapter insert 900, axially rotated through 90° from that of FIG. 6G.

Figures 6J, 6K:
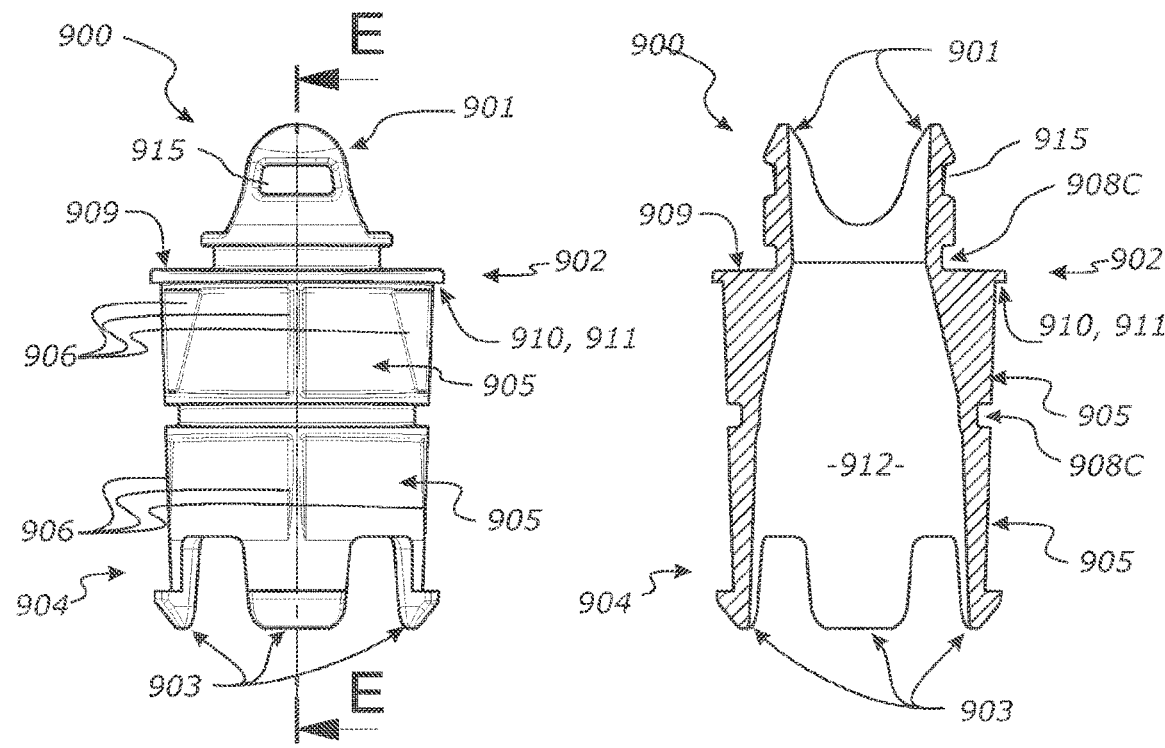
FIG. 6J is a side view of an adapter insert, exclusive of sealing members.
FIG. 6K is a cross-sectional view of the adapter insert of FIG. 6J.

FIG. 6J illustrates the adapter insert 900 in the same orientation as that of FIG. 6H, yet helps show the insert 900 prior to sealing members 908 being put into place. FIG. 6K illustrates the same adapter insert 900 as that of FIG. 6J, yet is axially rotated through 90°. FIG. 6K is a cross sectional view of FIG. 6J along E-E.

Figure 6L:
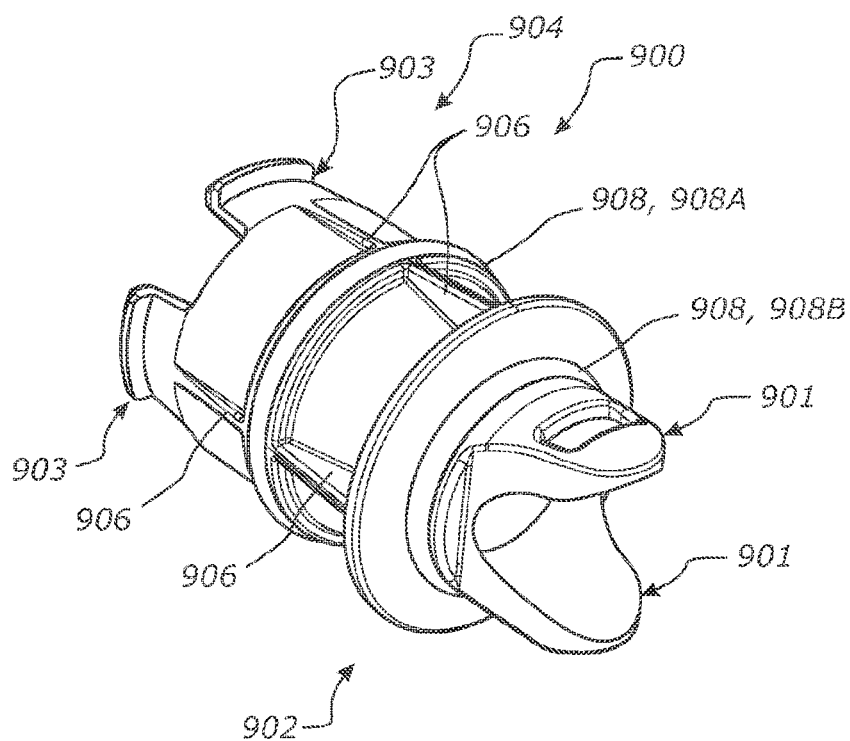
FIGS. 6L and M are different end perspective views of an adapter insert.
Figure 6M:
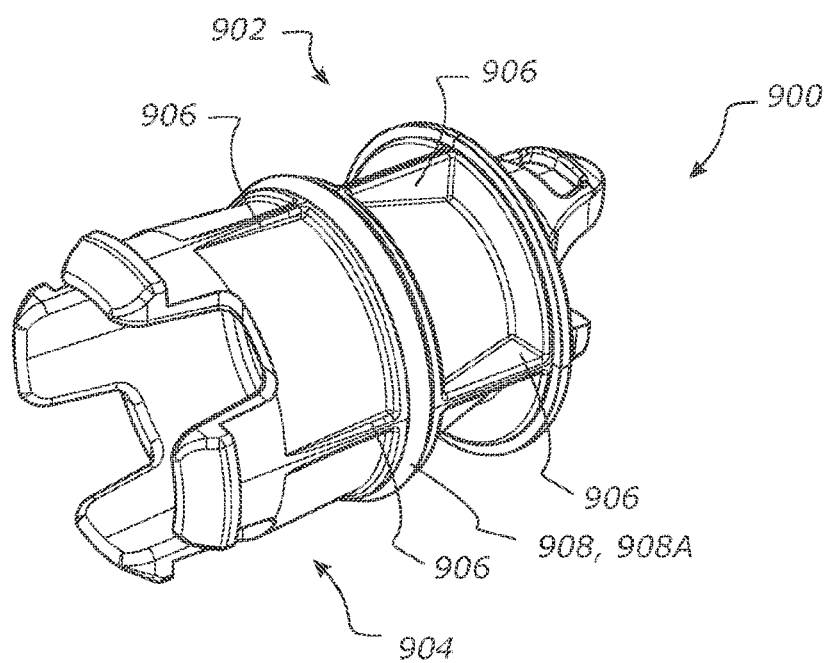
FIG. 6E is a cross-sectional view through FIG. 6F.
FIG. 6F illustrates an arrangement in which a filter housing has an adapter insert located within a port, and another component is made in connection with the adapter insert.
FIG. 6N is an exploded perspective view of the parts shown mated or engaged (or in connection with each other) of FIGS. 6E and 6F.
Figure 6N:
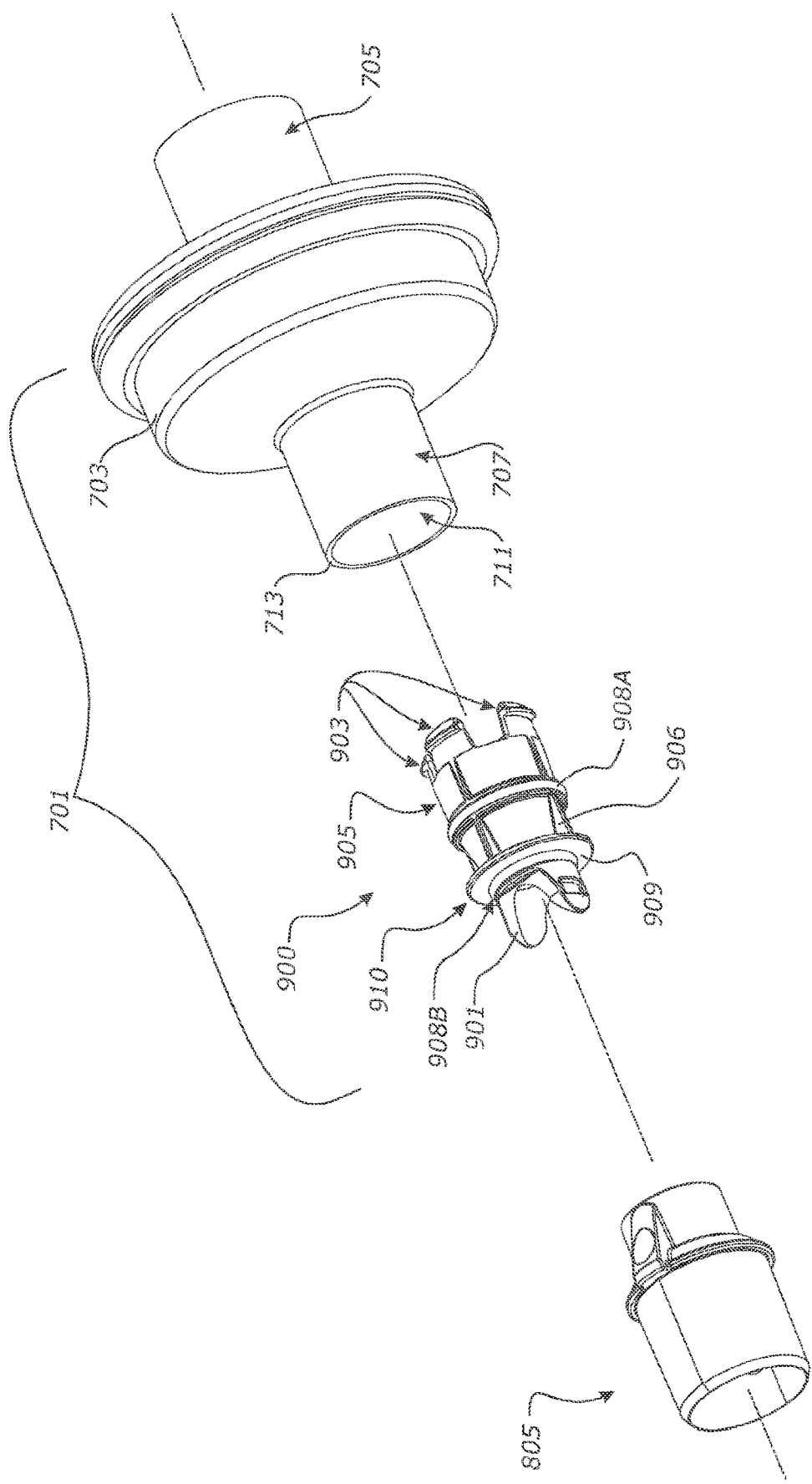

Each of FIGS. 6L and 6M illustrate an adapter insert 900 in different end perspective views.

An adapter insert 900 such as has been described herein can be put into engagement with a port of a variety of different components, in particular however, provision of an adapter for a filter housing is desired. The provision of such an adapter allows for an in-line connection to be made with the filter body by a component of a breathing circuit. Accordingly, an in-line filter can be more readily and easily (as well as accurately and pneumatically) put into the gas flow path of a medical breathing circuit.

Exemplary Nasal Cannulae

FIGS. 7 to 21 show exemplary configurations of nasal cannulae that can be used in the patient interfaces 601 of the apparatuses described herein. It will be appreciated that the filter 501 will be provided upstream of the nasal cannula and downstream of the inspiratory conduit.

The nasal cannula assembly provides a patient with a patient interface suitable for the delivery of high airflow, high humidity gas flow to the patient's nasal cavity. The nasal cannula is useful in the anaesthetic context, because the cannula has a relatively small footprint and is positioned on the upper lip, leaving the mouth and throat free for a surgeon to insert additional instruments with minimal obstruction or interference or to perform procedures on the mouth/throat with minimal obstruction or interference. For patients to accept use of nasal cannula under these circumstances the cannula need to be unobtrusive, comfortable to wear, noise free, suitable for wearing while sleeping. The cannula may also be used for other therapies such as for Continuous Positive Airway Pressure (CPAP) therapy and the like.

Figure 7:
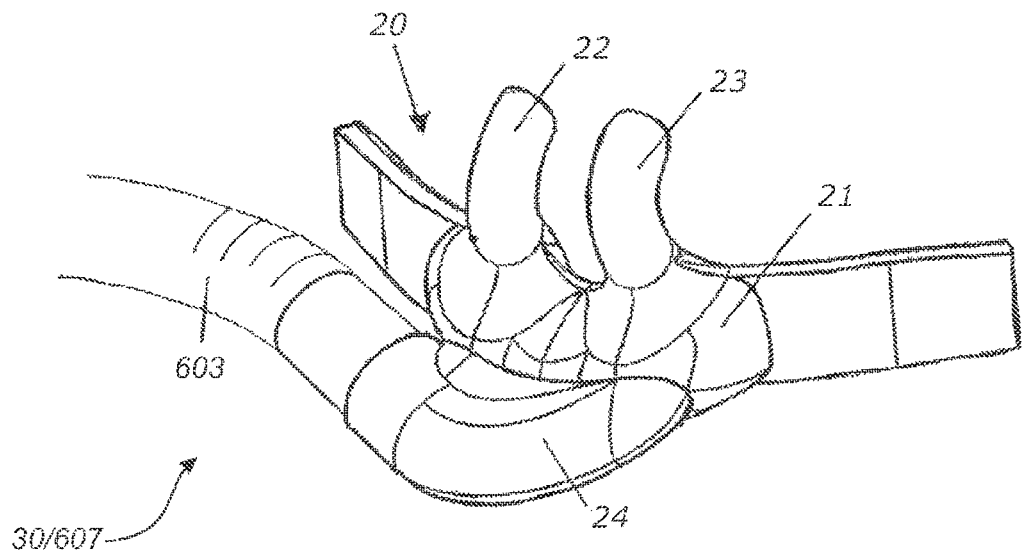
FIG. 7 is a perspective view of a first exemplary form nasal cannula assembly for use in the kit or apparatus.
Figure 8:
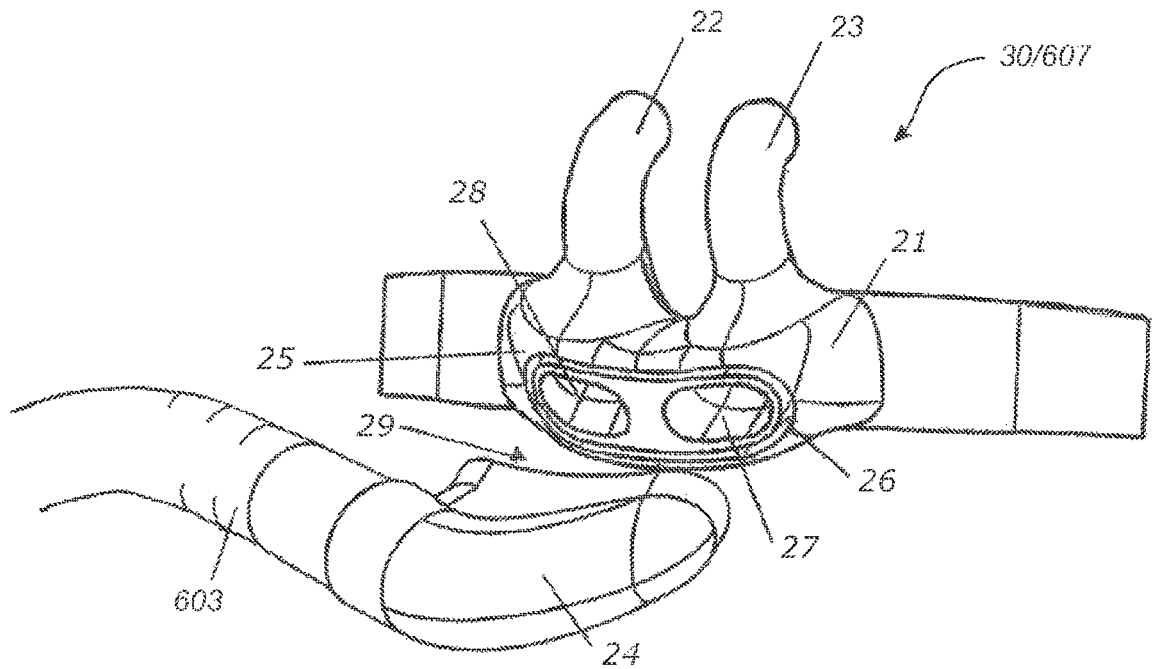
FIG. 8 is an exploded perspective view of the first form of the nasal cannula assembly of FIG. 7, showing two parts making up the nasal cannula, a face mount part and gases flow manifold part attached to tubing supplying gases to the patient.
Figure 9:
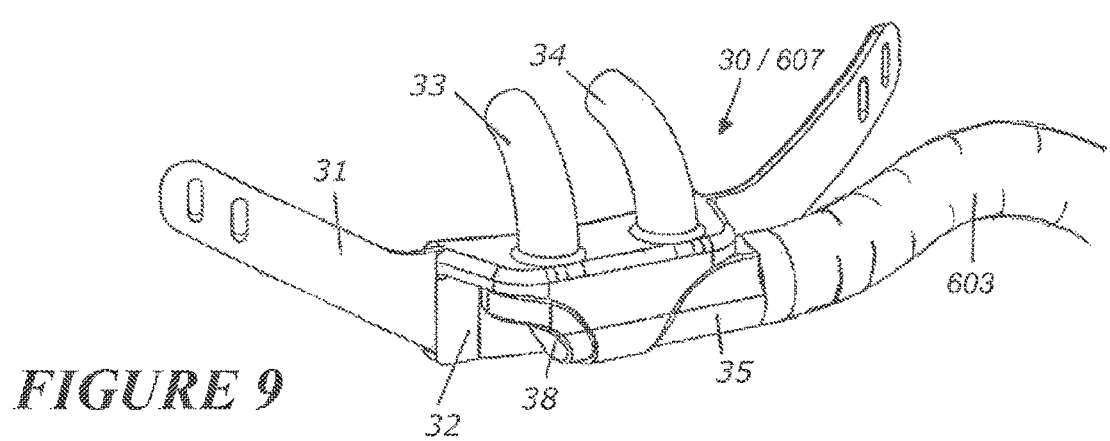
FIG. 9 is a perspective view of a second exemplary form nasal cannula assembly for use in the kit or apparatus, showing tubing providing a gases supply to a gases flow manifold part and face mount part when in connection.
Figure 10:
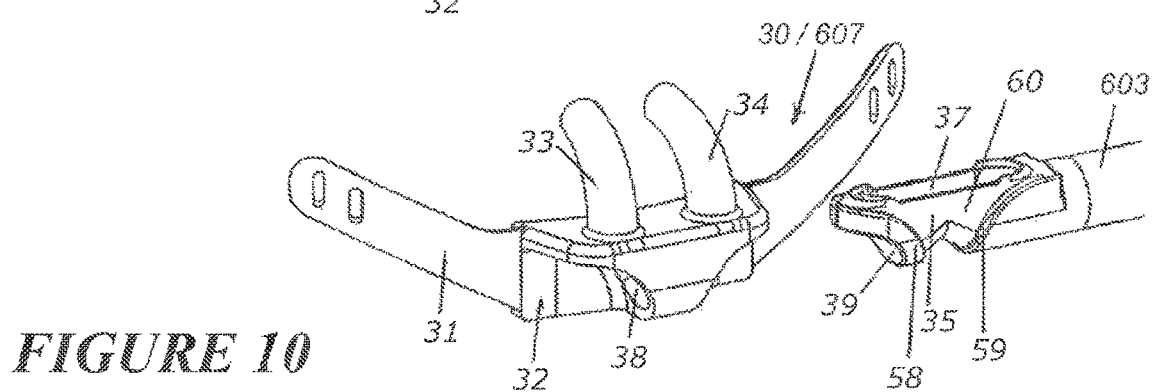
FIG. 10 is a perspective view of the second form of the nasal cannula assembly of FIG. 9 where the gases flow manifold part is disengaged from the face mount part.
Figure 11:
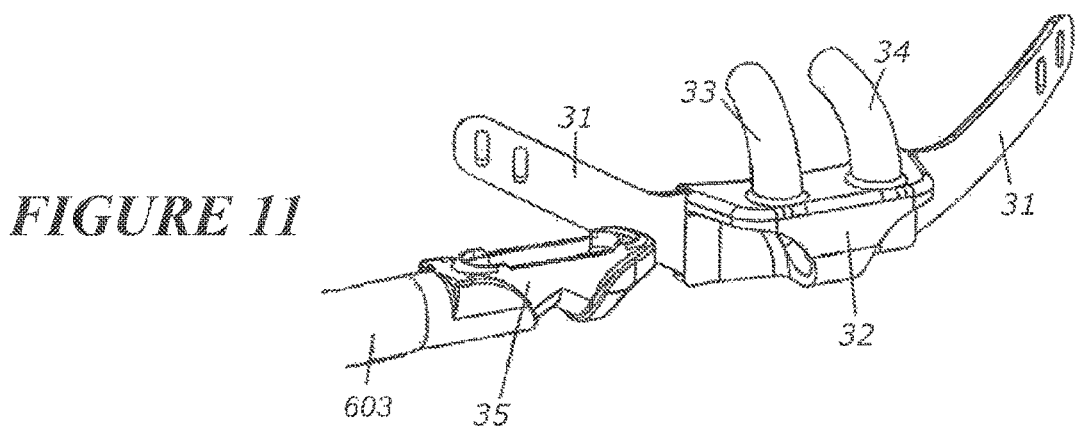
FIG. 11 is a perspective view of the second form of the nasal cannula assembly of FIG. 9 where the gases flow manifold part is disengaged from the face mount part, showing the manifold part can be fitted to either side of the face mount part.

A first form of the nasal cannula assembly 30/607 is shown in FIGS. 7 and 8. This nasal cannula, generally indicated as 20, comprises a face mount part 21 including a pair of tubular nasal prongs 22, 23 integrally molded with or removably attached to the face mount part 21, and a gases flow manifold part 24 that is integrally molded with or attached to tubing 603, such as that described above.

As described above, a nasal cannula can be provided with a removably attachable manifold for delivering the flow of gas to the interface, the manifold able to be re-oriented so as to have a gas supply connection put to either a left or a right side of the interface (or the patient). One or pair of side arms of such a nasal cannula allow for the positioning of the interface on a patient's face and may optionally include a relatively soft outer material or overmoulded material in at least the patient contacting surfaces.

The removable manifold may be re-oriented as previously described. Such a re-orientation can be manually done by a user or a person assisting the patient/user.

A headgear as disclosed herein may be provided in combination with the nasal cannula and may include at least one strap of which is bifurcatable (i.e. may have a line of weakness or other pre-defined zone allowing a user to separate the strap into two parts).

The body of the nasal cannula may include a barrel shaped portion into which the manifold is inserted and can be removed therefrom to allow for side swapping. The nasal cannula may additionally or optionally include headgear connectors that connect to one or both side arms.

The face mount part 21 and prongs 22, 23 may be moulded from silicone or other flexible material as is known is the art of cannula construction. The gases flow manifold part 24 may be made from a hard plastics material, although it may be manufactured in other suitable materials.

The face mount part 21 may be integrally molded with the prongs 22, 23 and is shaped to generally follow the contours of a patient's face around the upper lip area. The inner side (not shown) of the face mount part 21 may be provided with a breathable pad, to be described below. The outer side 25 of the face mount part 21 has moulded in it an elongated oval recess 26 and two oval recesses 27, 28 that extend through the face mount part 21 and each meet the tubular passageway's formed within each of the tubular prongs 22, 23.

The gases flow manifold part 24 is generally tubular in shape having a substantially circular inlet (not shown) on one side that curves around to an elongated oval outlet 29. The circular inlet receives the end of the conduit or tubing 603, so that gases are supplied to the gases flow manifold part 24 and are able to flow through the inlet and out the outlet 29. The tubing 603 may be permanently fixed to the manifold part 24, or may be releasably attachable.

The outlet 29, being elongated and oval in shape, fits into the elongated recess 26 in a friction or snap fit engagement with the manifold 21, such that a substantial force is required to remove the manifold part 24 from the elongated recess 26. Further, as the face mount part 21 is flexible and the manifold part 24 made from a harder plastics material it is possible for the manifold part outlet 29 to be easily pushed or forced into the elongated recess 26. When the manifold part 24 is engaged with the face mount part 21 and in use, gases flow from the tubing 603, through the gases flow manifold part 24 out its outlet 29, into each of the oval recesses 27, 28, into each of the prongs 22, 23 and into the patient's nares.

The face mount part elongate recess 26 and manifold part outlet 29 are symmetrical in shape and configuration and therefore the manifold part 24 is capable of being switched or flipped such that the tubing 603 extends from either the left or right side of the patient's nares. This means that the nasal cannula assembly 20 and associated tubing 603 are relatively unobtrusive as the cannula 20 only requires a single horizontal side entry, not two entries.

The nasal cannula assembly is more comfortable to wear as it sits under the septum of the nose and supports the two nasal prongs. As the prongs are made in one moulding of a soft material such as silicone the prongs are easy to insert in the patient's nares and comfortable to the patient.

The face mount part 21 is contoured such that the pressure distribution within the face mount part 21 forces even airflows up each nasal prong in order to reduce whistling of the airflow.

Reference is now made to FIGS. 9 to 12 that show a second form of nasal cannula assembly. In this form the nasal cannula assembly 30/607 is of a substantially similar form to the first nasal cannula assembly of FIGS. 7 and 8, and has a face mount part 32, a pair of nasal prongs 33, 34, gases flow manifold part 35, and tubing 603. The face mount part 32 and pair of nasal prongs 33, 34 may be integrally moulded as one piece from a soft plastics material such as silicone, although in other forms the face mount part and prongs may be separate, but capable of attachment together for use.

The nasal prongs 33, 34 are tubular in shape and may be consistent in diameter but may be shaped to fit the contours of the human nares.

A strap or strap attachment means 31 may be integrally formed or attached to the face mount part 32 in order to enable the nasal cannula assembly 30/607 to be held in place about a patient's face.

The face mount part 32 has an open tubular recess 38 extending below the nasal prongs 33, 34 that is capable of receiving a gases flow manifold part 35 that is attached to or integrally formed with tubing 603. The tubular passageways within the nasal prongs 33, 34 extend through the face mount part and into the recess 38. The gases flow manifold part 35 is blocked at one end 39 but attached to the tubing at the other end and has an elongate opening 37 that acts as an exit for gases received from the tubing 603. Due to the flexible nature of the material the face mount part 32 is made from, and as the gases flow manifold part 35 is made from a hard plastics material, the gases flow manifold part 35 can be pushed through the tubular recess 38 in the face mount part 32 and the elongate opening 37 in the gases flow manifold part 35 meets with the tubular passageways of the prongs 33, 34. Therefore, in use, gases flowing through the tubing and into the gases flow manifold part 35 exit through the opening 37 and into the tubular passageways in the prongs 33, 34, then into the patient's nares.

In order to assist with maintaining the gases flow manifold part 35 within the manifold recess 38 the manifold part 35 is provided with an inner recessed portion 60 and contoured lip areas 58, 59. When engaged with the face mount part 32 the tubular body forming the recess 38 sits within the inner recessed portion 60 and the edges of the tubular body abut the lips 58, 59 formed on the manifold part 35.

Figure 12:
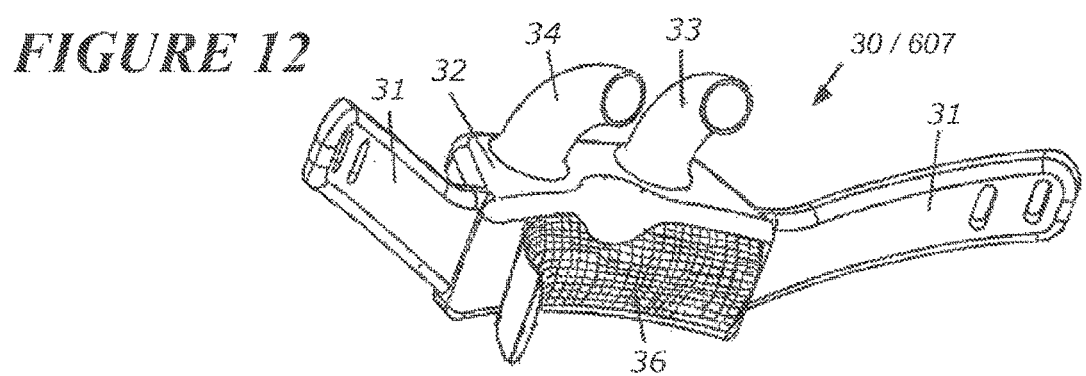
FIG. 12 is a back perspective view of the second form of the nasal cannula of FIG. 9, showing a removable breathable pad on the inner side of the face mount part that abuts the patient's face.

An optional breathable pad may be supplied with any of the nasal cannula assemblies described above. In particular, such a pad 36 is shown in FIG. 12 in the second form of the nasal cannula assembly as described above.

The pad may be attached to the inside surface of the face mount part 32 that connects with the upper lip of the patient wearing the cannula. The pad 36, which may be made from an absorbent cloth, reduces the incidence of heat and moisture on the patient's upper lip, where the face mount part 32 sits against their face.

The pad 36 may be attached to the face mount part 32 by adhesive, for example, the pad could be supplied with a sticky backing that adheres to the face mount part, so that the pad can be easily removed from the face mount part and replaced as necessary.

The pad, if provided, reduces the effects of heat against the patient's skin and improves hygiene, as any contaminants or cultures that may grow close to the patient's skin, in the warm environment can be removed on removal and replacement of the pad.

Referring now to FIGS. 13 to 16, a third form of the nasal cannula assembly is shown where the nasal cannula assembly comprises three parts.

Firstly, a gases flow manifold part 40 is shown in FIG. 13 which is designed for either left or right hand orientation and provides a symmetrical flow to a pair of nasal cannula assembly prongs 41, 42 (see FIG. 15 or 16).

Next, a pair of soft nasal prongs 41 or 42 are provided that are capable of being attached to the top of the gases flow manifold part 40 allowing for a large range of different shaped and spaced prongs to be available to the patient. Two such configurations of prongs 41, 42 are shown in FIGS. 15 and 16. The prongs 41 of FIG. 15 are narrow elongate tubular members 43, 44 of a substantially constant diameter that are fittable into a patient's nares. The prongs are integrally molded with a body 45 that is fittable with the gases flow manifold part 40 (see FIG. 13) by appropriate means, for example, friction or snap fit. The prongs 42 of FIG. 16 are tapered tubular members 46, 47 moulded to a body 48. Again, this body 48 is capable of being fitted (friction, snap or other) to the gases flow manifold part of FIG. 13. These prongs may be made from a soft plastics material such as silicon, although other suitable materials may be used.

With the prongs being removable they are easily cleaned and could also be disinfected for second or subsequent use for a particular patient.

The third part to the third form of the nasal cannula assembly shown in FIGS. 13 to 16 is the face mount part 49 of FIG. 14. The face mount part 49 comprises a head strap 53 attached to a pad 50, that may be a moulded or shaped substantially rigid pad, for example, made from a plastics material such as polypropylene. The pad 50 as shown in FIG. 14 may include a breathable cloth pad on its surface that abuts a patient's face, similar to that pad 36 described in relation to FIG. 12, or the head straps 53 may extend to sit behind the pad. The head strap 53 may be made from a flexible material, such as neoprene.

The plastic pad 50 is shown in FIG. 14 and has a plurality of apertures 61 formed into to allow for heat and moisture to dissipate from the patient's facial surface. The pad 50 has fastening means 51, 52 for holding the gases flow manifold part 49 in the correct position on the upper lip of the patient. The fastening means may be clips 51, 52 that are fittable into complimentary recesses 54, 55, 56, 57 provided in or on the manifold part 40 (see FIG. 13), but other appropriate fastening means may be provided with the cannula. An example of other fastening means is a loop that is integrally moulded as part of the prongs which wraps around the face mount part and latches over a protrusion on the manifold part thus encapsulating the face mount part and holding the assembly together stably and securely. Another example of a fastening means is a plastic Velcro™ type attachment where one side would attach to one side of the manifold part 40 and the other side to the plastic pad 50. For the fastening means shown in FIGS. 13 and 14 at least one recess must be provided on either side of the manifold 40. In the preferred form of the nasal cannula assembly two recesses 54, 55 are provided on one side of the manifold 40 and two other recesses 56, 57 on the other side of the manifold 40.

The attachment between the face mount part 49 and the manifold part 40 allows for either left or right hand orientation of the manifold part and associated tubing.

The cannula may be disposed after use. Alternatively, the cannula could be stored and the cannula subsequently re-used on a single patient, for example when a patient is moved from an operating room to a recovery room. The cannula can be removed and stored until it is needed in recovery. With a single flow entry cannula there will be less condensate due to the reduction in surface area for heat loss and thus the cannula reduces the effects of condensation building in the tubing and cannula.

Figure 17:
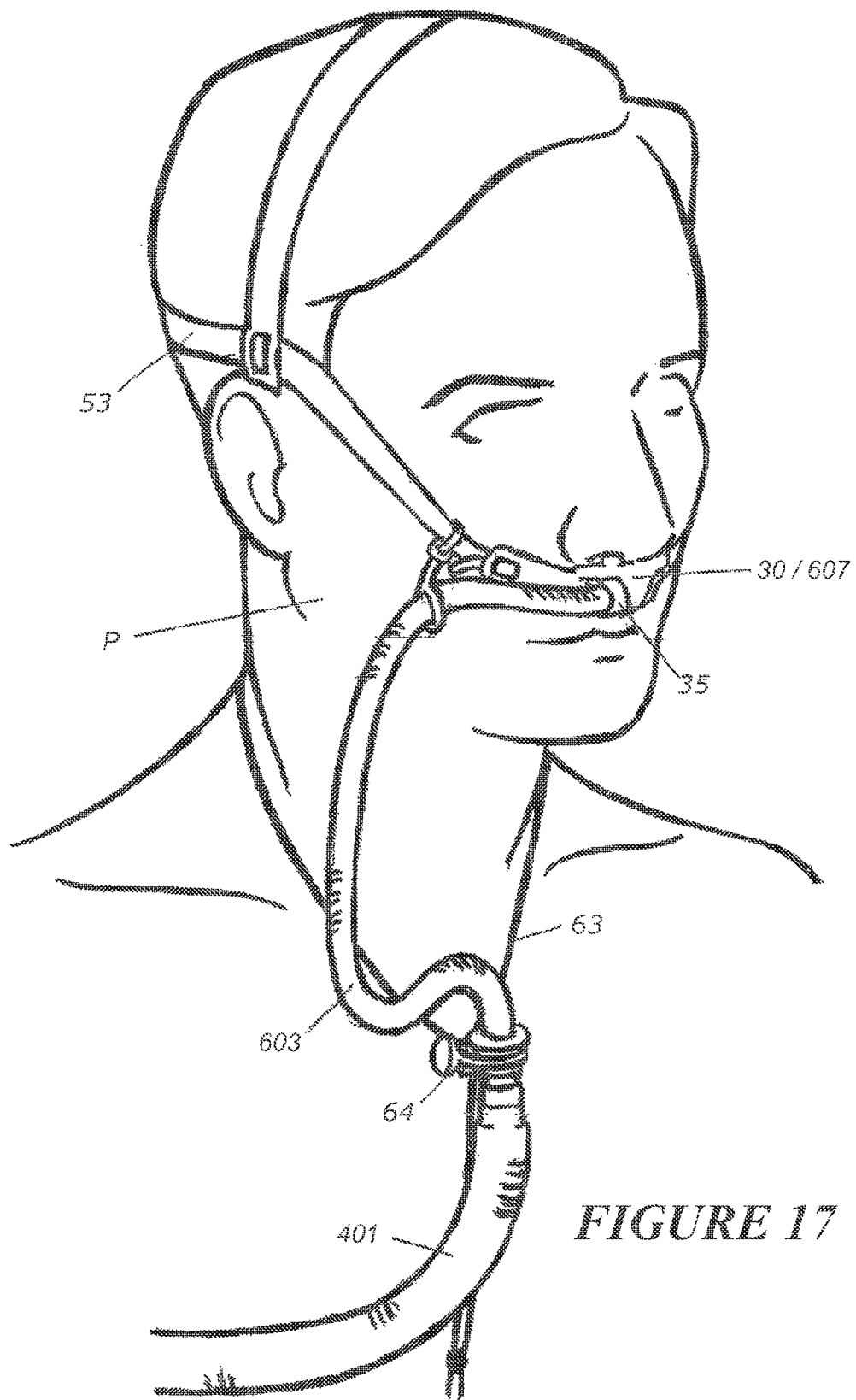
FIG. 17 is a perspective view of a patient wearing the nasal cannula assembly of FIG. 9, showing the use of a neck tie to take some weight of the tubing and a head strap assisting in the maintaining of the assembly to the patient's face.

Often an unheated flexible section of tubing is placed proximal to the patient to reduce torsion or pulling on the patient interface and reduce possible heat problems or over heating close to the patient. In order to reduce condensate forming in the unheated tubing, tubing can be provided that has vapour transmission properties. Referring now to FIG. 17 the nasal cannula (in particular that of the second form described herein) may be provided with a short piece of breathable tubing 603 between the nasal cannula 30/607 and heated inspiratory conduit 401. A filter will be provided between 603 and 401 as described above. The tubing 603 may be made from a material that allows for transmission of water, such as a hydrophilic material, for example SYMPA-TEX™.

Test results show the performance of a 420 mm length of breathable tube, operating with air input at an absolute humidity of 42.2 mg/L, an airflow of 10 litres per minute (LPM), in a room with ambient air at 22° C. and 50% RH, only lowered the absolute humidity to 41.15 mg/L at the exit of the dry tube. In comparison a 420 mm length of non-breathable but insulated polyethylene tube under exactly the same conditions also output air at 41.15 mg/L. In the breathable tube there was significantly less condensate measured, therefore, some of the humidity that would otherwise be lost as condensate on the wall is being transmitted through the breathable wall.

The result of providing the short section of breathable tubing 603 is that a majority of humidity in the gases is transported to the patient, and there is an insignificant and immeasurable loss of humidity through the breathable wall of the short tube 603, while condensate is reduced. The design of the high airflow high humidity system has been optimized to deliver a breathable gas treatment to patients at temperatures approximating body temperature and fully saturated with water vapour. The use of an unheated breathable conduit proximal to the patient to provide a connection that is highly flexible and avoids condensation by breathing would be expected to lower the humidity of the gas treatment thereby decreasing the efficacy of the treatment. These results are surprising and are counterintuitive and go some way to explaining why the use of a breathable tube as a short section of tubing before the patient has been overlooked. This short tube 603 is envisaged to be used with any tube delivering heated and humidified gases to a patient.

In an alternative configuration, a neck tie or lanyard may be provided with the nasal cannula assembly. FIG. 17 shows such a tie 63. The tie 63 may be connected to the tubing 401 or 603, or to the filter 501 (not shown in this Figure). A toggle 64 may be provided with the neck tie 63 in order to adjust the neck tie's length. The neck tie has the purpose of taking some of the weight of the tubing 401 and prevents the weight of the tubing 401 pulling on the nasal cannula assembly 30/607. This helps to prevent the prongs from interfering with the very sensitive lining of the nasal passages or from being dislodged. The loose fitting neck tie also provides a convenient way of connecting the tubing 401 to the patient outside the blankets. This allows the patient to turn in the bed and avoids the tubing 401 overheating if placed under the blankets.

The tie or lanyard described may be used with any breathing apparatus or interface that supplies gases to a patient; for example it may be used with a nasal or face mask or with a tracheostomy fitting or connector. When the tie or lanyard is used with such apparatuses or interfaces it takes the weight of the conduit(s) or tubing supplying gases to the mask, connector or cannulae and helps reduce the pull on the mask, connector or cannulae.

Figure 20:
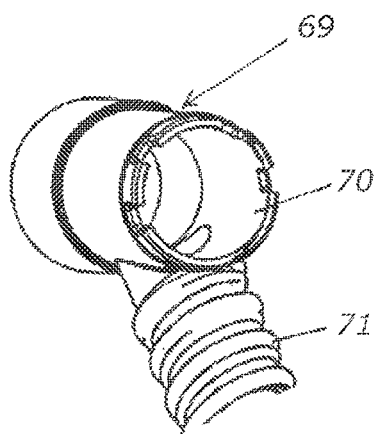
FIG. 20 is a perspective view of an exemplary tracheostomy fitting that could be used in the kit and apparatus instead of a nasal cannula assembly.
Figure 21:
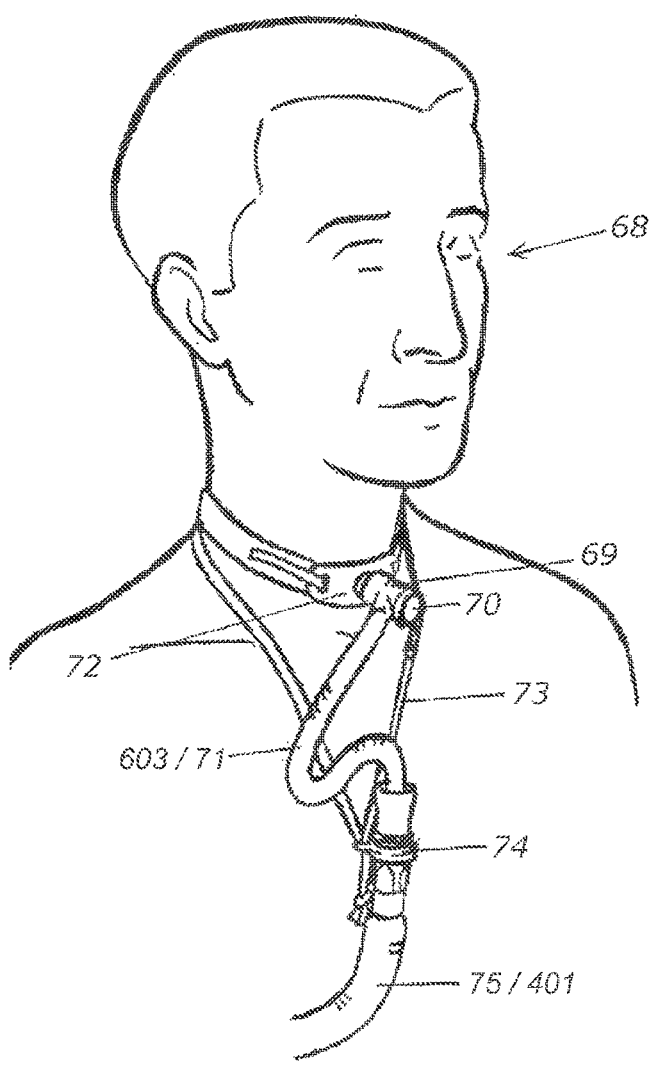
FIG. 21 is a front view of a patient with the tracheostomy fitting of FIG. 20 attached to a breathing supply where a neck tie or lanyard is used to support the conduit supplying gases to the patient

FIGS. 20 and 21 show a tracheostomy fitting or connector that may utilise a neck tie or lanyard. The tracheostomy fitting may be used as the patient interface in the kit and apparatus described herein, in place of the nasal cannula. Again, a filter, such as the filter 501, would be provided between the patient interface (in this case for example the tracheostomy connector 69) or the conduit 71 and the inspiratory conduit 401. In one particular example a particularly advantageous arrangement includes such a filter 501 being adapted by an adapter insert 900, thereby facilitating an ease of connection by the conduit 71 to the outlet of the filter 501. The tracheostomy connector 69 attaches to a tracheostomy mount 72 that extends into a tracheostomy tube (not shown) through hole in a patient's 68 neck and into their airway passages. The connector 69 provides a direct coupling of a tracheostomy tube to the breathing supply of gases received through a conduit 71. The conduit 71 may be constructed in a breathable material, similar to that described above, but may be a heated tube.

The connector 69 has the conduit 71 attached directly to it and also includes an expiratory port 70 to allow for expiration of gases. On inspiration no gases flow occurs out the port 70 due to the flow of gases to the connector 69 being greater than a patient's peak inspiratory flow. Therefore, there is also no or very little entraining of gases from the ambient air.

Excess weight on the tracheostomy tube may cause excess movement of the tube, with the risk of complications such as displacement or re-cannulation of the tracheostomy, the formation of granulation tissue or more seriously, stomal erosion. To obviate or reduce these problems a tie or lanyard 73 can be connected to the conduit 71 or additional connector 74 (that may for example connector the conduit 71 to an additional conduit 75 that supplies gases). The tie or lanyard 73 transfers the weight of the conduits 71, 75 and connector 74 from the tracheostomy tube or mount 72 and distributes it onto the neck of the patient leaving a minimal load directly on the tracheostomy tube or mount 72. The tie or lanyard 73 may be adjustable so that the tie or lanyard length can be altered to suit a patient's requirements. Alternatively, headgear can be used to retain the tracheostomy tube. The tracheostomy tube can be used to provide high flow therapy. In some configurations, the tracheostomy tube has a leaky connection with the patient to reduce the chance of barotrauma or over-pressurisation of the lungs when using high flow.

Orientation of a nasal cannula is an important requirement for patient comfort. If the nasal cannula is not held firmly in position, it can skew, placing unwanted load on the inside surfaces of the patient's nares. However, to overcome this head gear is often provided with nasal cannula, although, if the head gear is not tight the nasal cannula can still move. This type of tight tension can then compromise patient comfort with pressure on the head and face, while forcing the cannula further up the patient's nose. Ideally nasal cannula should attach to the patient's face in a secure manner, yet with low loading on the head and face.

Figure 18:
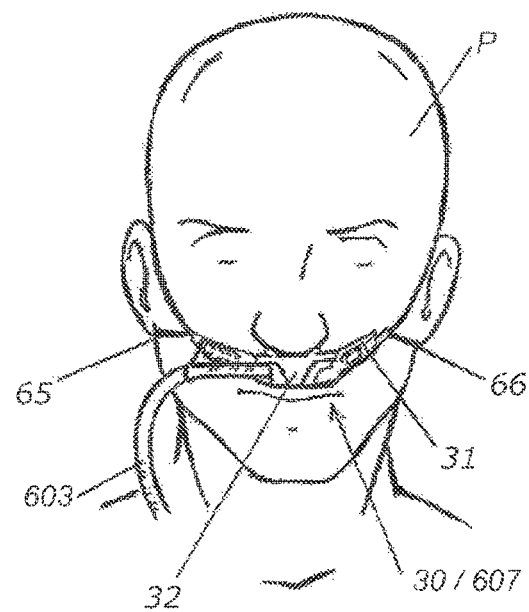
FIG. 18 is a front view of a patient wearing a nasal cannula assembly where the assembly is held to the patient's face with the assistance of ear loops.
Figure 19:
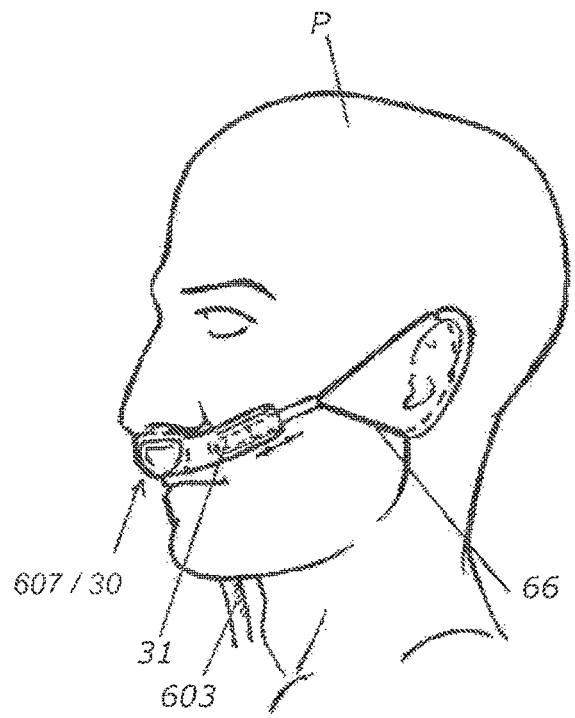
FIG. 19 is a side view of the patient and nasal cannula assembly of FIG. 18.

Referring to FIGS. 18 and 19 nasal cannula attachment means may be provided to hold the nasal cannula assembly 30/607 to the patient's face. The attachment means may be ear loops 65, 66 that are connected to the straps 31 of the face mount part 32 of the nasal cannula assembly 30/607.

The loops 65, 66 extend from the face mount part 32 around the patient's ears, and provide rigid anchoring when an inelastic material is used. The loops 65, 66 may be made from a thin, round cord with the ends captured in plastic, and may be adjustable. The plastic ends of the loops 65, 66 are inserted into purpose made cavities in the straps 31, enabling adjustment of length for a comfortable, yet firm fit.

In use, to fit the nasal cannula assembly, a first loop (for example, loop 65) is placed over one ear, the nasal cannula assembly positioned on the patient's face and in their nose, then the other ear is passed through the second loop (for example, loop 66), so both loops sit snugly behind the ears. This method of fitting the nasal cannula avoids the initial discomfort of gases being blown into the patient's eyes when the cannula assembly is pulled down the face for fitting with other headgear. Fastening the nasal cannula in this method provides an attachment means that is horizontally secure with minimum tension applied to the ear connection loops. The ear loops have the added advantage for a patient lying on their back that there are no straps behind the back of the head that are moved by head movement on the pillow.

The conduits described herein may be formed from tubing. The tubing configurations may be suitable to deliver gas at a high flow rate as described herein. For example, at flow rate of between about 45 and 150 liters per minute (LPM), or between about 10 and 120 LPM, or between about 60 LPM and about 80 LPM, or at about 70 LPM.

The complementary coupling features between the components of the apparatus could be any suitable form. For example, the features could be any one or more of push fits, interference fits, latch/catch-style fittings, bayonet-style fittings, and medical tapers or medical connections. In one example, the coupling features between all components may be a 22 mm medical taper. Soft seals, such as O-rings, may be provided between the ports of the components to provide a seal at the connections or connection points. Different types of coupling features may be used to connect different components, so that there is only one possible assembly configuration of the components in the system. In another form, the complementary coupling features may be provided, at least for one side of the coupling, by an adapter insert, such as that labelled as item 900.

The gas used in the configurations described above will typically be oxygen. Alternatively, the gas could be air or other suitable gas(es).

The liquid used in the configurations described above for humidification will typically be water. Alternatively the liquid could be other liquid(s) suitable for a humidification process.

The apparatuses, kits, and methods disclosed herein are particularly beneficial in an anaesthetic setting. The described configurations enable the same inspiratory conduit (and upstream components) to be used for a number of patients while only swapping out the patient interface/filter combination.

In an anaesthetic setting, the inspiratory conduit and patient interface need to be swapped for each patient due to an infection risk. In the anaesthetic process, the time of use of the inspiratory conduit is significantly shorter than for other ventilation applications. Ventilation may occur for days of therapy, while anaesthetic operations typically only last for a maximum of several hours. Hence, having the filter in-line with the cannula allows a user to re-use the inspiratory conduit (and upstream parts such as the humidifier chamber and gas delivery conduit) on subsequent patients. This is complementary to existing practice.

In an anaesthesia setting it is not uncommon to observe the anaesthetic breathing circuits, which attach an anaesthetic system to a patient interface, being reused between patients during a day of surgeries. A filter may be placed between the circuit and patient interface to minimise the risk of infection, with the filter and patient interface being replaced for each patient. A package or kit can be provided, as described herein, to provide for components to be used for such a circuit, with some components being individual to a particular patient (i.e. the components are only used by a single patient), yet other components (such as components upstream from such a filter, including but not limited to an inspiratory conduit and optionally a humidifier chamber).

With the advent of nasal high flow and its intended use in the anaesthesia setting via a respiratory breathing circuit separate to the anaesthetic breathing circuit, it is conceivable the respiratory breathing circuit would be reused. Respiratory therapy circuits like the ones used during nasal high flow are typically single use items. One of the reasons for this is to prevent contamination from one patient to another when the same flow source and/or humidifier are used.

The following embodiments relate to further alternatives for preventing contamination and infection to allow for the reuse of respiratory breathing circuits between patients during anaesthesia applications. However it should be noted these ideas are not exclusive to anaesthesia. It is conceivable the embodiments described below may be used in a general respiratory setting such as CPAP therapy to allow for reuse of breathing circuits in any application.

In some embodiments a filter may be used to prevent patient contamination of a breathing circuit. A filter may be a mechanical filter, to capture particles by direct interception. Alternatively, a filter may be electrostatic, to capture particles by electrical attraction. In other alternatives, the filter may be hydrophobic, so that the filter repels water and does not promote microbial growth. The filter should allow for air and water vapour (i.e. humidity) to pass through the filter without compromising filtration of infectious matter and condensate. In various examples, filter materials or filter media composition may comprise one or more of the following: Mineral fibres, Glass fibres, ceramic fibres, polypropylene, expanded polytetrafluoroethylene (PTFE), acrylics including modacrylics and thermoplastic polyurethane (e.g. Estane), cellulose fibres, or electrostatic fibres. Other filter materials or media have been described in this specification and those media or materials or particular characteristics or properties are re-iterated here.

A filter may be provided at a connection point between a patient interface (such as, but not limited to a nasal cannula or a nasal mask) and a respiratory breathing circuit. For example, a filter may be provided as a component to be inserted into an end of a conduit forming part of a respiratory breathing circuit, or as a component to be inserted into a patient interface to be connected to a breathing circuit.

With reference to FIGS. 22A to 22E, a filter connector or component 1010 comprises a filter or filter element 1012. In FIGS. 22A to 22E, the component 1010 is a connector adapted to connect between a main conduit of a breathing circuit and a patient interface or a patient interface tubing, having the same diameter as the main conduit. It will be appreciated some embodiments may utilise an interface tubing that has a smaller diameter than the main conduit. In other embodiments, the filter could be concentric with the main conduit and be designed to have the same diameter as the main conduit and interface or nasal cannula connections on either side. The filter or component comprising a filter or filter element may even be substantially elongated to facilitate the same filter material contact surface area as a substantially larger diameter design.

Thus, the component 1010 may comprise a union or socket connector or a reducing union or socket connector or adapter 1011 including a filter 1012. A reducing union or socket connector or adapter has one end (e.g. inlet) of a first diameter and an opposite end (outlet) of a second diameter, wherein the first diameter is greater than the second diameter, or diameters as necessary to operate with the components to which it must be fitted.

Figures 22A, 22B:
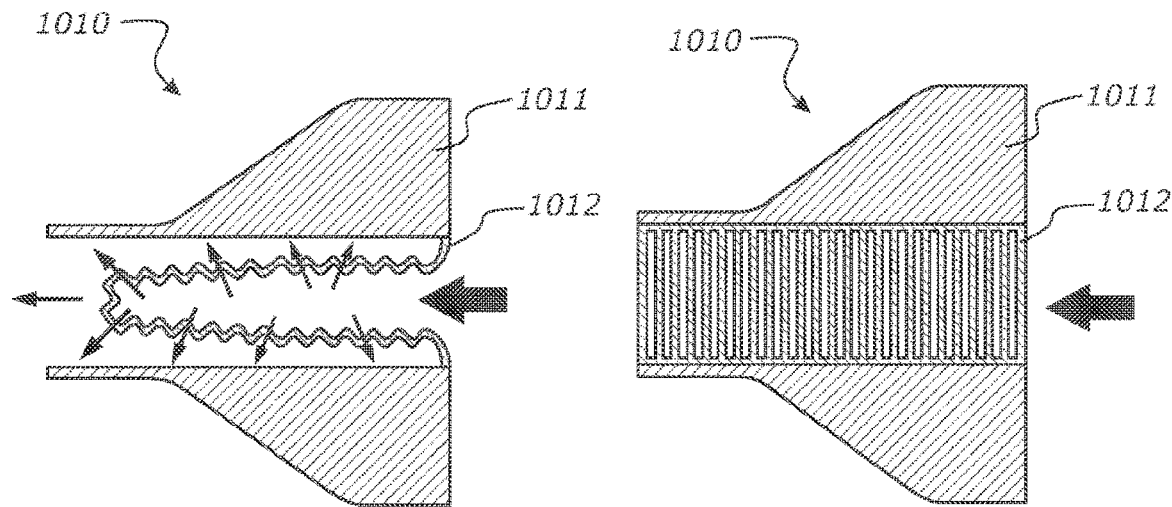
FIG. 22A is a schematic representation of a connector or component comprising a filter element.
FIG. 22B is a schematic representation of a connector or component comprising an alternative filter element.
Figures 22C, 22D:
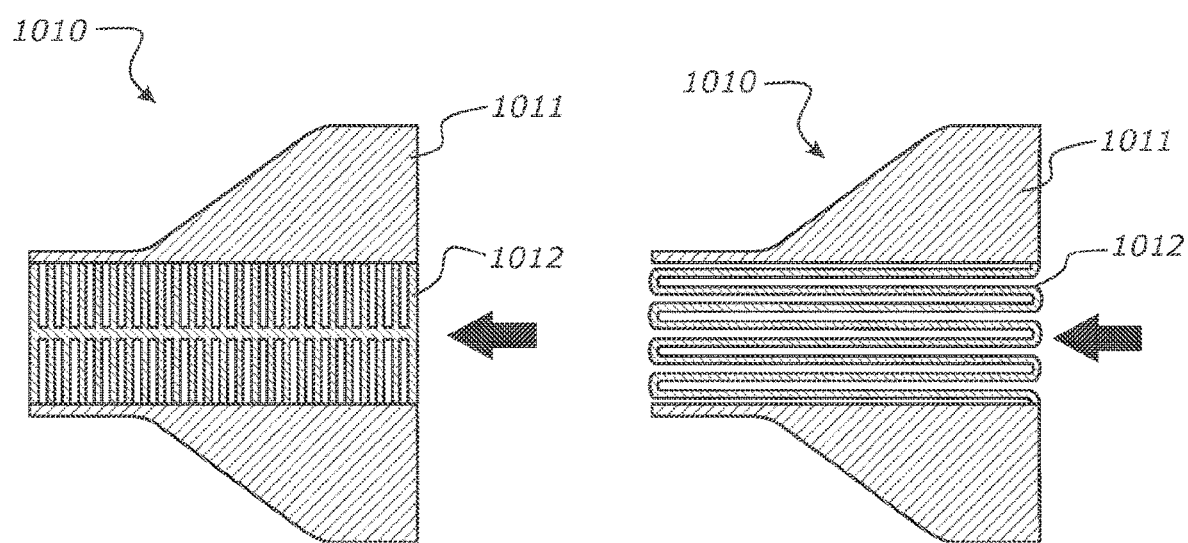
FIG. 22C is a schematic representation of a connector or component comprising another alternative filter element.
FIG. 22D is a schematic representation of a connector or component comprising yet another alternative filter element.

As illustrated in FIG. 22A, the filter 1012 may comprise a sock filter. Alternatively, as illustrated in FIG. 22B, the filter 1012 may comprise a stacked disc filter. Still further, as illustrated in FIG. 22C, the filter 1012 may comprise a spiral filter. Yet further, as illustrated in FIG. 22D, the filter 1012 may comprise a pleated sheet filter. In other alternatively, the filter 1012 may comprise a block of filter material. In another alternative, as illustrated in FIG. 22E, the filter 1012 may comprise a disc 1012a of filter material with streams of material 1012b free floating from or off the disc in the fluid flow. The free streaming material may vibrate at high flows, aiding in filtration. The streams may contain small holes to capture particulate.

As for example illustrated by FIGS. 22A to 22D, the filter 1012 is provided with a connector 1011 for connecting between a patient interface and a conduit of the respiratory breathing circuit. The filter 1012 may be provided as a separate filter element to be inserted into or attached to a conduit and/or patient interface. For example, the filter of FIG. 22E may be inserted into an end or a conduit and/or an inlet of a patient interface, and the interface and the conduit adapted to fit together to be in fluid communication, or may be integrated into the interface or as part of an interface arrangement itself.

In still further examples, a patient interface tube (e.g. item 1017 FIG. 26A) may be made from an open cell foam material with a sealing skin, such that the interface tube is breathable in that it allows water vapour to pass through it but does not allow the passage of liquid water or bulk flow of gases. In some embodiments the patient interface is a nasal cannula comprising one or two nasal prongs to fit into a patient's nostrils. In such an embodiment, each prong may provide a filter.

In some embodiments a filter in combination with a valve may be used to prevent patient contamination of a breathing circuit. For example, in some embodiments a filter component may comprise a one way valve 1013 and a filter attached to an outlet of the one way valve. In some embodiments the one way valve may be a duck bill valve. As illustrated in FIGS. 23A and 23B, an expanding filter material may be attached to the duckbill end of the valve, so that as the valve opens the filter material expands to allow flow through the valve and filter material and prevent contamination passing back through the valve.

In some embodiments a disinfectant may be used to kill or remove infectious matter in a breathing circuit, or alternatively reduce the level of infectious matter to a safe level. In this specification and claims, the word "prevent" should be interpreted to have an equivalent meaning to "reduce to acceptable levels". Some examples of some possible disinfectants (in liquid or gas form) may be ortho-phthalaldehyde, glutaraldehyde, hydrogen peroxide, and nitrogen dioxide.

Figure 24A:
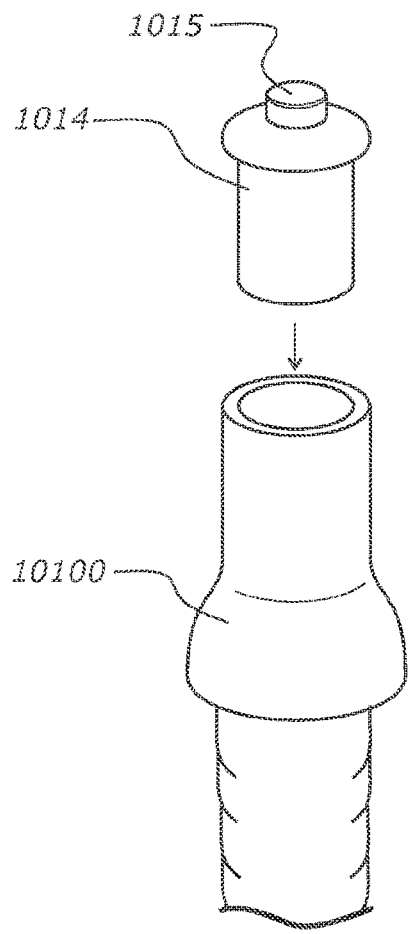
FIG. 24A illustrates a disinfection capsule or reservoir adapted to be inserted into an end of a breathing conduit.
Figure 24B:
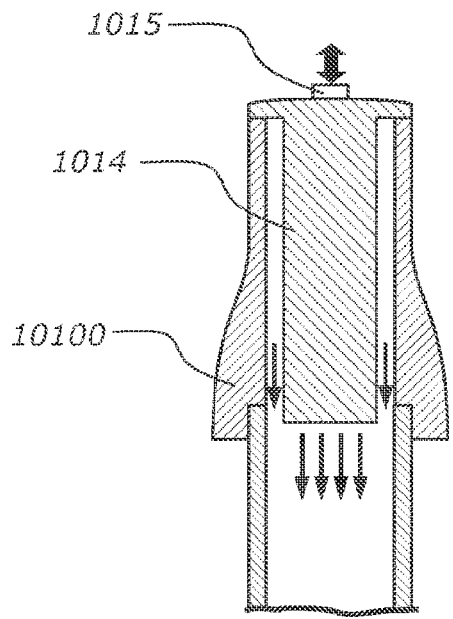
FIG. 24B is a schematic cross section representation of the disinfection capsule of FIG. 24A fitted into an end of a conduit.

In some embodiments, a disinfectant may be distributed into a breathing circuit via a disinfection reservoir that releases disinfectant when a circuit is not in use on a patient. For example, as illustrated in FIGS. 24A and 24B, a disinfection capsule 1014 that caps an end of the breathing circuit 10100 may be provided. The capsule may have a push button 1015 for release of disinfectant (FIG. 24A). The capsule 1014 could be built into the breathing circuit or may be a separate component that a user inserts into an end of the breathing circuit as illustrated. In some embodiments a reservoir may be provided in the walls of a conduit of the breathing circuit or a connector of the breathing circuit, and be released through one way valves into the breathing circuit via a release mechanism. The release mechanism may be actuated by an electric signal that is generated when a patient interface is removed from the circuit. In some embodiments a flushing disinfection unit may attach to each end of the breathing circuit. The disinfection unit may be used to alternately flush the breathing circuit with water or disinfectant. The flushing disinfection unit may be a separate unit or may be built into the humidifier.

Figure 25A:
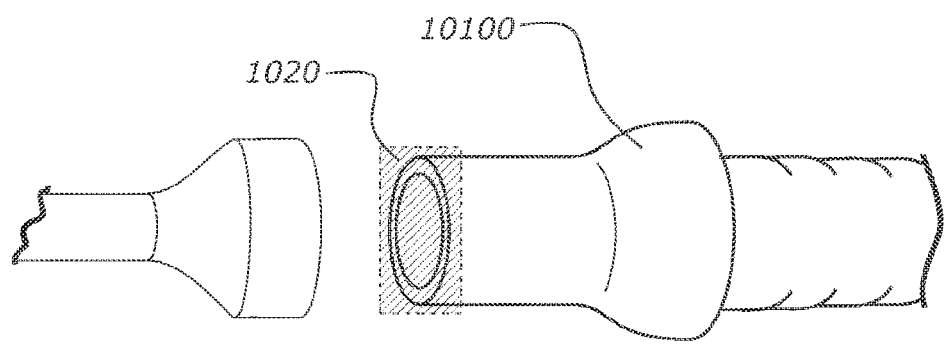
FIG. 25A illustrates an end of a breathing circuit conduit and a schematic representation of a sheet of radiation delivered at the end of the conduit to prevent contamination.

In some embodiments, a breathing circuit may be disinfected by providing radiation (for example ultraviolet light or near infrared ultra-short pulsed laser) to the breathing circuit to inactivate microorganisms. As illustrated in FIG. 25A, in some embodiments a sheet of radiation 1020 may be delivered at a connection point between a breathing circuit and a patient interface. For example, in some embodiments a radiation source may be built in to a connector 10100 at an end of a conduit of the breathing circuit. In some embodiments radiation may be provided as individual radiation beams built in throughout the circuit, or delivering radiation in beams and or sheets throughout the circuit. In some embodiments radiation is delivered to the breathing circuit continuously including during use of the circuit by a patient. In some embodiments radiation is delivered to the breathing circuit only when a patient interface is disconnected. In some embodiments a radiation source may be built into humidifier or other hardware of a respiratory breathing system upstream of the breathing circuit that connects with an end of the breathing circuit.

In some embodiments heat disinfection may be used to kill microorganisms in the breathing circuit. For example, in some embodiments a conduit of the breathing circuit may comprise heating wires or heating elements to prevent 'rain out' or condensation forming in the conduit. In some configurations heating elements such as wires may be positioned in the gases flow, inside the conduit. For example the heating elements may be laid through a lumen of the conduit, or may be placed against or fixed to an inner wall surface of the conduit. In some configurations heating elements may be integrated within a wall of the conduit, or may be wrapped around an outside surface of the conduit. Heating elements may be co-molded in the wall of the conduit, or may be clipped or bonded or otherwise held in place inside or outside the conduit. In a disinfecting cycle heat may be delivered to the breathing circuit by increasing the heat output of the breathing circuit heating elements for a period of time between patients (with or without the gas flow running) to kill microorganisms.

In some embodiments, a disinfection unit may be used that attaches to each end of the breathing circuit and disinfects by cycling hot water (e.g. at 90° C.) and detergent through the breathing circuit. The disinfection unit could be separate or built in with any other hardware (for example a humidifier) upstream of the breathing circuit. Alternatively the disinfection unit may be downstream of the breathing circuit. In some configurations the disinfection unit may be built in with a gases source, for example a blower unit. In some embodiments a heated collar may be provided at a connection point between the breathing circuit and a patient interface to stop infectious matter migration from the patient into the breathing circuit. In some embodiments, one or more filters and/or valves described above may be used in combination with a breathing circuit and disinfection unit or disinfection method described here. In some embodiments, a connector for connecting a breathing circuit to a patient interface described above may also comprise a heating element to heat the connector to disinfect the connection point between the circuit and the patient interface.

In some configurations a disinfection cycle (for example by disinfectant flush, radiation and/or heat as described above) may be automatically initiated or manually initiated. For example, a disinfecting cycle may be initiated automatically by disconnecting a patient interface from the breathing circuit. Alternatively a disinfection cycle could be activated on a timer sequence.

In some embodiments antimicrobial additives may be provided in the breathing circuit. For example, some possible additives include silver and silver based additives (colloidal silver, silver salts, silver zeolite, nano silver), siloxane based additives, Triclosan, and copper. Additives may be added to a breathing circuit by, for example a collar around an end or connection point of a breathing circuit where a patient interface is attached. The collar may be manufactured from an antimicrobial plastic. In some embodiments an entire breathing circuit may be made with antimicrobial additives, for example a breathing tube or conduit may be made from an antimicrobial plastic. Antimicrobial additives may be integrated into a conduit as an additive in the polymer that is used to make the conduit. In some embodiments, a release of antimicrobial additives may be activated by running water, or another disinfectant or applying heat or humidity or applying UV to a conduit comprising the additives. The disinfecting methods described above may be e used to release the antimicrobial additives in the conduit.

In some embodiments a cap 1025 may be provided to cover an end of the breathing circuit, as illustrated in FIGS. 26A and 26B. A cap may be provided at a connection point between a patient interface tube 1017 and a breathing circuit 10101, for example as shown in FIG. 26A. In some embodiments, a cap 1025 may be provided between a patient interface 10200 and a breathing circuit at a connection point adjacent to the patient interface, for example as illustrated in FIG. 26B. In some embodiments the cap 1025 is a separate piece of equipment that a user places on the end of a circuit when the patient interface is removed. In some embodiments the cap 1025 may be attached to the end of the breathing circuit, for example by a cord. In some embodiments a cap is built into the breathing circuit and is activated by a signal, for example an electrical, mechanical or magnetic signal, when the patient interface is removed or unplugged from the breathing circuit. In some embodiments, a pressure relief system or stop flow system may be included. For example, the cap 1025 may comprises a pressure release mechanism such as a relief valve to relieve excess pressure when the cap is fitted and in an instance when gases or pressure source continues to pressurize the breathing circuit.

In this way contamination cannot enter or is prevented from entering the breathing circuit when the interface is not attached (i.e., when the interface is changed between patients). As the flow travels in one direction (or predominately flows in one direction) contamination from the interface cannot enter or is prevented from entering the circuit when in use.

The cap can optionally also be made of a filter material or may comprise a one-way valve. In this way, additional protection from contamination can be provided. For example, this may find particular application in the case when the flow of gas is turned off to a patient interface, but the interface remains on a patient; condensate or contamination from the patient may be able to travel up the circuit if there is no cap or filter.

Alternatively, the gas supply may be triggered by the connection/disconnection of the interface (i.e., the flow always turns on or remains on, at least at a low level, when the interface is connected and turns off as soon as the interface is disconnected from the source of gas).

In some embodiments the breathing circuit may comprise an orifice to create a fast flow through the orifice to prevent infectious matter travelling back into the breathing circuit against the direction of flow through the orifice. This is related to the Peclet number, the ratio of the rate of advection to the rate of diffusion. If the Peclet number is greater than 1, advection dominates over diffusion and it would be unlikely infectious matter could diffuse into the breathing tube past the orifice. Ideally the higher the Peclet number (100, 1000 etc.), the less likely diffusion would influence the infectious matter and the less likely it would be to travel into the breathing circuit beyond the orifice.

In some embodiments, a one way valve system may be provided that only allows single direction flow from the breathing circuit to the patient interface. The one-way valve allows a flow of breathing gases to pass from the breathing circuit to the patient interface and the patient, but prevents flow from the patient interface back into the breathing circuit. The one-way valve prevents or reduces infectious matter entering the breathing circuit from the patient interface. The patient interface may be discarded after use, and the breathing circuit subsequently used by another patient.

In some embodiments a valve may be provided at a connection point between a patient interface and a respiratory breathing circuit. For example, in some embodiments a valve may be provided as a component to be inserted into an end of a conduit forming part of a respiratory breathing circuit, or in some embodiments, a valve may be provided as a component to be inserted into a patient interface to be connected to a breathing circuit.

In some embodiments, the valve may be provided within a connector for connecting a patient interface to a breathing circuit. In some embodiments, a valve may be provided as a separate element to be inserted into or attached to a conduit and/or patient interface.

Figure 27A:
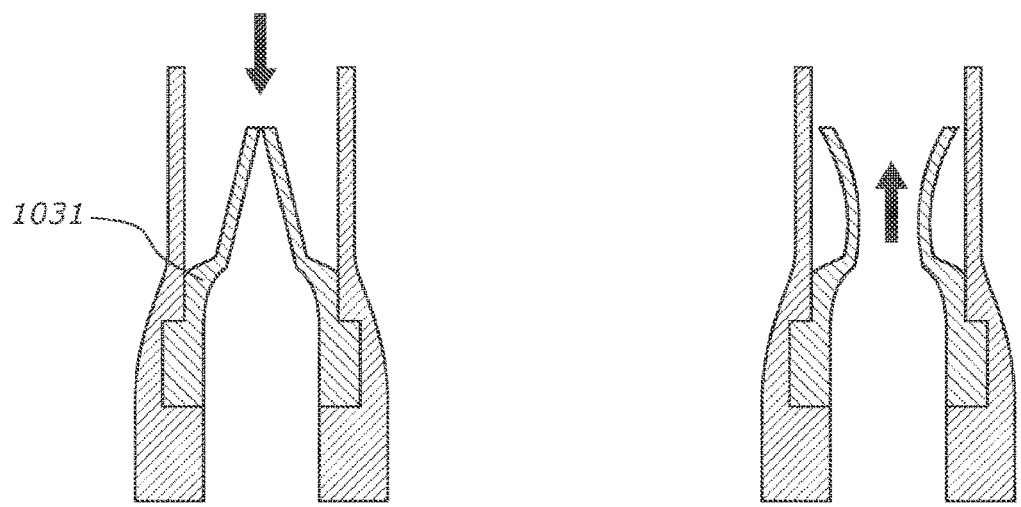
FIG. 27A illustrates a one way valve in a portion of a breathing circuit or patient interface, and shows the valve in a closed position and also in an open position.
Figure 27B:
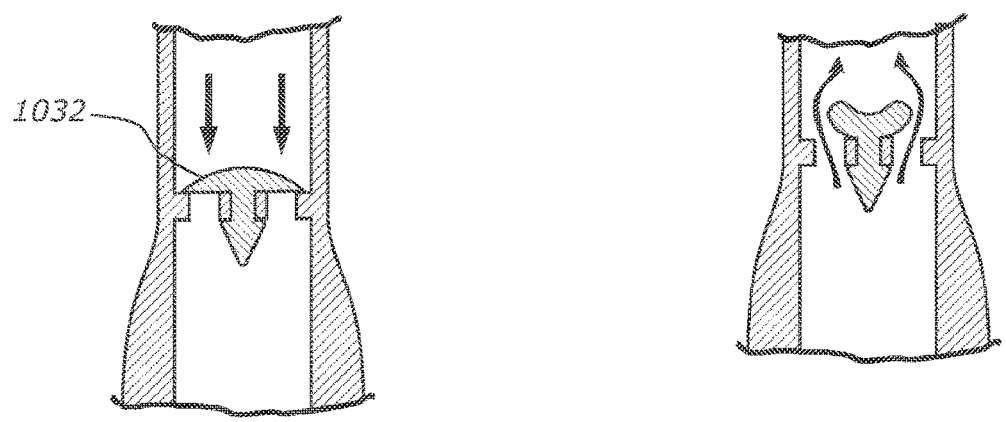
FIG. 27B illustrates an alternative one way valve in a portion of a breathing circuit or patient interface, and shows the valve in a closed position and also in an open position.
Figure 27C:
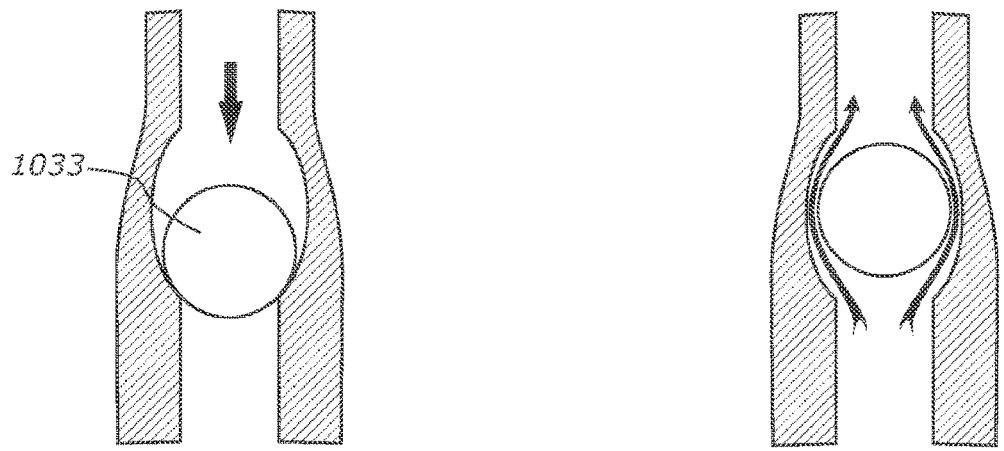
FIG. 27C illustrates an alternative one way valve in a portion of a breathing circuit or patient interface, and shows the valve in a closed position and also in an open position.

In some embodiments, the valve may be a duckbill valve 1031 as shown in FIG. 27A, an umbrella valve 1032 as shown in FIG. 27B, a check ball valve 1033 as shown in FIG. 27C, or a constant velocity valve.

In some embodiments a valve may be inspiratory triggered. This means the flow is only delivered during inspiration when the pressure allows the valve to open. During expiration the valve closes and no flow is allowed to pass back into the breathing circuit.

In some embodiments the breathing circuit may include a pressure relief system to ensure the breathing circuit is not over pressurized.

In some embodiments a flow source providing a flow of respiratory gases to the breathing circuit, or other hardware of a respiratory breathing system upstream of the breathing circuit, comprises a switch that allows the flow to be turned ON (e.g. to 70 L/min or some other high flow rate or pressure associated with a high flow rate) and OFF (e.g. to 10 L/min or some other low flow rate or pressure associated with a low flow rate).

When the system is in OFF, there is still a low flow from the flow source to the patient interface and therefore reverse flow and transfer of infectious matter back into the breathing circuit is not possible. For example, in some embodiments, an item of equipment upstream of the breathing circuit such as a flow source includes an electrical connection that allows/starts the OFF flow when the flow source is connected to the breathing circuit and allows/starts the ON flow when the breathing circuit is connected to the patient interface. In some embodiments, an item of equipment upstream of the breathing circuit such as a flow source includes a mechanical switch (e.g. push valve) that allows different sized orifice openings to be introduced to the flow path to control the flow.

In some embodiments a mesh of hydrophobic material may be provided at a connection point between a patient interface and a respiratory breathing circuit. For example, in some embodiments a mesh may be provided at an end of a conduit forming part of a respiratory breathing circuit, or in some embodiments, a mesh may be provided at a patient interface to be connected to a breathing circuit. The mesh of hydrophobic material may have a pore size that is determined to ensure there is enough supply pressure at 70 L/min (or some other target high flow) to get the flow to pass through the pores of the mesh from the breathing circuit to the patient interface, but the pressure of exhalation from the patient is too small for the exhaled breath to go back through the mesh from the patient interface to the breathing circuit.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

As used herein the term "(s)" following a noun means the plural and/or singular form of that noun.

As used herein the term "and/or" means "and" or "or", or where the context allows both.

Where the terminology "configured to" is used herein, that terminology could alternatively be replaced with "arranged to" or "adapted to".

Where, in the foregoing description reference has been made to integers or components having known equivalents thereof, those integers are herein incorporated as if individually set forth.

The disclosure may also be said broadly to consist in the parts, elements and features referred to or indicated in the specification of the application, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Certain features, aspects and advantages of some configurations of the present disclosure have been described with reference to use of the gas humidification system with a respiratory therapy system. However, certain features, aspects and advantages of the use of the gas humidification system as described may be advantageously be used with other therapeutic or non-therapeutic systems requiring the humidification of gases. Certain features, aspects and advantages of the methods and apparatus of the present disclosure may be equally applied to usage with other systems.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Features from any of the configurations describe above may be combined with each other and/or a respiratory support system or humidifier may comprise one or more of the above described configurations. Moreover, not all of the features, aspects and advantages are necessarily required to practice the present disclosure. Accordingly, the scope of the present disclosure is intended to be defined only by the claims that follow.

The invention claimed is:

1. A filter for use in a high flow respiratory support system for delivering humidified gas to a user or a patient, the filter comprising:
   a housing comprising a gases inlet port and a gases outlet port;
   wherein at least one of the gases inlet port and the gases outlet port comprises at least a pair of male connection fingers extending from at least one of the gases inlet port and the gases outlet port, wherein the pair of male connection fingers are adapted for connection with a connector provided at a terminal end of a conduit;
   wherein at least one of the gases inlet port and/or gases outlet port comprises at least one sealing member; and
   wherein the at least one sealing member provides at least one sealing surface that seals with a surface of the connector provided at the terminal end of the conduit, and wherein the surface of the connector is brought to bear upon the at least one sealing surface.

2. The filter of claim 1, wherein the gases inlet port comprises a gases inlet port coupling feature and the gases outlet port comprises a gases outlet port coupling feature, wherein the gases inlet port coupling feature and the gases outlet port coupling feature are different coupling features.

3. The filter of claim 1, wherein the gases outlet port comprises a medical taper connection.

4. The filter of claim 1, wherein the gases outlet port comprises a 22 mm medical taper connection.

5. The filter of claim 1, wherein the pair of male connection fingers extend from the gases inlet port.

6. The filter of claim 1, wherein the pair of male connection fingers comprise indentations or recesses shaped for engagement of a projection or protrusion located on the connector at a terminal end of the conduit.

7. The filter of claim 1, wherein the at least one sealing member is located at or adjacent with a base of the male connection fingers.

8. The filter of claim 7, wherein the at least one sealing member is an O-ring.

9. The filter of claim 1, wherein the male connection fingers extending from at least one of the gases inlet port and/or gases outlet port is inside a cylindrical wall of the gases inlet port and/or gases outlet port.

10. A filter for use in a high flow respiratory support system for delivering humidified gas to a user or a patient, the filter comprising:
a housing comprising a gases inlet port and a gases outlet port, wherein the gases inlet port and/or gases outlet port comprise an adapter insert, the adapter insert comprising at least one pair of male connection fingers extending from at least one of the gases inlet port and the gases outlet port, wherein the at least one pair of male connection fingers are adapted for connection with a connector provided at a terminal end of a conduit.

11. The filter of claim 10, wherein the adapter insert comprises one or more retention members, wherein each of the one or more retention members is engageable with a portion of an interior surface of the housing.

12. The filter of claim 11, wherein each of the one or more retention members is configured to engage with the interior surface of the housing to retain the adapter insert within a port into which an adapter is inserted.

13. The filter of claim 12, wherein each of the one or more retention members is configured to resist axial displacement of the adapter in a direction toward an exterior end of the port.

14. The filter of claim 11, wherein each of the one or more retention members comprise at least a hook or other surface projection to engage the interior surface of the housing.

15. The filter of claim 11, wherein the adapter insert comprises a first end and a second end, wherein the male connection fingers extend from the first end and each of the one or more retention members extend from the second end, and wherein a shank portion connects the first end with the second end.

16. The filter of claim 15, wherein the shank portion comprises a gas flow path for a passage of gases therethrough between each of the first end and the second end.

17. The filter of claim 15, wherein the adapter insert comprises at least one sealing member provided about the shank portion.

18. The filter of claim 15, wherein the adapter insert comprises at least one sealing member provided substantially at or adjacent with a first end of the adapter insert.

19. The filter of claim 18, wherein the at least one sealing member is an O-ring.

20. The filter of claim 18, wherein the at least one sealing member is located at or adjacent with a base of the male connection fingers.

21. The filter of claim 20, wherein the at least one sealing member is an O-ring.

22. The filter of claim 15, wherein the first end of the adapter insert comprises a radially extensive ledge or lip.

23. The filter of claim 18, wherein the at least one sealing member provides for at least one sealing surface for sealing with a surface of the connector provided at the terminal end of the conduit when the surface of the connector is brought to bear upon the at least one sealing surface.

24. The filter of claim 23, wherein the at least one sealing member is an O-ring.

25. The filter of claim 15, wherein one or more splines or ribs are located about the shank portion, wherein the one or more splines or ribs extend longitudinally along the shank portion.

26. The filter of claim 16, wherein the gas flow path transitions from a larger internal diameter at the second end of the adapter insert to a smaller internal diameter at the first end of the adapter insert.

27. The filter of claim 26, wherein the gas flow path transitions from the larger internal diameter to the smaller internal diameter in a graduated or linear progression from the second end of the adapter insert to the first end of the adapter insert.

28. An apparatus for use in a respiratory support system for delivering humidified gas to a patient, the apparatus comprising:
a filter according to claim 1, that is positioned downstream of a humidifier to receive humidified gas from the humidifier; and
a patient interface for delivering humidified gas to the patient, wherein the patient interface is in pneumatic communication with the filter downstream of the humidifier.

29. The apparatus of claim 28, wherein the patient interface is a non-sealing patient interface.

30. The apparatus of claim 28, wherein the filter or a filtration material of the filter comprises electrostatic, hydrophilic, or hydrophobic properties.

31. The apparatus of claim 28, wherein the filter is integrally formed with a patient interface for delivering humidified gas.

32. The apparatus of claim 28, wherein the patient interface for delivering humidified gas comprises a breathable tube.

33. The apparatus of claim 28, wherein the patient interface for delivering humidified gas comprises a flexible, unheated tube.

34. The apparatus of claim 28, wherein the patient interface for delivering humidified gas comprises one or more nasal delivery elements, the one or more nasal delivery elements are configured to be non-sealingly positioned in one or more nares of a patient.

35. The apparatus of claim 34, wherein the patient interface for delivering humidified gas comprises a flow manifold, wherein the flow manifold has a one or more lateral channels, wherein the one or more lateral channels of the flow manifold corresponds to one or more nasal delivery elements, wherein the one or more lateral channels receives a gas flow and channels the gas flow to the one or more nasal delivery elements corresponding to the one or more lateral channels.

36. The apparatus of claim 28, wherein the patient interface for delivering humidified gas is configured to supply a heated and humidified high-flow gas flow having a flow rate within a range of 5 L/min to 150 L/min.

37. A kit for use in a respiratory support system for delivering humidified gas to a patient, the kit comprising:
a filter according to claim 1; and
a patient interface.

38. The kit of claim 37, wherein the patient interface comprises a breathable tube.

39. The kit of claim 37, wherein the patient interface comprises a flexible, unheated tube.

40. The kit of claim 37, wherein the patient interface comprises one or more nasal delivery elements, the one or more nasal delivery elements are configured to be non-sealingly positioned in one or more nares of a patient.

41. The kit of claim 37, wherein the patient interface for delivering humidified gas is configured to supply a heated and humidified high-flow gas flow having a flow rate within a range of 5 L/min to 150 L/min.

42. The filter of claim 11, wherein the adapter insert comprises a plurality of retention members arranged to form an array.

43. A filter for use in a high flow respiratory support system for delivering humidified gas to a user or a patient, the filter comprising:
- a housing comprising a gases inlet port and a gases outlet port;
- wherein at least one of the gases inlet port and the gases outlet port comprises at least a pair of male connection fingers extending from at least one of the gases inlet port and the gases outlet port, wherein the pair of male connection fingers are adapted for connection with a connector provided at a terminal end of a conduit;
- wherein at least one of the gases inlet port and/or gases outlet port comprises at least one sealing member; and
- wherein the at least one sealing member provides at least one sealing surface that seals with a surface of the connector provided at the terminal end of the conduit when the surface of the connector is brought to bear upon the at least one sealing surface.

\* \* \* \* \*